United States Patent [19]

Kondo et al.

[11] Patent Number: 5,310,724

[45] Date of Patent: May 10, 1994

[54] HERBICIDAL SUBSTITUTED PHENYL-1,2,4-TRIAZOL-5(1H)-THIONES

[75] Inventors: Kiyoshi Kondo, Kanagawa; Hiromichi Kono, Tokyo, both of Japan; Kirk A. Simmons; John A. Dixson, both of Newtown, Pa.; Blaik P. Halling, Yardley, Pa.; Ernest L. Plummer; Marjorie J. Plummer, both of Washington Crossing, Pa.; John M. Tymonko, Hamilton Square, N.J.

[73] Assignee: FMC Corporation, Philadelphia, Pa.

[21] Appl. No.: 933,598

[22] Filed: Aug. 20, 1992

Related U.S. Application Data

[63] Continuation of Ser. No. 680,771, Apr. 1, 1991, abandoned, which is a continuation of Ser. No. 477,773, Feb. 9, 1990, abandoned.

[51] Int. Cl.$^5$ ................. A01N 43/653; C07D 249/12
[52] U.S. Cl. .................... 504/273; 548/264.6
[58] Field of Search .............. 71/92; 548/264.6; 504/273

[56] References Cited

U.S. PATENT DOCUMENTS 3,922,162  11/1975  Krenzer ........................... 71/92
4,702,763  10/1987  Maravetz ....................... 548/263.2

FOREIGN PATENT DOCUMENTS 2546887  12/1984  France .
160447    8/1983   German Democratic Rep. .
1421231   1/1976   United Kingdom .
2021586  12/1979   United Kingdom .

OTHER PUBLICATIONS

Grashey et al, "Carbonylverbindungen, etc" *Chem-Ztg*, 100 (11) pp. 496–497 (1976).
Grashey et al, "Acetylderivate der" *TL* 29, pp. 2947–2950 (1972).
Landquist, "Oxidative Cyclization of ketone, etc" J. of Chem. Soc. C (2) pp. 323–324 (1970).
Abil-Fattah et al, "Reactions with, etc" CA 105: 226455a (1986).

Khripak et al, "Aminomethylation of, etc" CA83:147418q (1975).
Giudicelli et al, "Amino-2-oxidazoles, etc" *Bull. Soc. Chim. Fr.*, (3), pp. 870–874 (1969).

*Primary Examiner*—Patricia L. Morris
*Attorney, Agent, or Firm*—H. Robinson Ertelt; Robert M. Kennedy

[57] ABSTRACT

The present application discloses herbicidal substituted-phenyl-1,2,4-Triazol-5(1H)-thiones and -ones, herbicidal compositions containing these compounds, methods of preparing them, and methods for controlling undesired plant growth by preemergence and/or post-emergence application of the herbicidal compositions to the locus where control is desired. The herbicidal compounds are compounds of the formula $$R^1-N_1 \overset{W}{\underset{N_2}{\overset{\parallel}{\underset{3}{-}}}}\overset{5}{\underset{}{}} \overset{4}{\underset{R}{}}N-Ar$$

wherein:

Ar is selected from

[structures shown: a phenyl ring with substituents $R^2$, $R^3$, $R^4$, $R^5$, $R^6$, and a pyridyl ring with $-N(R^7)(R^8)$]

R is selected from haloalkyl;
$R^1$ is selected from alkyl;
$R^2$ is selected from hydrogen, halogen, alkyl, haloalkoxy, haloalkyl, alkoxy, alkynyl, alkylthio, nitro, amino and cyano;
$R^3$ is selected from hydrogen, halogen, alkyl, alkoxy, alkynyl, nitro, amino, mono- or disubstituted amino, cyano and hydroxy;
$R^3$ is selected from hydrogen, halogen, alkyl, alkoxy, (Abstract continued on next page.)

alkynyl, nitro, amino, mono- or disubstituted amino, cyano and hydroxy;

$R^4$ is selected from hydrogen, halogen, alkyl, alkenyl, alkynyl, trimethylsilylalkynyl, cyano, nitro, amino, haloalkyl, mono- or disubstituted amino, tetralkylammonium halide, hydroxy, alkoxy, phenoxy, benzyl, benzyloxy, alkylthio, alkylsulfonyl, alkylcarbonyl, phenylcarbonyl, pyrrolidinyl, piperidinyl, morpholinyl, alkylthioalkoxy, vinyloxy, alkylvinyloxy, halovinyloxy, allyloxy, cycloalkylalkoxy, cycloalkoxy, and haloalkoxy;

$R^5$ is selected from hydrogen, halogen, alkyl, alkoxy, haloalkoxy and haloalkyl; or $R^3$ and $R^4$ or $R^4$ and $R^5$ may be joined to form —OCH$_2$O—, —CH$_2$C(CH$_3$)$_2$O—, —OC(CH$_3$)(CH$_2$CH$_3$)O—, —N(CH$_2$CH$_3$)CH$_2$CH$_2$N(CH$_2$CH$_3$)—, —OCH$_2$CH$_2$N[CH(CH$_3$)$_2$]—, —OCH$_2$CH$_2$O—, —OC(CH$_3$)$_2$O—, —C(O)C(CH$_3$)$_2$O—, or —CH$_2$CH$_2$CH$_2$O—;

$R^6$ is selected from hydrogen, halogen, alkyl and alkylthio;

$R^7$ and $R^8$ are alkyl, not necessarily the same; and

W is selected from S and O.

15 Claims, No Drawings

HERBICIDAL SUBSTITUTED PHENYL-1,2,4-TRIAZOL-5(1H)-THIONES

This application is a continuation of application Ser. No. 680,771, filed Apr. 1, 1991, now abandoned, which is a continuation of application Ser. No. 477,773, filed Feb. 9, 1990, now abandoned.

The invention described in this application pertains to weed control in agriculture, horticulture, or other fields where there is a desire to control unwanted plant growth. More specifically, the present application describes novel herbicidal substituted-phenyl-1,2,4-triazol-5(1H)-thiones and -ones, herbicidal compositions containing the new compounds, methods of preparing these compounds, and methods for controlling undesired plant growth by preemergence and/or postemergence application of the herbicidal compositions to the locus where control is desired. The present compounds may be used to effectively control a variety of both grassy and broadleaf plant species.

A number of 1,2,4-triazol-thiones and -ones are known in the art. French Patent Application 2,546,887, published Dec. 7, 1984, for example, discloses (as reported in Derwent Abstracts, accession no. 85-020678/04) pesticidal triazol-3-thiones of the Formula

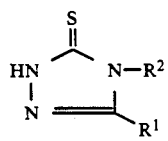

wherein $R^1$ is alkyl or aryl, and $R^2$ is aryl, benzyl, 2-hydroxyethyl, anilino or aroylamino.

Belgium Patent Application 802,530, published Jan. 21, 1974, discloses (as reported in Derwent Abstracts, accession no. 07240V/05) insecticidal and acaricidal compounds of the Formula

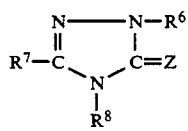

where $R^6$ is $R^4$ or $-CH_2-X-P(Y)R^1R^2$, $R^8$ is $R^5$ or $-CH_2-X-P(Y)R^1R^2$, only one of $R^6$ and $R^8$ is $-CH_2-X-P(Y)R^1R^2$, $R^7$ is $R^3$ and is $F_2CCl$ or 1-6C-fluoroalkyl when $R^8$ is $R^5$, X, Y and Z are O or S and Z is O when $R^8$ is $R^5$, $R^1$ is 1-4C-alkyl, (1-4C-alkyl)amino or 1-4C-alkoxy, $R^2$ is 1-4C-alkyl, (1-4C-alkyl)amino, 1-4C-alkoxy or Ph, $R^3$ and $R^4$ are each 1-6C-alkyl or 3-8C-cycloalkyl and are 3-4C-alkenyl when $R^6$ is $R^4$, $R^5$ is 1-6C-alkyl, 3-8C-cycloalkyl or phenyl optionally substituted by halogen or methyl.

U.S. Pat. No. 3,922,162, issued Nov. 25, 1975, discloses herbicidal compounds of the Formula

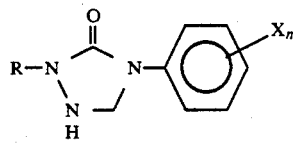

wherein R is alkyl, X is selected from the group consisting of alkyl, alkoxy, alkylthio, halogen, haloalkyl, and nitro, and n is an integer from 1 to 3.

Belgium Patent Application 876,557, published Nov. 26, 1979, discloses (as reported in Derwent Abstracts, accession no. 85976B/48) fungicidal compounds of the Formula

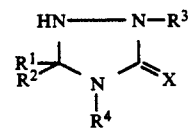

wherein $R^1$ is H or $R^2$, $R^2$ is cycloalkyl or 1-6C alkyl, or $R^1$ and $R^2$, together with the triazoline ring, form a spiran optionally substituted by methyl in the 1 and 3 positions, $R^3$ is 1-6C-alkyl, phenyl, phenyl substituted by 1-3 alkyl groups or $NO_2$, and X is O or S, provided that when X=O, then $R^4$H, phenyl or phenyl substituted by 1-3 halogens, and when X=S, then $R^4$=1-6C-alkyl, phenyl or phenyl substituted by 1-3 halogens.

Grashey et al., *Chem-Ztg.*, Vol. 100(11), p. 496 (1976) discloses (as reported in Chemical Abstracts, on-line registry no. 13136-33-9) 2,4-dihydro-5-methyl-2,4-diphenyl-3H-1,2,4-triazol-3-thione, a compound of the Formula

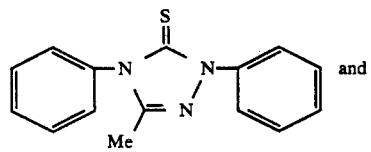

2,4-dihydro-4,5-diphenyl-2-(phenylmethyl)-3H-1,2,4-triazole-3-thione, a compound of the Formula

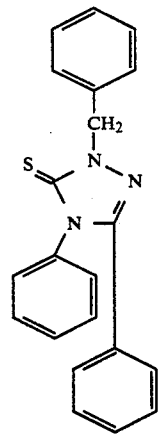

These compounds appear (based on Chemical Abstracts, accession no. CA86(19):139948j) to be intermediates in disclosed synthesis processes.

Lanquist, *J. Chem. Soc. C,* (2), pp. 323-4 (1970) discloses (see also Chemical Abstracts, on-line registry no. 25976-83-4) as an intermediate 1,3-dimethyl-4-phenyl-Δ²-1,2,4-triazolin-5-thione, a compound of the Formula

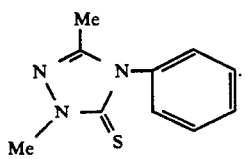

Abdel-Fattah et al., *Egypt. J. Chem.*, Vol. 27(3) pp. 321-8 (1985) discloses (as reported in Chemical Abstracts on-line registry no. 54559-49-8) 4,5-dihydro-3,4-diphenyl-5-thioxo-1H-1,2,4-triazol-1-propanenitrile, a compound of the Formula

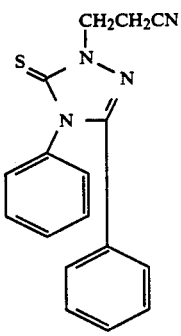

This compound appears (based on Chemical Abstracts, accession no. CA:105(25):226455a) to be the product of a reaction involving 1,2,4-triazol-5-thiones.

Khripak et al., *Khim. Geterosikl. Soedin.*, (7), pp. 1000-2 (1975) discloses (as reported in Chemical Abstracts on-line registry no. 56807-56-8) 2,4-dihydro-2-(hydroxymethyl)-4,-5-diphenyl-3H-1,2,4-triazol-3-thione, a compound of the Formula

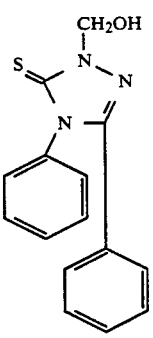

This compound appears (based on Chemical Abstracts, accession no. CA83(17):147418q) to be the product of a reaction involving 1,2,4-triazol-5-thiones.

Giudicelli et al., *Bull. Soc. Chim. Fr.*, (3), pp. 870-4 (1969) discloses (as reported in Chemical Abstracts on-line registry no. 960-57-6) 1-methyl-3,4-diphenyl-$\Delta^2$-1,2,4-triazoline-5-thione, a compound of the Formula

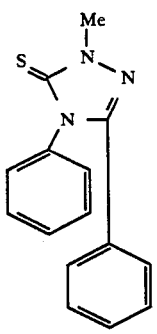

German Patentschrift 160,447, published Aug. 3, 1983 discloses herbicidal 1,2,4-triazolin-5-ones of the Formula

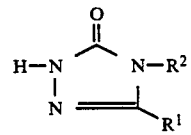

wherein $R^1$ and $R^2$ are each H or optionally substituted alkyl, aryl, aralkyl, or cycloalkyl, where typical substitutions are one or more of halo, hydroxy, amino (optionally substituted by alkyl and/or aryl), alkoxy, aryloxy, alkylthio or arylthio.

The herbicidal compounds of the present invention are compounds of Formula I

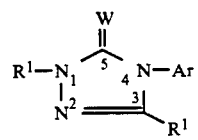

wherein:
Ar is selected from

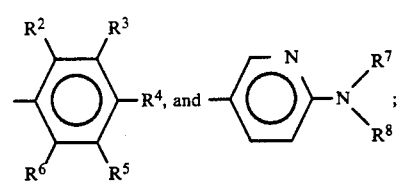

R is selected from haloalkyl;
$R^1$ is selected from alkyl;
$R^2$ is selected from hydrogen, halogen, alkyl, haloalkoxy, haloalkyl, alkoxy, alkynyl, alkylthio, nitro, amino and cyano;
$R^3$ is selected from hydrogen, halogen, alkyl, alkoxy, alkynyl, nitro, amino, mono- or disubstituted amino, cyano and hydroxy;
$R^4$ is selected from hydrogen, halogen, alkyl, alkenyl, alkynyl, trimethylsilylalkynyl, cyano, nitro, amino, haloalkyl, mono- or disubstituted amino, tetralkylammonium halide, hydroxy, alkoxy, phenoxy, benzyl, benzyloxy, alkylthio, alkylsulfonyl, alkylcarbonyl, phenylcarbonyl, pyrrolidinyl, piperidinyl, morpholinyl, alkylthioalkoxy, vinyloxy, alkylvinyloxy, halovinyloxy, allyloxy, cycloalkylalkoxy, cycloalkoxy, and haloalkoxy;

$R^5$ is selected from hydrogen, halogen, alkyl, alkoxy, haloalkoxy and haloalkyl; or $R^3$ and $R^4$ or $R^4$ and $R^5$ may be joined to form —OCH$_2$O—, —CH$_2$C(CH$_3$)$_2$O—, —OC(CH$_3$)(CH$_2$CH$_3$)O—, —N(CH$_2$CH$_3$)CH$_2$CH$_2$N(CH$_2$CH$_3$)—, —OCH$_2$CH$_2$N[CH(CH$_3$)$_2$]—, —OCH$_2$CH$_2$O—, —OC(CH$_3$)$_2$O—, —C(O)C(CH$_3$)$_2$O—or —CH$_2$CH$_2$CH$_2$O—, $R^6$ is selected from hydrogen, halogen, alkyl and alkylthio;

$R^7$ and $R^8$ are alkyl, not necessarily the same; and

W is selected from S and O.

As used herein, the term halogen, employed alone or in combination with other terms, denotes a species selected from the group consisting of chlorine, fluorine and bromine.

It is often preferable that any alkyl group or alkyl portion of any group herein have 1–6 carbon atoms, and that any alkenyl or alkynyl group or alkenyl or alkynyl portion of any group herein have 3–6 carbon atoms.

A preferred subgenus of this invention comprises the compounds of Formula I in which:

R is fluoroalkyl, most preferably CF$_3$;
$R^1$ is CH$_3$;
W is S; and
Ar is

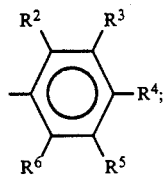

wherein:
$R^2$ is halogen, alkyl, haloalkyl or haloalkoxy, more preferably haloalkoxy, most preferably OCHF$_2$;
$R^3$ is hydrogen, halogen or alkyl, more preferably halogen, most preferably F or Cl;
$R^4$ is alkoxy, vinyloxy, cycloalkoxy or mono- or di-substituted amino, more preferably cycloalkoxy or alkoxy, most preferably cyclobutoxy or isopropoxy; or
$R^3$ and $R^4$ are joined to form —CH$_2$C(CH$_3$)$_2$O—, —OC(CH$_3$)(CH$_2$CH$_3$)O—or —C(O)C(CH$_3$)$_2$O—;
$R^5$ is halogen, alkyl or haloalkoxy, most preferably difluoromethoxy; and
$R^6$ is preferably hydrogen or halogen, more preferably halogen, most preferably F, Cl.

Specific embodiments exhibiting particularly effective weed control at low preemergence and/or post-emergence application rates and/or showing a selectivity particularly favorable to certain crop plants include compounds of the Formula

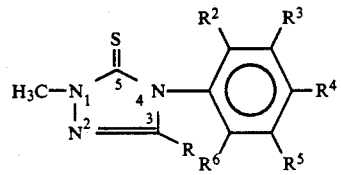

wherein:
R is CF$_3$, $R^2$ and $R^5$ are Cl, $R^3$ and $R^6$ are H, and $R^4$ is

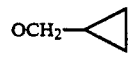

R is CF$_3$, $R^2$ and $R^5$ are Cl, $R^3$ and $R^6$ are H, and $R^4$ is NH (CH$_2$CH$_3$);
R is CF$_3$, $R^2$ is SCH$_3$, $R^3$ and $R^6$ are H, $R^4$ is OCH(CH$_3$)$_2$, and $R^5$ is Cl;
R is CF$_3$, $R^2$ is Cl, $R^3$, $R^5$ and $R^6$ are H, and $R^4$ is N(CH$_2$CH$_3$)$_2$;
R is CF$_3$, $R^3$, $R^5$ and $R^6$ are H, and $R^4$ is N(CH$_2$CH$_3$)(CH$_2$CF$_3$) ;
R is CF$_3$, $R^2$ and $R^5$ are Cl, $R^3$ and $R^6$ are H, and $R^4$ is OCH$_2$CH$_2$Br;
R is CF$_3$, $R^2$ and $R^5$ are Cl, $R^3$ and $R^6$ are H, and $R^4$ is

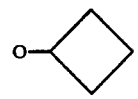

R is CF$_3$, $R^2$ is OCHF$_2$, $R^3$ and $R^6$ are H, $R^4$ is OCH(CH$_3$)$_2$, and $R^5$ is Cl;
R is CF$_3$, $R^2$, $R^3$, $R^5$, and $R^6$ are F, and $R^4$ is N(CH$_3$)$_2$;
R is CF$_3$, $R^2$, and $R^5$ are Cl, $R^3$ and $R^6$ are H, and $R^4$ is OCH=CF$_2$;
R is CF$_3$, $R^2$ is F, $R^3$ and $R^6$ are H, $R^4$ is N(CH$_2$CH$_3$)$_2$, and $R^5$ is Cl;
R is CF$_3$, $R^2$, $R^3$, $R^5$, and $R^6$ are F, and $R^4$ is N(CH$_2$CH$_3$)$_2$;
R is CF$_3$, $R^2$ and $R^5$ are Cl, $R^3$ and $R^6$ are H, and $R^4$ is OC (CH$_3$)$_3$;
R is CF$_3$, $R^2$ is Cl , $R^3$ and $R^6$ are H, $R^4$ is OCH(CH$_3$)$_2$, and $R^5$ is CH$_3$;
R is CF$_3$, $R^2$ is F, $R^3$ and $R^6$ are H, $R^4$ is OCH$_3$, and $R^5$ is cl
R is CF$_3$, $R^2$ and $R^5$ are Cl, $R^3$ and $R^6$ are H, and $R^4$ is OCH$_2$CH=CH$_2$;
R is CF$_3$, $R^2$ and $R^5$ are Cl, $R^3$ and $R^6$ are H, and $R^4$ is N (CH$_2$CH$_3$)$_2$;
R is CF$_3$, $R^2$ and $R^5$ are Cl, $R^3$ is NH$_2$, $R^4$ is OCH(CH$_3$)$_2$, and $R^6$ is H;
R is CF$_3$, $R^2$ is F, $R^3$ and $R^6$ are H, $R^4$ is OCH(CH$_3$)$_2$, and $R^5$ is Cl;
R is CF$_3$, $R^2$ and $R^5$ are Cl, $R^3$ are $R^6$ are H, and $R^4$ is OCH$_2$CH$_2$CH$_3$;
R is CF$_3$, $R^2$ and $R^5$ are Br, $R^3$ and $R^6$ are H, and $R^4$ is OCH(CH$_3$)$_2$;
R is CHF$_2$, $R^2$ and $R^5$ are Cl, $R^3$ and $R^6$ are H, and $R^4$ is OCH(CH$_3$)$_2$;
R is CF$_3$, $R^2$ and $R^5$ are Cl, $R^3$ and $R^6$ are H, and $R^4$ is OCH$_2$CH$_3$;
R is CF$_3$, $R^2$ is Cl , $R^3$ and $R^4$ are joined to form —C(O)C(CH$_3$)$_2$O—, $R^5$ is OCHF$_2$, and $R^6$ is H;
R is CF$_3$, $R^2$ is Cl, $R^3$ and $R^6$ are H, $R^4$ is OCH(CH$_3$)$_2$, and $R^5$ is OCHF$_2$;
R is CF$_3$, $R^2$ is Cl , $R^3$ and $R^4$ are joined to form —CH$_2$C(CH$_3$)O—, $R^5$ is OCHF$_2$, and $R^6$ is H;
R is CF$_3$, $R^2$ and $R^5$ are Cl, $R^3$ and $R^6$ are H, and $R^4$ is OCH (CH$_3$)$_2$;
R is CF$_3$, $R^2$ and $R^5$ are Cl, $R^3$ and $R^4$ are joined to form —CH$_2$C(CH$_3$)$_2$O—, and $R^6$ is H;
R is CF$_3$, $R^2$ and $R^5$ are Cl, $R^3$ and $R^4$ are joined to form —C(O)C(CH$_3$)$_2$O—, and $R^6$ is H;

R is $CF_3$, $R^2$ and $R^5$ are Cl, $R^3$ and $R^6$ are H, and $R^4$ is $OCH=CH_2$.

The compounds of this invention may be prepared by following the procedures described below, or by methods analogous or similar thereto and within the skill of the art. These procedures are not intended to limit the scope of the appended Claims.

Method A

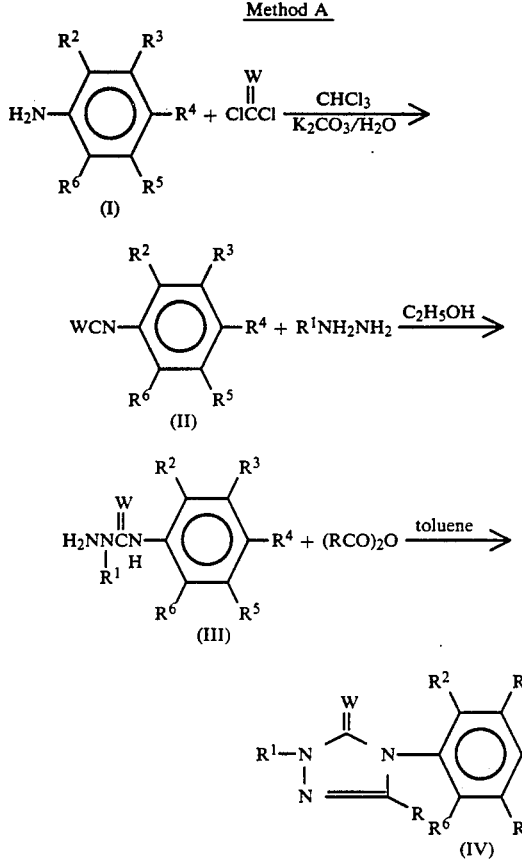

Following Method A, an appropriately substituted aniline (I) may be treated with thiophosgene (W=S) in chloroform in the presence of potassium carbonate and water to produce the substituted phenyl isothiocyanate, (II). Alternatively, aniline (I) may be treated with phosgene (W=O) in chloroform to produce the phenyl isocyanate, (II). The reaction of (II) with the appropriate hydrazine, e.g., methylhydrazine, in ethanol (for W=S) or toluene (W=O) produces the 4-(substituted-phenyl)-2-methyl-3-thiosemicarbazide, or -semicarbazide, (III). The treatment of (III) with the appropriate anhydride, e.g., trifluoroacetic anhydride, in toluene yields the corresponding 3-substituted-4,5-dihydro-1-methyl-4-(substituted-phenyl) -1,2,4-triazol-5(1H)-thione or -one, (IV).

Method B

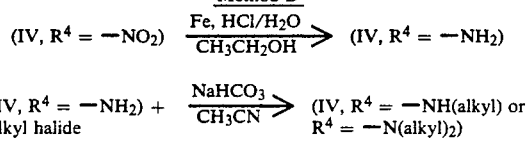

Following Method B, an appropriately substituted 4,5-dihydro-4-(nitrophenyl)-1,2,4-triazol-5(1H)-thione, (IV, $R^4$=—$NO_2$) may be reduced with iron powder in dilute hydrochloric acid and ethanol to produce the corresponding 4-aminophenyl-4,5-dihydro-1,2,4-triazol-5(1H)-thione, (IV, $R^4$=—$NH_2$). Subsequent reaction of (IV, $R^4$=—$NH_2$) with an alkyl halide, e.g., ethyl iodide, and sodium bicarbonate in acetonitrile produces appropriately substituted 4-(mono- and dialkyl aminophenyl)-4,5-dihydro-1,2,4-triazol-5(1H)-thione, (IV, $R^4$=—NH(alkyl) or $R^4$=—N(alkyl)$_2$).

Method C

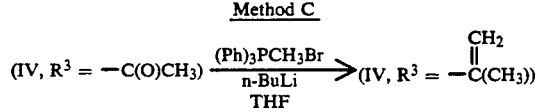

Following Method C, the reaction of appropriately substituted 4,5-dihydro-4-(3-methylcarbonylphenyl)-1,2,4-triazol-5(1H)-thione, (IV, $R^3$=—$C(O)CH_3$), with methyltriphenylphosphonium bromide and n-butyllithium in tetrahydrofuran produces the corresponding 4,5-dihydro-4-[3-(1-methylethenyl)phenyl]-1,2,4-triazol-5(1H)-thione, (IV, $R^3$=—$C(CH_3)=CH_2$).

Method D

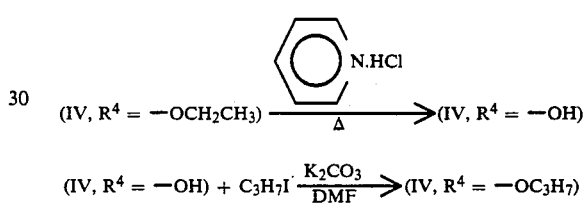

Following Method D, the treatment of an appropriately substituted 4-(ethoxyphenyl)-4,5-dihydro-1,2,4-triazol-5(1H)-thione, (IV, $R^4$=—$OCH_2CH_3$), with pyridine hydrochloride and heat produces the corresponding 4-(hydroxyphenyl)-4,5-dihydro-1,2,4-triazol-5(1H)-thione, (IV, $R^4$=—OH). The reaction of 4-(hydroxyphenyl)-4,5-dihydro-1,2,4-triazol-5(1H)-thione, (IV, $R^4$=—OH), with an alkyl halide, e.g., iodopropane, and potassium carbonate in N,N-dimethylformamide yields the corresponding 4,5-dihydro-4-(alkoxyphenyl)-1,2,4-triazol-5(1H)-thione, (IV, $R^4$=—$OC_3H_7$).

Method E

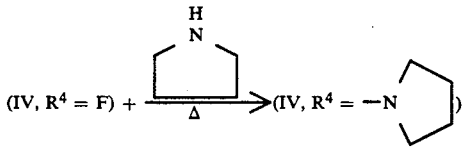

Following Method E, heating a mixture of an appropriately substituted compound, (IV, W=S, $R^4$=F), with a cyclic amino compound such as pyrrolidine, yields the corresponding 4,5-dihydro-4-(pyrrolidin-1-yl)-phenyl-1,2,4-thiazol-5(1H)-thione, (IV,

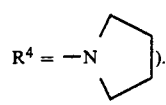

Method F (IV, R⁴ = —NH₂) $\xrightarrow[\text{H}_2\text{SO}_4,\ \text{H}_2\text{O}]{\text{NaNO}_2,\ \text{KI}}$ (IV, R⁴ + —I)

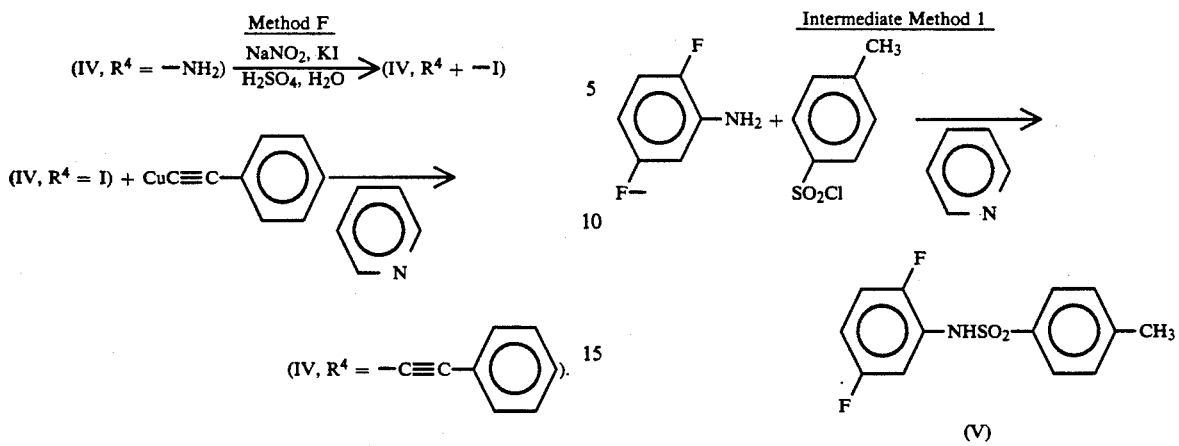

Intermediate Method 1

Following Method F, the reaction of an appropriately substituted 4-(aminophenyl)-4,5-dihydro-1,2,4-triazol-5(1H)-thione, (IV, R⁴=—NH₂, prepared as described in Method B) with sodium nitrite and potassium iodide in dilute sulfuric acid produces the corresponding 4-(iodophenyl)-4,5-dihydro-1,2,4-triazol-5(1H)-thione (IV, R⁴=I). Subsequent reaction of 4-(iodophenyl)-4,5-dihydro-1,2,4-triazol-5(1H)-thione, (IV, R⁴=I), with copper (I) phenylacetylide in pyridine yields the substituted 4-(phenylethynylphenyl)-4,5-dihydro-1,2,4-triazol-5(1H)-thione, (IV, R⁴=—C≡C—C₆H₅). The process described in this latter step is described in Stevens et al., *J. Org. Chem.*, Vol. 28, pp. 3313–3315 (1963).

Method G (IV, R⁴ = I) + Si(CH₃)₃≡CH $\xrightarrow[\text{CuI, TEA}]{\text{[(Ph)}_3\text{P]}_2\text{PdCl}_2}$ 
       CH₃CN (IV, R⁴ = —C≡CSi(CH₃)₃)

(IV, R⁴ = —C≡CSi(CH₃)₃) $\xrightarrow{(Bu)_4N^+F^-}{THF}$ (IV, R⁴ = —C≡CH)

Following Method G, the reaction of a substituted 4-(iodophenyl)-4,5-dihydro-1,2,4-triazol-5(1H)-thione, (IV, R⁴=I, prepared as described in Method F), with (trimethylsilyl) acetylene and a catalytic amount of bis-(triphenylphosphine) palladium (II) chloride and copper (I) iodide in a mixture of triethylamine and acetonitrile produces the substituted 4-(trimethylsilylethynylphenyl)-4,5-dihydro-1,2,4-triazol-5(1H)-thione (IV, R⁴=—C≡CSi(CH₃)₃). Treatment of the resultant compound, (IV, R⁴=—C≡CSi(CH₃)₃), with tetrabutylammonium fluoride in tetrahydrofuran yields the substituted 4-(ethynylphenyl)-4,5-dihydro-1,2,4-triazol-5(1H)-thione, (IV, R⁴=—C≡CH).

A variety of substituted aniline compounds (I) are commercially available. However, in those cases where an aniline starting material (I) having the desired substitutions is not available through commercial sources, one of the following processes may be employed.

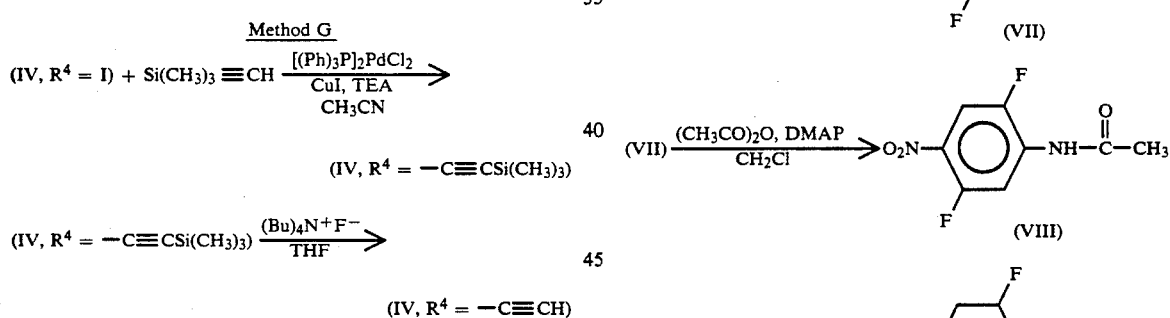

-continued
Intermediate Method 1

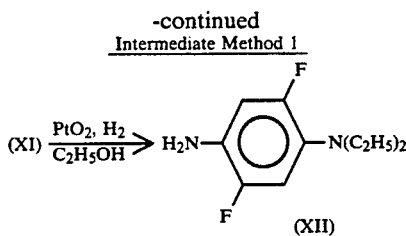

Following Intermediate Method 1, a substituted aniline, for example 2,5-difluoroaniline, may be reacted with 4-methylphenylsulfonyl chloride in pyridine to form N-(4-methylphenylsulfonyl)-2,5-difluoroaniline, (V). Nitration of (V) with sodium nitrite in nitric acid, acetic acid and water produces N-(4-methylphenylsulfonyl)-2,5-difluoro-4-nitroaniline, (VI). The reaction of (VI) with aqueous sulfuric acid yields 2,5-difluoro-4-nitroaniline, (VII). Subsequent reaction of (VII) with acetic anhydride and a small amount of dimethylaminopyridine (DMAP) in methylene chloride produces N-(2,5-difluoro-4-nitrophenyl)acetamide (VIII). Treatment of (VIII) with a borane/dimethyl sulfide complex in tetrahydrofuran yields N-ethyl-2,5-difluoro-4-nitroaniline, (IX). Repeating the previous two steps, the reaction of (IX) first with acetic anhydride (to produce N-(2,5-difluoro-4-nitrophenyl)-acetamide, (X)) followed by treatment with a borane/dimethyl sulfide complex yields N,N-diethyl-2,5-difluoro-4-nitroaniline, (XI). Hydrogenation of (XI) with platinum oxide in ethanol produces the desired 2,5-difluoro-4-diethylaminoaniline, (XII).

Intermediate Method 2

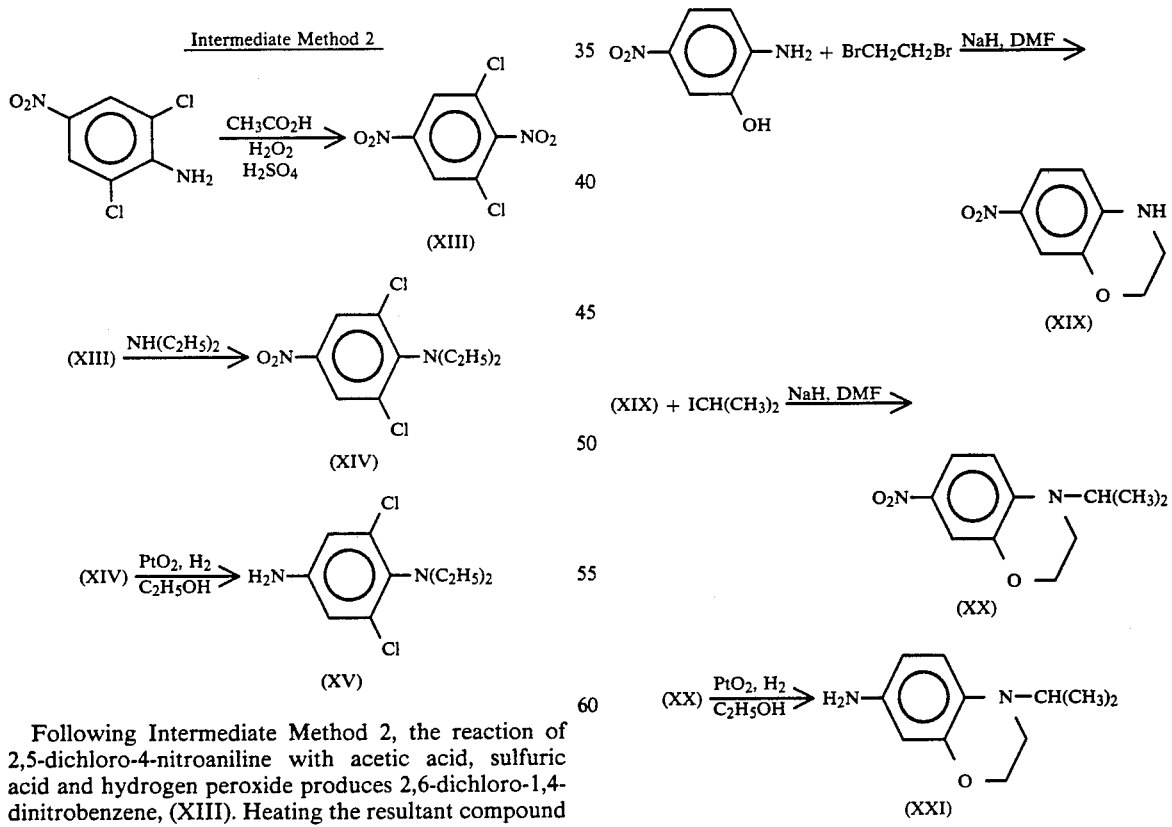

Following Intermediate Method 2, the reaction of 2,5-dichloro-4-nitroaniline with acetic acid, sulfuric acid and hydrogen peroxide produces 2,6-dichloro-1,4-dinitrobenzene, (XIII). Heating the resultant compound (XIII) in diethylamine produces 2,6-dichloro-4-nitrophenyl-N,N-diethylaniline, (XIV). Subsequent hydrogenation of (XIV) with platinum oxide in ethanol provides 3,5-dichloro-4-diethylaminoaniline, (XV).

Intermediate Method 3

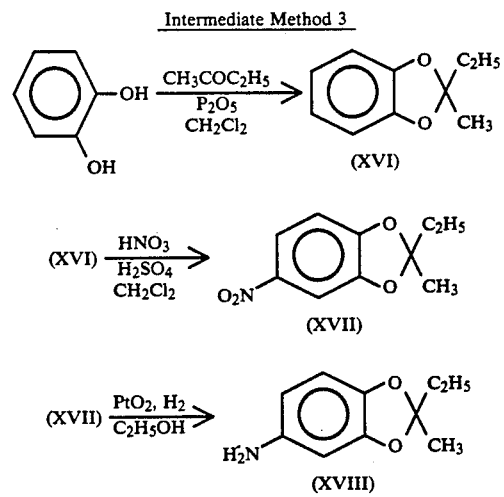

Following Intermediate Method 3, the reaction of catechol with 2-butanone and phosphorus pentoxide in methylene chloride produces 2-ethyl-2-methyl-1,3-benzodioxole, (XVI). Nitration of (XVI) with nitric and sulfuric acid in methylene chloride yields 2-ethyl-2-methyl-5-nitro-1,3-benzodioxole, (XVII). Subsequent hydrogenation of the compound (XVII) with platinum oxide in ethanol produces 5-amino-2-ethyl-2-methyl-1,3-benzodioxole, (XVIII).

Intermediate Method 4

Following Intermediate Method 4, the reaction of 2-hydroxy-4-nitroaniline with sodium hydride and 1,2-dibromoethane in N,N-dimethylformamide produces 2,3-dihydro-7-nitro-1,4-benzoxazine, (XIX). The reaction of (XIX) with sodium hydride and 2-iodopropane in N,N-dimethylformamide yields 2,3-dihydro-4-(1-methylethyl)-7-nitro-1,4-benzoxazine, (XX). Hydrogenation of (XX) with platinum oxide yielded (XXI).

Intermediate Method 5

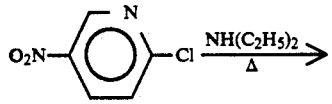

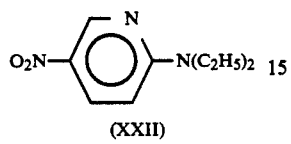

(XXII)

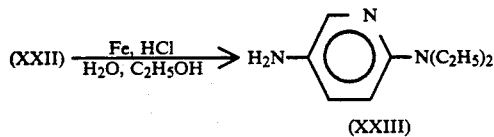

(XXIII)

Following Intermediate Method 5, the reaction of 2-chloro-5-nitropyridine, (XXII) with diethylamine produces 2-diethylamino-5-nitropyridine, (XXII). The reduction of this compound (XXII) with iron powder in aqueous hydrochloric acid and ethanol yields 5-amino-2-diethylaminopyridine, (XXIII).

Preparation of compounds of the invention is further illustrated by the following Examples. These Examples are not intended to limit the scope of the appended Claims.

EXAMPLE 1

4-(4-DIETHYLAMINOPHENYL)-3-TRI-FLUOROMETHYL-1-(2-HYDROXYETHYL)-4,5-DIHYDRO-1,2,4-TRIAZOL-5(1H)-THIONE

Step A
4-(4-Diethylaminophenyl)-2-(2-hydroxyethyl)-3-thiosemicarbazide

To a stirred solution of 5.0 g (0.024 mole) of 4-diethylaminophenyl isothiocyanate in 200 ml of ethanol was added 2.45 g (0.0290 mole) of 2-hydroxyethylhydrazine. The reaction mixture was stirred at room temperature for approximately 24 hours. The mixture was evaporated to dryness under reduced pressure to yield 7.3 g of a solid containing 4-(4-diethylaminophenyl)-2-(2-hydroxyethyl)-3-thiosemicarbazide. The nmr spectrum was consistent with the proposed structure contaminated with a small amount of 2-hydroxyethylhydrazine.

Step B 4-(4-Diethylaminophenyl)-3-trifluoromethyl-1-(2-hydroxyethyl)-4,5-dihydro-1,2,4-triazol-5(1H)-thione A solution of 3.0 g (0.010 mole) of 4-(4-diethylaminophenyl)-2-(2-hydroxyethyl)-3-thiosemicarbazide and 2.52 g (0.0120 mole) of trifluoroacetic anhydride in 250 ml of toluene was stirred at room temperature for approximately 24 hours. The reaction mixture was neutralized with an aqueous sodium bicarbonate solution. The aqueous phase was extracted with ethyl acetate, and the organic phases were combined. The combined organic phase was dried over anhydrous magnesium sulfate and was filtered. The filtrate was evaporated under reduced pressure, leaving a residue. This residue was purified by column chromatography to yield 0.5 g of 4-(4-diethylaminophenyl)-3-trifluoromethyl-1-(2-hydroxyethyl) -4,5-dihydro-1,2,4-triazol-5(1H)-thione as an oil, Compound 171 of Table 1. The nmr and mass spectra were consistent with the proposed structure.

EXAMPLE 2

4-(2-CHLORO-4-DIETHYLAMINOPHENYL)-3-TRIFLUOROMETHYL-4,5-DIHYDRO-1-METHYL-1,2,4-TRIAZOL-5(1H)-THIONE AND 4-(2-CHLORO-4-ETHYLAMINOPHENYL)-3-TRIFLUOROMETHYL-4,5-DIHYDRO-1-METHYL-1,2,4-TRIAZOL-5(1H)-THIONE

Step A
4-(2-chloro-4-nitrophenyl)-2-methyl-3-thiosemicarbazide

To a stirred solution of 60.0 g (0.280 mole) of 2-chloro-4-nitrophenyl isothiocyanate in 500 ml of ethanol was added 12.9 g (0.280 mole) of methylhydrazine. This mixture was heated and was stirred at 65° C. for approximately 18 hours. The mixture was then heated to reflux and was cooled. A solid had formed and was collected by filtration. The filter cake was rinsed with aqueous ethanol and was dried under reduced pressure to yield 59.0 g of 4-(2-chloro-4-nitrophenyl)-2-methyl-3-thiosemicarbazide, mp 164°–167° C. The nmr spectrum was consistent with the proposed structure.

Step B
4-(2-chloro-4-nitrophenyl)-3-trifluoromethyl-4,5-dihydro-1-methyl-1,2,4-triazol-5(1H)-thione To a stirred mixture of 58.6 g (0.225 mole) of 4-(2-chloro-4-nitrophenyl) -2-methyl-3-thiosemicarbazide in 250 ml of toluene was added 56.7 g (0.270 mole) of trifluoroacetic anhydride. The resulting slurry became exothermic to the point of reflux and was allowed to cool slowly to room temperature. This mixture was stirred at room temperature for approximately 18 hours during which time a solution formed. This organic solution was neutralized by washing with an aqueous 10% sodium hydroxide solution. The washed organic phase was dried over anhydrous magnesium sulfate and was filtered. The filtrate was evaporated under reduced pressure, leaving a residue. This residue was extracted with ethyl acetate, leaving 65.8 g of a solid. This solid was stirred in 900 ml of ethanol. The mixture was heated at reflux and then was filtered hot to remove insoluble material. The filtrate was allowed to cool slowly, and a small amount of water was added to the ethanol to initiate crystallization. The crystalline material was collected by filtration to yield 25.6 9 of 4-(2-chloro-4-nitrophenyl)-3-trifluoromethyl-4,5-dihydro-1-methyl-1, 2,4-triazol-5(1H)-thione, mp 152°–155° C., Compound 93 of Table 1. The nmr spectrum was consistent with the proposed structure. An additional 6.0 g of product was obtained by purification of the mother liquor by column chromatography.

Step C
4-(4-Amino-2-chlorophenyl)-3-trifluoromethyl-4,5-dihydro-1-methyl-1,2,4-triazol-5(1H)-thione To a stirred mixture of 18.8 g (0.0337 mole) of iron powder in 400 ml of concentrated hydrochloric acid, 20 ml of water, and 300 ml of ethanol was added slowly 28.5 g of 4-(2-chloro-4-nitrophenyl)-3-trifluoromethyl- 4,5-dihydro-1-methyl-1,2,4-triazol-5(1H)-thione. This mixture was heated at reflux for eight hours and then was cooled to room temperature and stirred for approximately 18 hours. The mixture was heated to reflux and was filtered hot. The filter cake was washed with methylene chloride. The wash and the filtrate were combined, and the solvents were removed by evaporation under reduced pressure, leaving a residue. This residue was purified by column chromatography on silica gel, eluting with diethyl ether to yield 23.4 g of 4-(4-amino-2-chlorophenyl)-3-trifluoromethyl-4,5-dihydro-1-methyl-1,2,4-triazol-5(1H)-thione as a solid, mp 145°–147° C., Compound 94 of Table 1. The nmr spectrum was consistent with the proposed structure.

Step D
4-(2-chloro-4-diethylaminophenyl)-3-trifluoromethyl-4,5-dihydro-1-methyl-1,2,4-triazol -5(1H)-thione and 4-(2-chloro-4-ethylaminophenyl)-3-trifluoromethyl-4,5-dihydro -1-methyl-1,2,4-triazol-5(1H)-thione To a stirred solution of 3.5 g (0.011 mole) of 4-(4-amino-2-chlorophenyl)-3-trifluoromethyl-4,5-dihydro-1-methyl-1,2,4-triazol-5(1H)-thione in a 100 ml of acetonitrile were added in succession 2.9 g (0.034 mole) of sodium bicarbonate and 3.7 g (0.024 mole) of iodoethane. The reaction mixture was heated at reflux for approximately 18 hours. An additional 1.8 g (0.011 mole) of iodoethane was added, and the reaction was stirred at room temperature for two days. The mixture was cooled, and the solvent was evaporated under reduced pressure, leaving a residue. Water was added to the residue, and the mixture was extracted with methylene chloride. The organic extract was dried over anhydrous magnesium sulfate and was filtered. The filtrate was evaporated under reduced pressure, leaving a residue. This residue was purified by column chromatography to produce two fractions. The first fraction yielded 0.5 g of 4-(2-chloro-4-diethylaminophenyl) -3-trifluoromethyl-4,5-dihydro-1-methyl-1,2,4-triazol-5(1H)-thione as a solid, mp 108°–110° C., Compound 98 of Table 1. The second fraction yielded 1.5 g of 4-(2-chloro-4-ethylaminophenyl)-3-trifluoromethyl-4,5-dihydro-1-methyl-1,2,4-triazol-5(1H)-thione as a solid, mp 87°–90° C., Compound 96 of Table 1.

EXAMPLE 3
3-TRIFLUOROMETHYL-4,5-DIHYDRO-1-METHYL-4-[3-(1-METHYLETHENYL)PHENYL]-1,2,4-TRIAZOL-5(1H)-THIONE

Step A
2-Methyl-4-(3-methylcarbonylphenyl)-3-thiosemicarbazide

Following procedures similar to those employed in Step A of Example 2, the reaction of 20.0 g (0.113 mole) of 3-methylcarbonylphenyl isothiocyanate and 5.21 g (0.113 mole) of methylhydrazine in 150 ml of ethanol yielded 19.9 g of 2-methyl-4-(3-methylcarbonylphenyl)-3-thiosemicarbazide as a solid, mp 125°–127° C. The nmr spectrum was consistent with the proposed structure.

Step B
3-Trifluoromethyl-4,5-dihydro-1-methyl-4-(3-methylcarbonylphenyl)-1,2,4-triazol-5(1H)-thione A mixture of 19.4 g (0.0871 mole) of 2-methyl-4-(3-methylcarbonylphenyl)-3-thiosemicarbazide and 36.6 g (0.174 mole) of trifluoroacetic anhydride in 150 ml of toluene was stirred at room temperature for approximately 18 hours. The reaction mixture was neutralized with an aqueous, 10% sodium hydroxide solution. The organic phase was dried over anhydrous magnesium sulfate and was filtered. The filtrate was evaporated under reduced pressure to yield 20.3 g of 3-trifluoromethyl-4,5-dihydro-1-methyl-4 -(3-methylcarbonylphenyl)-1,2,4-triazol-5(1H)-thione as a thick oil. The rlmr spectrum of the oil indicated that it contained about 65% of the desired product, the balance being reaction by-products.

Step C
3-Trifluoromethyl-4,5-dihydro-1-methyl-4-[3-(1-methylethenyl)phenyl]-1,2,4-triazol-5(1H)-thione Under a dry nitrogen atmosphere 23.8 ml of a 1.55M solution of n-butyllithium in hexane was added dropwise to a stirred solution of 15.8 g (0.0443 mole) of methyltriphenylphosphonium bromide in 300 ml of dry tetrahydrofuran. This mixture was stirred at room temperature for 2.5 hours, and a solution of 11.1 g of the oil from Step B in 50 ml of tetrahydrofuran was added dropwise. After complete addition, the reaction mixture was heated at reflux for 2.5 hours. The mixture was cooled to room temperature and was poured into 300 ml of an aqueous, 2N sodium hydroxide solution. This mixture was extracted with 300 ml of diethyl ether. The organic extract was dried over anhydrous magnesium sulfate and was filtered. The filtrate was evaporated under reduced pressure, leaving a residue. This residue was purified by column chromatography on silica gel eluting with ethyl acetate:n-heptane (25:75) to yield 3.7 g of 3-trifluoromethyl-4,5-dihydro-1-methyl-4-[3-(1-methylethenyl)phenyl]-1,2,4-triazol-5(1H)-thione as a solid, mp 64°–66° C., Compound 27 of Table 1.

EXAMPLE 4
3-TRIFLUOROMETHYL-4,5-DIHYDRO-1-METHYL-4-(4-n-PROPOXYPHENYL)-1,2,4-TRIAZOL-5(1H)-THIONE

Step A
4-(4-Ethoxyphenyl)-2-methyl-3-thiosemicarbazide

Following procedures similar to those employed in Step A of Example 2, the reaction of 2.5 g (0.0698 mole) of 4-ethoxyphenyl isothiocyanate and 3.22 g (0.0698 mole) of methylhydrazine in 100 ml of ethanol yielded 12.5 g of 4-(4-ethoxyphenyl)-2-methyl-3-thiosemicarbazide as a solid. The nmr spectrum was consistent with the proposed structure.

Step B
4-(4-Ethoxyphenyl)-3-trifluoromethyl-4,5-dihydro-1-methyl-1,2,4-triazol-5(1H)-thione Following procedures similar to those employed in Step B of Example 3, the reaction of 12.5 g (0.0530 mole) of 4-(4-ethoxyphenyl)-2-methyl-3-thiosemicarbazide with 11.2 g (0.0530 mole) of trifluoroacetic anhydride in 100 ml of toluene yielded 14.6 g of 4-(4-ethoxyphenyl)-3-trifluoromethyl-4,5-dihydro-1-methyl-1,2,4-triazol-5(1H)-thione as a solid, mp 93°–95° C., Compound 60 of Table 1. The nmr spectrum was consistent with the proposed structure.

Step C
3-Trifluoromethyl-4,5-dihydro-4-(4-hydroxyphenyl)-1-methyl-1,2,4-triazol-5(1H)-thione A mixture of 12.6 g (0.109 mole) of pyridine hydrochloride and 11.0 g (0.0363 mole) of 4-(4-ethoxyphenyl)-3-trifluoromethyl-4,5-dihydro-1-methyl-1,2,4-triazol-5(1H)-thione was heated at 215° C. and stirred for one hour. The mixture was cooled and dissolved in water. The aqueous solution was extracted with a mixture of tetrahydrofuran:diethyl ether (50:50). The organic phase was extracted with an aqueous, 10% sodium hydroxide solution. The basic extract was acidified, forming a precipitate. This solid was collected by filtration and dried to yield 7.1 g of 3-trifluoromethyl-4,5-dihydro-4-(4-hydroxyphenyl)-1-methyl-1,2,4-triazol-5(1H)-thione, mp 150°–152° C. The nmr spectrum was consistent with the proposed structure.

Step D
3-Trifluoromethyl-4,5-dihydro-1-methyl-4-(4-n-propoxyphenyl)-1,2,4-triazol-5(1H)-thione A stirred mixture of 1.5 g (0.0058 mole) of 3-trifluoromethyl-4,5-dihydro-4-(4-hydroxyphenyl)-1-methyl-1,2,4-triazol-5(1H)-one and 1.0 g (0.0069 mole) of potassium carbonate in 15 ml of N,N-dimethylformamide was heated at 80° C. While maintaining that temperature, 0.98 g (0.0058 mole) of 1-iodopropane was added. The reaction mixture was stirred at 80° C. for approximately 18 hours. The mixture was cooled and diluted with water. This mixture was extracted with chloroform. The extract was dried over anhydrous magnesium sulfate and was filtered. The filtrate was evaporated under reduced pressure, leaving a residue. The residue was purified by column chromatography on silica gel, eluting with methylene chloride, to yield 1.4 g of 3-trifluoromethyl-4,5-dihydro-1-methyl-4-(4-n-propoxyphenyl)-1,2,4-triazol-5(1H)-thione as a solid, mp 68°–70° C., Compound 61 of Table 1. The nmr spectrum was consistent with the proposed structure.

EXAMPLE 5
3-TRIFLUOROMETHYL-4,5-DIHYDRO-1-METHYL-4-(PYRROLIDIN-1-YL)PHENYL-1,2,4-TRIAZOL-5(1H)-THIONE

Step A
4-(4-Fluorophenyl)-2-methyl-3-thiosemicarbazide

Following procedures similar to those employed in Step A of Example 2, the reaction of 10.0 g (0.0653 mole) of 4-fluorophenyl isothiocyanate with 3.01 g (0.0654 mole) of methylhydrazine in 100 ml of ethanol yielded 10 g of 4-(4-fluorophenyl)-2-methyl-3-thiosemicarbazide as a solid, mp 148°–150° C. The nmr spectrum was consistent with the proposed structure.

Step B
4-(4-Fluorophenyl)-3-trifluoromethyl-4,5-dihydro-1-methyl-1,2,4-triazol-5-(1H)-thione Following procedures similar to those employed in Step B of Example 3, the reaction of 9.59 g (0.0480 mole) of 4-(4-fluorophenyl)-2-methyl-3-thiosemicarbazide with 10.1 g (0.0480 mole) of trifluoroacetic anhydride in 100 ml of toluene yielded 12.3 g of 4-(4-fluorophenyl)-3-trifluoromethyl-4,5-dihydro-1-methyl-1,2,4-triazol-5(1H) -thione as a solid, mp 94°–96° C., Compound 8 of Table 1. The nmr spectrum was consistent with the proposed structure.

Step C
3-Trifluoromethyl-4,5-dihydro-1-methyl-4-(pyrrolidin-1-yl)1,2,4-triazol-5-(1H)-thione A stirred mixture of 1.37 g (0.00490 mole) of 4-(4-fluorophenyl)-3-trifluoromethyl-4,5-dihydro-1-methyl-1,2,4-triazol-5(1H)-thione in 25 ml of pyrrolidine was heated at reflux for approximately 18 hours. The mixture was cooled, and most of the pyrrolidine was removed by distillation under reduced pressure, leaving a residue. This residue was partitioned between water and methylene chloride. The organic phase was dried over anhydrous magnesium sulfate and was filtered. The filtrate was evaporated under reduced pressure to yield 0.9 g of 3 trifluoromethyl-4,5-dihydro-1-methyl-4-(pyrrolidin-1-yl)phenyl-1,2,4-triazol-5(1H)-thione as a solid, mp 150°–153° C., compound 75 of Table 1.

EXAMPLE 6
3-TRIFLUOROMETHYL-4-[4-(3-TRIFLUOROMETHYL-1-METHYL-1,2,4-TRIAZOL-5-YL)PHENYL]-4,5-DIHYDRO-1-METHYL-1,2,4-TRIAZOL-5(1H)-THIONE AND 4-(4-CYANOPHENYL)-3-TRIFLUOROMETHYL-4,5-DIHYDRO-1-METHYL-1,2,4-TRIAZOL-5(1H)-THIONE

Step A
4(4-Cyanophenyl)-2-methyl-3-thiosemicarbazide

Following procedures similar to those employed in Step A of Example 2, the reaction of 7.8 g (0.049 mole) of 4-cyanophenyl isothiocyanate with 2.24 g (0.049 mole) of methylhydrazine in 50 ml of ethanol yielded 10.0 g of 4-(4-cyanophenyl)-2-methyl-3-thiosemicarbazide as a solid, mp 178°–179° C. The nmr spectrum was consistent with the proposed structure.

Step B
3-Trifluoromethyl-4-[4-(3-trifluoromethyl-1-methyl-1,2,4-triazol-5yl)phenyl]-4,5dihydro-1-methyl-1,2,4-triazol-5(1H)-thione and 4-(4-cyanophenyl)-3-trifluoromethyl-4,5-dihydro-1-methyl-1,2,4-triazol-5(1H)-thione A mixture of 5.2 g (0.025 mole) of 4-(4-cyanophenyl)-2-methyl-3-thiosemicarbazide and 5.3 g (0.025 mole) of trifluoroacetic anhydride in 100 ml of toluene was stirred at room temperature for approximately 18 hours. The reaction mixture was neutralized by washing with an aqueous sodium carbonate solution. The aqueous wash was extracted with toluene, and the organic phases were combined. The organic phase was dried over anhydrous magnesium sulfate and was filtered. The filtrate was evaporated under reduced pressure, leaving a residue. This residue was purified by column chromatography on silica gel, eluting with petroleum ether-:ethyl acetate (9:1). Two products were obtained by column chromatography: the first was 0.25 g of 4-(4-cyanophenyl)-3-trifluoromethyl-4,5-dihydro-1-methyl -1,2,4-triazol-5(1H)-thione, mp 60°–61° C., Compound 29 of Table 1; the second was 0.36 g of 3-trifluoromethyl-4-[4-(3-trifluoromethyl-1-methyl-1,2,4-triazol-5(1H)-thione, mp65°–66° C., Compound 79 of Table 1. The nmr spectra were consistent with the proposed structure.

EXAMPLE 7

4(2-CHLORO-4-PHENYLETHYNYLPHENYL)-3-TRIFLUOROMETHYL-4,5-DIHYDRO-1-METHYL-1,2,4-TRIAZOL-5-(1H)-THIONE

Step A 4-(2-chloro-4-iodophenyl)-3-trifluoromethyl-4,5-dihydro-1-methyl-1,2,4-triazol-5(1H)-thione To a stirred, warm (40° C.) solution of 10.8 g (0.0648 mole) of potassium iodide in 80 ml of water was added dropwise a solution of 10.0 g (0.0324 mole) of 4-(4-amino-2-chlorophenyl)-3-trifluoromethyl-4,5-dihydro-1-methyl-1,2,4triazol-5(1H)-thione (Compound 94 to Table 1, prepared in Step C of Example 2), 2.70 g (0.389 mole) of sodium nitrite, and 20.0 g (0.204 mole) of concentrated sulfuric acid in 125 g of ice-cold water. The resultant mixture was stirred at 40° C. for three hours. The mixture was cooled and was extracted with methylene chloride. The extract was washed with an aqueous sodium metabisulfite solution. The washed organic phase was dried over anhydrous magnesium sulfate and was filtered. The filtrate was evaporated under reduced pressure, leaving a residue. This residue was purified by column chromatography on silica gel, eluting with petroleum ether:diethyl ether (75:25) to yield 5.0 g of 4-(2-chloro-4iodophenyl)-3-trifluoromethyl -4,5-dihydro-1-methyl-1,2,4-triazol-5(1H)-thione as a solid, mp 117°-119° C., Compound 91 of Table 1. The nmr spectra were consistent with the proposed structure.

Step B 4-(2chloro-4-phenylethynylphenyl)-3-trifluoromethyl-4,5dihydro-1-methyl-1,2,4-triazol -5-(1H)-thione Using the process described by Steven, et al., (*J. Org. Chem.*, Vol. 28 pp. 3313—3315 (1963), the reaction of 4.6 g (0.011 mole) of 4-(2-chloro-4-iodophenyl)-3-trifluoromethyl-4,5-dihydro-1-methyl-1,2,4-triazol -5(1H), thione with 1.8 g (0.011 mole) of copper (I) phenylacetylide in 100 ml of dry pyridine under a dry nitrogen atmosphere produced 3.1 g of 4-(2-chloro-4-phenylethynylphenyl)-3-trifluoromethyl-4,5-dihydro-1-methyl-1,2,4-triazol-5(1H)-thione as a solid, mp 50°-53° C., Compound 92 of Table 1. The nmr and ir spectra were consistent with the proposed structure.

EXAMPLE 8

4-(4-ETHYNYL-2-METHYLPHENYL)-3-TRIFLUOROMETHYL-4,5-DIHYDRO-1-METHYL-1,2,4-TRIAZOL-5(1H)-THIONE

Step A 4-Iodo-2-methylphenyl isothiocyanate

To a stirred mixture of 9.9 g (0.086 mole) of thiophosgene, 5.0 g (0.036 mole) of potassium carbonate in 55 ml of water and 100 ml of chloroform was added a solution of 20.0 g (0.0862 mole) of 4-iodo-2-methylaniline in 50 ml of chloroform. Additional potassium carbonate was added to make the reaction mixture basic. An additional 9.9 g of thiophosgene was added, and the reaction mixture was stirred at room temperature for approximately 18 hours. The mixture was partitioned between water (100 ml) and chloroform (100 ml). The organic phase was dried over anhydrous magnesium sulfate and was filtered. The filtrate was evaporated under reduced pressure, leaving a residue. This residue was purified by column chromatography on silica gel, eluting with methylene chloride to yield 22.6 g of 4-iodo-2-methylphenyl iosthiocyante as a solid, mp 51°-53° C.

The ir spectrum was consistent with the proposed structure.

Step B 4-(4-Iodo-2-methylphenyl)-2-methyl-3-thiosemicarbazide

Following procedures similar to those employed in Step A of Example 2, the reaction of 22.3 g (0.0810 mole) of 4-iodo-2-methylphenyl isothiocyanate with 3.74 g (0.0811 mole) of methylhydrazine in 175 ml of ethanol yielded 16.7 g of 4-(4-iodo-2-methylphenyl)-2-methyl-3-thiosemicarbazide as a solid, mp 160°-161° C. The nmr spectrum was consistent with the proposed structure.

Step C

3-Trifluoromethyl-4,5-dihydro-4-(4-iodo-2-methylphenyl)-1-methyl-1,2,4-triazol-5(1H) -thione Following procedures similar to those employed in Step B of Example 3, the reaction of 16.4 g (0.0511 mole) of 4-(4-iodo-2-methylphenyl)-2-methyl-3-thiosemicarbazide with 11.8 g (0.0562 mole) of trifluoroacetic anhydride in 150 ml of toluene yielded 17.4 g of 3-trifluoromethyl-4,5-dihydro-1-methyl-4-(4-iodo-2-methylphenyl)-1,2,4-triazol-5(1H)-thione as a solid, mp 104°-107° C., Compound 106 of Table 1. The nmr spectrum was consistent with the proposed structure.

Step D

3-Trifluoromethyl-4,5-dihydro-1-methyl-4-(2-methyl-4-trimethylsilylethynylphenyl) -1,2,4-triazol-5(1H)-thione To a stirred mixture of 5.00 g (0.0125 mole) of 3-trifluoromethyl-4,51-dihydro-4-(4-iodo-2-methylphenyl)-1-methyl-1,2,4-triazol-5 (1H)-thione and 2.46 g (0.0250 mole) of trimethylsilylacetylene in 20 ml of acetonitrile and 100 ml of triethylamine was added 0.0880 g (0.000125 mole) of bis-(triphenylphosphine)palladium (II) chloride and 0.048 g (0.00025 mole) of copper (I) iodide. The reaction mixture was heated at reflux for approximately 18 hours. The solvents were removed from the reaction mixture by evaporation under reduced pressure, leaving a residue. This residue was dissolved in chloroform, and the organic solution was washed in succession with an aqueous, saturated sodium chloride solution and an aqueous, 20% ammonium chloride solution. The washed organic phase was evaporated under reduced pressure, leaving a dark oil. This oil was purified by column chromatography on silica gel, eluting with chloroform, to yield 4.7 g, of 3-trifluoromethyl-4,5-dihydro-1-methyl-4-(2-methyl-4-trimethylsilylethynylphenyl) -1,2,4-triazol-5(1H)-thione as a solid, mp 90°-93° C., Compound 113 of Table 1. The nmr spectrum was consistent with the proposed structure.

Step E 4-(4-ethynyl-2-methylphenyl)-3-trifluoromethyl-4,5-dihydro-1-methyl-1,2,4-triazol-5(1H)-thione To a stirred mixture of 4.40 g (0.0119 mole) of 3-trifluoromethyl-4,5-dihydro-1-methyl -4-(2-methyl-4-trimethylsilylethynylphenyl)-1,2,4-triazol-5-(1H)-
thione in 75 ml of tetrahydrofuran was added 10.8 g (0.0414 mole) of tetrabutylammonium fluoride. This mixture was stirred for about 20 minutes, and the reaction was partitioned between 75 ml of diethyl ether and 150 ml of an aqueous sodium chloride solution. The organic phase was dried over anhydrous magnesium sulfate and was filtered. The filtrate was evaporated under reduced pressure, leaving a residue. This residue was purified by column chromatography on silica gel, eluting with diethyl ether, to yield 2.5 g of 4-(4-ethynyl-2-methylphenyl)-3-trifluoromethyl-4,5-dihydro-1-methyl-1,2,4-triazol-5(1H)-thione as an oil, Compound 111 of Table 1. The nmr spectrum was consistent with the proposed structure.

EXAMPLE 9

4-(4-DIETHYLAMINO-2,5-DIFLUOROPHENYL)-3-TRIFLUOROMETHYL-4,5-DIHYDRO-1-METHYL-1,2,4-TRIAZOL-5(1H)-THIONE

Step A N-(4-Methylphenylsulfonyl)-2,5-difluoroaniline

A stirred mixture of 15.0 g (0.116 mole) of 2,5-difluoroaniline and 24.4 g (0.128 mole) of 4-methylphenylsulfonyl chloride in 50 ml of pyridine was heated at reflux for approximately 18 hours. The reaction mixture was cooled and poured into 500 ml of 6N hydrochloric acid. This acidic mixture was allowed to stand at room temperature for two days. A precipitate formed and was collected by filtration. The filter cake was washed with dilute hydrochloric acid and was dried under reduced pressure to yield 25.0 g of N-(4-methylphenylsulfonyl)-2,5-difluoroaniline. The nmr spectrum was consistent with the proposed structure.

Step B
N-(4-Methylphenylsulfonyl)-2,5-difluoro-4-nitroaniline

The nitration of 12.0 g (0.042 mole) of N-(4-methylphenylsulfonyl)-2,5-difluoroaniline with 0.2 g (0.0035 mole) of sodium nitrite and 17.4 g (0.276 mole) of fuming nitric acid in 86 ml of glacial acetic acid and 86 ml of water yielded 12.2 g of N-(4-methylphenylsulfonyl)-2,5-difluoro-4-nitroaniline as a solid. The nmr spectrum was consistent with the proposed structure.

Step C 2,5-Difluoro-4-nitroaniline

To a stirred mixture of 12.2 g (0.0370 mole) of N-(4-methylphenylsulfonyl)-2,5-difluoro-4-nitroaniline in 20 ml of water was added 70 ml of concentrated sulfuric acid. This mixture was heated at 90° C. for 15 minutes and then was allowed to cool and stir at room temperature for five days. The reaction mixture was poured into ice-water, and the aqueous mixture was neutralized with concentrated ammonium hydroxide. The resulting solid was collected by filtration. The filter cake was washed with water and was dried under reduced pressure to yield 6.15 g of 2,5-difluoro-4-nitroaniline. The nmr spectrum was consistent with the proposed structure.

Step D N-(2,5-Difluoro-4-nitrophenyl)acetamide

A mixture of 6.0 g (0.034 mole) of 2,5-difluoro-4-nitroaniline, 6.5 g (0.064 mole) of acetic anhydride, and approximately 0.1 g (0.0008 mole) of dimethylaminopyridine in 300 ml of methylene chloride was stirred and heated at reflux for two hours. The reaction mixture was allowed to cool and stir at room temperature for approximately 18 hours. The solvent was removed from the mixture by distillation under reduced pressure, leaving a residue. To this residue was added 32.5 g (0.318 mole) of acetic anhydride and several drops of concentrated sulfuric acid. This mixture was stirred at room temperature for approximately 18 hours. Approximately 300 ml of water was added to the mixture causing a vigorous exotherm and a solid to form. This solid was collected by filtration. The filter cake was washed with water and was dried under reduced pressure to yield 6.5 g of N-(2,5-difluoro-4-nitrophenyl)acetamide. The nmr spectrum was consistent with the proposed structure.

Step E N-Ethyl-2,5-difluoro-4-nitroaniline

To a cold (0°C.), stirred solution of 6.3 g (0.029 mole) of N-(2,5-difluoro-4-nitrophenyl)acetamide in 100 ml of dry tetrahydrofuran was added dropwise 8.8 ml of a 10M boranedimethyl sulfide complex in tetrahydrofuran. The reaction mixture was heated until a gentle reflux was maintained with no external heating. When this reflux subsided, the mixture was reheated at reflux for three hours. The reaction mixture was cooled to 0° C., and methanol was added dropwise until no gas evolution was seen upon subsequent addition. This mixture was allowed to stand at room temperature for two days. The solvent was removed from the mixture by distillation under reduced pressure, leaving a residue. This residue was purified by column chromatography on silica gel, eluting with methylene chloride to yield 5.6 g of N-ethyl-2,5-difluoro-4-nitroaniline as a solid. The nmr spectrum was consistent with the proposed structure.

Step F
N-Ethyl-N-(2,5-difluoro-4-nitrophenyl)acetamide

To a stirred mixture of 5.4 g (0.027 mole) of N-ethyl-2,5-difluoro-4-nitroaniline in 100 ml of acetic anhydride was added three drops of concentrated sulfuric acid. This mixture was stirred at room temperature for 30 minutes, and was poured into 200 ml of ice and water. The aqueous mixture was extracted with three portions of ethyl acetate. The extracts were combined and washed in succession with an aqueous, saturated sodium chloride solution and water. The washed organic phase was dried over anhydrous magnesium sulfate and was filtered. The filtrate was evaporated under reduced pressure to yield 6.1 g of N-ethyl-N-(2,5-difluoro-4-nitrophenyl)acetamide as a solid. The nmr spectrum was consistent with the proposed structure.

Step G N,N-Diethyl-2,5-difluoro-4-nitroaniline

Following procedures similar to those employed in Step E of this Example, the reaction of 4.2 g (0.017 mole) of N-ethyl-N-(2,5-difluoro-4-nitrophenyl)acetamide with 5.1 ml of a 10M borane dimethyl sulfide complex in tetrahydrofuran in 100 ml of dry tetrahydrofuran yielded 3.6 g of N,N-diethyl-2,5-difluoro-4-nitroaniline. The nmr spectrum was consistent with the proposed structure.

Step H 4-Diethylamino-2,5-difluoroaniline

Hydrogenation of 3.4 g (0.015 mole) of N,N-diethyl-2,5-difluoro-4-nitroaniline with approximately 0.1 g (0.0004 mole of platinum in 250 ml of ethanol yielded 3.0 g of 4-diethyl-amino-2,5-difluoroaniline. The nmr spectrum was consistent with the proposed structure.

Step I 4-Diethylamino-2,5-difluorophenyl isothiocyanate

In a manner similar to Step A of Example 8, the reaction of 3.0 g (0.026 mole) of thiophosgene with 2.6 g (0.013 mole) of 4-diethylamino-2,5-difluoroaniline and 7.2 g (0.052 mole) of potassium carbonate in 100 ml of chloroform and 100 ml of water yielded 3.2 g of 4-diethylamino-2,5-difluorophenyl isothiocyanate. The nmr and ir spectra were consistent with the proposed structure.

Step J
4-(4-Diethylamino-2,5-difluorophenyl)-2-methyl-3-thiosemicarbazide Following procedures similar to those employed in Step A of Example 2, the reaction of 2.9 g (0.012 mole) of 4-diethylamino-2,5-difluorophenyl isothiocyanate with 0.55 g (0.012 mole) of methylhydrazine in 75 ml of ethanol yielded 3.4 g of 4-(4-diethylamino-2,5-difluorophenyl) -2-methyl-3-thiosemicarbazide. The nmr spectrum was consistent with the proposed structure.

Step K
4-(4-Diethylamino-2,5-difluorophenyl)-3-trifluoromethyl-4,5-dihydro-1-methyl-1,2,4-triazol-5(1H)-thione Following procedures similar to those employed in Step B of Example 3, the reaction of 3.1 g (0.011 mole) of 4-(4-diethylamino-2,5-difluorophenyl) -2-methyl-3-thiosemicarbazide with 2.3 g (0.011 mole) of trifluoroacetic anhydride in 50 ml of toluene yielded 2.3 g of 4-(4-diethylamino-2,5-difluorophenyl)-3-trifluoromethyl-4,5-dihydro-1-methyl-1,2,4-triazol-5(1H)-thione, Compound 138 of Table 1. The nmr spectrum was consistent with the proposed structure.

EXAMPLE 10
4-(3,5-DICHLORO-4-ETHYLAMINOPHENYL)-3-TRIFLUOROMETHYL-4,5-DIHYDRO -1-METHYL-1,2,4-TRIAZOL-5(1H)-THIONE

Step A 2,6-Dichloro-1,4-dinitrobenzene

A stirred mixture of 15.0 g (0.0725 mole) of 2,6-dichloro-4-nitroaniline in 300 ml of glacial acetic acid, 90 ml of hydrogen peroxide (30% aqueous solution), and 6 ml of concentrated sulfuric acid was heated at 100° C. for 3.5 hours, and then an additional 90 ml of hydrogen peroxide (30%) was added. The reaction mixture was cooled and was diluted with 600 ml of water. A solid formed and was collected by filtration. The filter cake was washed in succession with concentrated sulfuric acid and concentrated hydrochloric acid. The washed solid was dissolved in diethyl ether, and the organic solution was neutralized by washing with an aqueous, 10% sodium hydroxide solution. The organic phase was dried-over anhydrous magnesium sulfate and was filtered. The filtrate was evaporated under reduced pressure, leaving a residue. This residue was purified by column chromatography on silica gel, eluting with ethyl acetate:petroleum ether (25:75) to yield 9.1 g of 2,6-dichloro-1,4-dinitrobenzene, mp 109°–112° C. The nmr spectrum was consistent with the proposed structure.

Step B 2,6-Dichloro-N,N-diethyl-4-nitroaniline

A stirred mixture of 4.5 g (0.019 mole) of 2,6-dichloro-1,4-dinitrobenzene in 75 ml of diethylamine was heated at reflux for two days. The reaction mixture was cooled, and the solvent was removed by distillation under reduced pressure, leaving a residue. The residue was partitioned between water and diethyl ether. The organic phase was dried over anhydrous magnesium sulfate and was filtered. The filtrate was evaporated under reduced pressure, leaving a residue. This residue was purified by column chromatography on silica gel, eluting with methylene chloride, to yield 3.7 g of 2,6-dichloro-N,N-diethyl-4-nitroaniline. The nmr spectrum was consistent with the proposed structure.

Step C 3,5-Dichloro-4-diethylaminoaniline

The hydrogenation of 3.7 g (0.014 mole) of 2,6-dichloro-N,N-diethyl-4-nitroaniline with approximately 0.1 g (0.0004 mole) of platinum-oxide in 250 ml of ethanol yielded 1.9 g of 3,5-dichloro-4-diethylaminoaniline as an oil. The nmr spectrum was consistent with the proposed structure.

Step D 3,5-Dichloro-4-diethylaminophenyl isothiocyanate

Following procedures similar to those employed in Step A of Example 8, the reaction of 1.9 g (0.0082 mole) of 3,5-dichloro-4-diethylaminoaniline with 1.88 g (0.0163 mole) of thiophosgene and 5.0 g (0.036 mole) of potassium carbonate in 20 ml of water and 100 ml of chloroform yielded 2.2 g of 3,5-dichloro-4-diethylaminophenyl isothiocyanate as an oil. The ir spectrum was consistent with the proposed structure.

Step E
4-(3,5-Dichloro-4-diethylaminophenyl)-2-methyl-3-thiosemicarbazide Following procedures similar to those employed in Step A of Example 2, the reaction of 2.2 g (0.0080 mole) of 3,5-dichloro-4-diethylaminophenyl isothiocyanate with 0.37 g (0.0080 mole) of methylhydrazine in 75 ml of ethanol produced a quantitative yield of 4-(3,5-dichloro-4-diethylaminophenyl)-2-methyl-3-thiosemicarbazide. The nmr spectrum was consistent with the proposed structure.

Step F
4-(3,5-Dichloro-4-diethylaminophenyl)-3-trifluoromethyl-4,5-dihydro-1-methyl-1,2,4-triazol-5(1H)-thione Following procedures similar to those employed in Step B of Example 3, the reaction of 2.6 g (0.0080 mole) of 4-(3,5-dichloro-4-diethylaminophenyl) -2-methyl-3-thiosemicarbazide with 2.0 g (0.0096 mole) of trifluoroacetic anhydride in 75, ml of toluene yielded 1.0 g of 4-(3,5-dichloro-4-diethylaminophenyl)-3-trifluoromethyl -4,5-dihydro-1-methyl-1,2,4-triazol-5(1H)-thione as a solid, mp 128°–130° C., Compound 151 of Table 1. The nmr and mass spectra were consistent with the proposed structure.

EXAMPLE 11
4-(2-ETHYL-2-METHYL-1,3-BENZODIOXOL-5-YL)-3-TRIFLUOROMETHYL-4,5-DIHYDRO-1-METHYL-1,2,4-TRIAZOL-5(1H)-THIONE

Step A 2-Ethyl-2-methyl-1,3-benzodioxole

To a stirred solution of 20.0 g (0.180 mole) of catechol and 0.8 g (0.40 mole) of 2-butanone in 200 ml of methylene chloride was added 128.0 g (0.902 mole) of phosphorus pentoxide. The reaction mixture was stirred at room temperature for two days. The stirring was stopped, and the reaction solids were allowed to settle. The reaction mixture was decanted into a separatory funnel. The solid material was washed with methylene chloride, and the wash was decanted into the above separatory funnel. The combined organic phase was washed with aqueous, saturated sodium bicarbonate solution. The washed organic phase was dried over anhydrous magnesium sulfate and was filtered. The filtrate was evaporated under reduced pressure to yield 17.3 g of 2-ethyl-2-methyl-1,3-benzodioxole.

Step B 2-Ethyl-2-methyl-5-nitro-1,3-benzodioxole

The nitration of 16.5 g (0.100 mole) of 2-ethyl-2-methyl-1,3-benzodioxole with 7.7 ml of nitric acid (70% solution in water) and 10 ml of concentrated sulfuric acid in 100 ml of methylene chloride yielded 2.6 g of 2-ethyl-2-methyl-5-nitro-1,3-benzodioxole. The nmr spectrum was consistent with the proposed structure.

Step C 5-Amino-2-ethyl-2-methyl-1,3-benzodioxole

The hydrogenation of 2.55 g (0.0120 mole) of 2-ethyl-2-methyl-5-nitro-1,3-benzodioxole with 0.3 g (0.0013 mole) of platinum oxide in 100 ml of ethanol yielded 2.0 g of 5-amino-2-ethyl-2-methyl-1,3-benzodioxole as an oil. The nmr spectrum was consistent with the proposed structure.

Step D (2-Ethyl-2-methyl-1,3-benzodioxol-5-yl) isothiocyanate

Using procedures similar to those employed in Step A of Example 8, the reaction of 1.9 g (0.011 mole) of 5-amino-2-ethyl-2-methyl-1,3-benzodioxole with 2.4 g (0.021 mole) of thiophosgene and 6.2 g (0.045 mole) of potassium carbonate in 10 ml of water and 70 ml of chloroform yielded 2.3 g of (2-ethyl-2-methyl-1,3-benzodioxol-5-yl) isothiocyanate as an oil. The nmr spectrum was consistent with the proposed structure.

Step E
4-(2-Ethyl-2-methyl-1,3-benzodioxol-5-yl)-2-methyl-3-thiosemicarbazide

Following procedures similar to those employed in Step A of Example 2, the reaction of 2.1 g (0.0095 mole) of (2-ethyl-2-methyl-1,3-benzodioxol-5-yl) isothiocyanate with 0.44 g (0.0095 mole) of methylhydrazine in 50 ml of ethanol yielded 1.7 g of 4-(2-ethyl-2-methyl-1,3-benzodioxol-5-yl)-2-methyl-3-thiosemicarbazide as a solid. The nmr spectrum was consistent with the proposed structure.

Step F
4-(2-Ethyl-2-methyl-1,3-benzodioxol-5-yl)-3-trifluoromethyl-4,5-dihydro-1-methyl-1,2,4-triazol-5(1H)-thione Following procedures similar to those employed in Step B of Example 3, the reaction of 1.5 g (0.0056 mole) of 4-(2-ethyl-2-methyl-1,3-benzodioxol-5-yl)-2-methyl-3-thiosemicarbazide with 1.3 g (0.0062 mole) of trifluoroacetic anhydride in 75 ml of toluene yielded 1.3 g of 4-(2-ethyl-2-methyl-1,3-benzodioxol-5-yl)-3-trifluoromethyl-4,5-dihydro-1-methyl-1,2,4-triazol-5(1H)-thione as a gummy solid, Compound 162 of Table 1. The nmr and mass spectra were consistent with the proposed structure.

EXAMPLE 12

4-[2,3-DIHYDRO-4-(1-METHYLETHYL)-1,4-BENZOXAZIN-7-YL)-3-TRIFLUOROMETHYL-4,5-DIHYDRO-1-METHYL-1,2,4-TRIAZOL-5(1H)-THIONE

Step A 2,3-Dihydro-7-nitro-1,4-benzoxazine

Under a dry nitrogen atmosphere a solution of 41.0 g (0.270 mole) of 2-amino-5-nitrophenol in 250 ml of N,N-dimethylformamide was added dropwise to a stirred mixture of 6.48 g (0.270 mole) of sodium hydride in 250 ml of N,N-dimethylformamide. When the evolution of gas ceased, 50.0 g (0.270 mole) of 1,2-dibromothane was added dropwise, and the resulting mixture was stirred at room temperature for approximately 18 hours. The reaction mixture was diluted with water, and this mixture was extracted several times with methylene chloride. The organic extracts were combined and washed with several portions of an aqueous, 10% sodium hydroxide solution. The washed organic phase was filtered through a pad of silica gel. The filtrate was evaporated under reduced pressure to yield 3.8 g of 2,3-dihydro-7-nitro-1,4-benzoxazine. The nmr spectrum indicated a small amount of N,N-dimethylformamide was present in the product.

Step B
2,3-Dihydro-4-(1-methylethyl)-7-nitro-1,4-benzoxazine

Under a dry nitrogen atmosphere, a solution of 3.7 g (0.020 mole) of 2,3-dihydro-7-nitro-1,4-benzoxazine in 50 ml of N,N-dimethylformamide was added to a stirred solution of 0.60 g (0.025 mole) of sodium hydride in 100 ml of N,N-dimethylformamide. Upon cessation of hydrogen evolution, 3.4 g (0.020 mole) of 2-iodopropane was added. The reaction mixture was stirred at room temperature for approximately 18 hours, then was heated at 65° C. for 24 hours, and finally was heated at 80° C. for 24 hours. The reaction mixture was cooled and diluted with water. The aqueous mixture was extracted with ethyl acetate. The extract was dried over anhydrous magnesium sulfate and was filtered. The filtrate was evaporated under reduced pressure, leaving a residue. Analysis of this residue by nmr spectroscopy indicated it was a mixture of 2,3-dihydro-4-(1-methylethyl)-7-nitro-1,4-benzoxazine and 2,3-dihydro-7-nitro-1,4-benzoxazine.

Step C
7-Amino-2,3-dihydro-4-(1-methylethyl)-1,4-benzoxazine

The hydrogenation of 1.2 g of the mixture from Step B with approximately 0.1 g (0.0004 mole) of platinum oxide in 250 ml of ethanol produced an oil. Analysis of this oil by nmr spectroscopy indicated that it contained a mixture of 7-amino-2,3-dihydro-4-(1-methylethyl)-1,4-benzoxazine and 7-amino-2,3-dihydro-1,4-benzoxazine.

Step D 2,3
Dihydro-4-(1-methylethyl)-1,4-benzoxazin-7-yl isothiocyanate

Following procedures similar to those employed in Step A of Example 8, the reaction of 1.0 g of the mixture from Step C with 1.2 g (0.010 mole) of thiophosgene and 2.9 g (0.029 mole) of potassium carbonate in 100 ml of water and 100 ml of chloroform yielded 1.3 g of a residue. Analysis of this residue by nmr spectroscopy indicated that it contained a mixture of 2,3-dihydro-4-(1-methylethyl)-1,4-benzoxazin-7-yl isothiocyanate and 2,3-dihydro-1,4-benzoxazin-7-yl isothiocyanate.

Step E
4-[2,3-Dihydro-4-(1-methylethyl)-1,4-benzoxazin-7-yl]-2-methyl-3-thiosemicarbazide Following procedures similar to those employed in Step A of Example 2, the reaction of 1.3 g of the mixture from Step D with 0.25 g (0.0056 mole) of methylhydrazine in 250 ml of ethanol yielded 1.7 g of a solid. Analysis of this solid by nmr spectroscopy indicated that it contained a mixture of 4-[2,3-dihydro-4-(1-methylethyl)-1,4-benzoxazin-7-yl]-2-methyl-3-thiosemicarbazide and 4-(2,3-dihydro-1,4-benzoxazin-7-yl)-2-methyl-3-thiosemicarbazide.

Step F
4-[2,3-Dihydro-4-(1-methylethyl)-1,4-benzoxazin-7-yl]-3-trifluoromethyl-4,5-dihydro-1-methyl-1,2,4-triazol-5(1H)-thione Following procedures similar to those employed in Step B of Example 3, the reaction of 1.7 g of the mixture from Step E with 1.27 g (0.00606 mole of trifluoroacetic anhydride in 500 ml of toluene produce a reside. Purification of this residue by column chromatography yielded 0.3 g of 4-[2,3-dihydro-4-(1-methylethyl)-1,4-benzoxazine-7-yl]-3-trifluoromethyl-4,5-dihydro-1-methyl-1,2,4-triazol-5(1H)-thione as an oil, Compound 164 of Table 1. The nmr spectrum was consistent with the proposed structure.

EXAMPLE 13

4-(2-DIETHYLAMINOPYRIDIN-5-YL)-3-TRIFLUOROMETHYL-4,5-DIHYDRO-1-METHYL-1,2,4-TRIAZOL-5(1H)-THIONE

Step A 2-Diethylamino-5-nitropyridine

A stirred mixture of 27.6 g (0.174 mole) of 2-chloro-5-nitropyridine in 500 ml of diethylamine was heated at reflux for two days. The excess diethylamine was removed by distillation under reduced pressure, leaving a residue. This residue was dissolved in methylene chloride, and the organic solution was washed with an aqueous, 10% sodium hydroxide solution. The washed organic phase was dried over anhydrous magnesium sulfate and was filtered. The filtrate was evaporated under reduced pressure to yield 33.2 g of 2-diethylamino-5-nitropyridine as a solid. The nmr spectrum was consistent with the proposed structure.

Step B 5-Amino-2-diethylaminopyridine

Following procedures similar to those disclosed in Artland, et al., *J. Heterocyclic Chem.*, Vol. 14, 129-134 (1977), the reaction of 10.0 g (0.0512 mole) of 2-diethylamino-5-nitropyridine with 147.0 g (0.659 mole) of tin (II) chloride dehydrate in diethyl ether and concentrated hydrochloric acid produced a residue. This reaction was repeated, and the residues were combined, giving a total of 20 g. The combined residue was purified by column chromatography on silica gel, eluting with acetone to yield 16.2 g of 5-amino-2-diethylaminopyridine as an oil. The nmr spectrum was consistent with the proposed structure.

Step C (2-Diethylaminopyridin-5-yl) isothiocyanate

Using procedures similar to those employed in Step A of Example 8, the reaction of 15.9 g (0.096 mole of 5-amino-2-diethylaminopyridine with 22.2 g (0.193 mole) of thiophosgene and 5.0 g (0.036 mole) of potassium carbonate in 50 ml of water and 150 ml of chloroform yielded 3.8 g of (2-diethylaminopyridin-5-yl) isothiocyanate as a solid. The nmr spectrum was consistent with the proposed structure.

Step D
4-(2-Diethylaminopyridin-5-yl)-2-methyl-3-thiosemicarbazide

Following procedures similar to those employed in Step A of Example 2, the reaction of 3.5 g (0.017 mole) of (2-diethyl-aminopyridin-5-yl) isothiocyanate with 0.86 (0.019 mole) of methylhydrazine in 150 ml of ethanol yielded 2.5 g of 4-(2-diethylaminopyridin-5-yl)-2-methyl-3-thiosemicarbazide as a solid, mp 147°-149° C. The nmr spectrum was consistent with the proposed structure.

Step E
4-(2-Diethylaminopyridin-5-yl)-3-trifluoromethyl-4,5-dihydro-1-methyl-1,2,4-triazol-5(1H)-thione Following procedures similar to those employed in Step B of Example 3, the reaction of 2.25 g (0.00890 mole) of 4-(2-diethylaminopyridin-5-yl)-2-methyl-3-thiosemicarbazide with 1.9 g (0.0089 mole) of trifluoroacetic anhydride in 200 ml of toluene yielded 1.3 g of 4-(2-diethylaminopyridin-5-yl)-3-trifluoromethyl-4,5-dihydro-1-methyl-1,2,4-triazol-5(1H)-thione as a solid, mp 96°-98° C., Compound 182 of Table 1. The nmr and mass spectra were consistent with the proposed structure.

EXAMPLE 14

4-(4-BROMO-2-METHYLPHENYL)-3-TRIFLUOROMETHYL-4,5-DIHYDRO-1-METHYL-1,2,4-TRIAZOL-5(1H)-ONE

Step A
4-(4-Bromo-2-methylphenyl)-2-methyl-3-semicarbazide

Following procedures similar to those employed in Step A of Example 2, the reaction of 10.0 g (0.0472 mole) of 4-bromo-2-methylphenyl isocyanate with 2.17 g (0.0472 mole) of methylhydrazine in 150 ml of tetrahydrofuran yielded 7.36 g of 4-(4-bromo-2-methylphenyl)-2-methyl-3-semicarbazide as a solid, m.p. 127°-128° C. The nmr spectrum was consistent with the proposed structure.

Step B
4-(4-Bromo-2-methylphenyl)-3-trifluoromethyl-4,5-dihydro-1-methyl-1,2,4-triazol-5(1H)-one Following procedures similar to those employed in Step B of Example 3, the reaction of 0.06 g (0.274 mole) of 4-(4-bromo-2-methylphenyl)-2-methyl-3-semicarbazide with 5.75 g (0.0274 mole) of trifluoroacetic anhydride in 100 ml of toluene yielded 4.6 g of 4-(4-bromo-2-methylphenyl)-3-trifluoromethyl-4,5-dihydro-1-methyl-1,2,4-triazol-5(1H)-one as a solid, mp 80°-83° C., Compound 198 of Table 1. The nmr spectrum was consistent with the proposed structure.

Representative compounds of the invention are set forth in Table 1. Identifying properties for these compounds are found in Table 2. The compounds are identified in Table 2 by numbers which correspond to the Compound Numbers assigned in Table 1.

The substituted-phenyl-1,2,4-triazol-5(1H)-thiones and -ones disclosed herein are useful for controlling undesired plant growth. To demonstrate this activity, representative compounds underwent pre- and post-emergence evaluations using a variety of broadleaf and grasseous crops and weeds. The results of these evaluations are shown in Tables 3 and 4. The compounds are identified in Tables 3 and 4 by numbers which correspond to the Compound Numbers assigned in Table 1. The plant test species used in demonstrating the herbicidal activity of this invention included cotton (*Gossypium hirsutum* var. Stoneville), soybean (*Glycine max* var. Williams), lima bean (*Phaseolus lunatus* L.), field corn (Zea mays var. Agway 425x or PN3732), rice (*Oryza sativa* var. Labelle), wheat (*Triticum aestivium* var. Wheaton), field bindweed (*Convolvulus arvensis*), morningglory (*Ipomoea lacunosa* or *Ipomoea hederacea*) (reported as "Gloryspp" in Tables 3 and 4), velvetleaf (*Abutilon theophrasti*) (reported as "Velvetlf" in Tables 3 and 4), wild oat (*Avena fatua*), barnyardgrass (*Echinochloa crus-galli*) (reported as "Barnydgr" in Tables 3 and 4), green foxtail (*Setaria viridis*) (reported as "Foxgreen" in Tables 3 and 4), johnsongrass (*Sorghum halepense*) (reported as "Johngr" in Tables 3 and 4), tomato (*Lycolpersicon esculentum*), and wild mustard (*Brassica kaber*) (reported as "Mustwild" in Tables 3 and 4).

To prepare a stock solution for testing, 0.48 gram of a compound of the invention was weighed into a flask and then dissolved in 60 ml of an aqueous acetone solution (water:acetone, 50:50) containing 0.5% (v/v) of sorbitan monolaurate emulsifier/solubilizer. Upon dissolution, the 60 ml solution was divided into two 30 ml portions, each portion being equivalent to 8.0 kg/ha when sprayed onto four 15 cm×25 cm test flats. One 30 ml portion was set aside for future use. The second portion was diluted with an additional 30 ml of the aqueous acetone/emulsifier solution to provide 60 ml of a-4.0 kg/ha solution. A 30 ml portion of this solution was diluted in the same manner as described above to provide 60 ml of a 2.0 kg/ha solution. Successive serial dilutions were made to provide test solutions for the remaining application rates. The test flats consisted of disposable fiber flats, 8 cm×15 cm×25 cm, which were filled to a depth of approximately 6.5 cm with steam sterilized sandy loam soil. The soil was leveled and impressed with a template to provide evenly spaced furrows 13 cm long and 0.5 cm deep in each flat. Seeds of the crops or weeds -were planted in the furrows, one species per furrow, and the template was again employed to firmly press the seeds into place. A topping soil of equal portions of sand and sandy loam soil was placed uniformly on top of each flat to a depth of approximately 0.5 cm.

For postemergence testing, the flats were planted with the test species 8 to 11 days prior to treatment. The various dilutions of the compounds of the invention were then sprayed directly onto the soil surface of the two preemergence test flats, on the foliage of the two postemergence test flats. The treated flats were maintained in a greenhouse for two weeks prior to evaluation for herbicidal activity.

Herbicidal data at application rates equivalent to 8.0 kilograms/hectare (kg/ha) and/or submultiples thereof, i.e., 4.0 kg/ha and 2.0 kg/ha, are given for various compounds of the invention in Table 3 (preemergence activity)-and Table 4 (postemergence activity). In some instances in Tables 3 and 4, the data is reported as percent kill (% K), and in other instances, the data is reported in the Tables as percent control (% C).

Percent kill, as reported in Tables 3 and 4, denotes the percentage of plants killed following application of the compounds of the invention.

Percent control, as also reported in Tables 3 and 4, is determined by a method similar to the 0 to 100 rating system disclosed in "Research Methods in Weed Science", 2nd ed., B. Truelove, ed., Southern Weed Science society, Auburn university, Auburn, Alabama, 1977. The rating system is as follows:

| Herbicide Rating System | | | |
|---|---|---|---|
| Rating Percent Control | Description of Main Categories | Crop Description | Weed Description |
| 0 | No effect | No crop reduction or injury | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery doubtful | Deficient to moderate weed control |
| 60 | | Lasting crop injury, no recovery | Moderate weed control |
| 70 | | Heavy injury and stand loss | Control somewhat less than satisfactory |
| 80 | Severe | Crop nearly destroyed, a few survivors | Satisfactory to good weed control |
| 90 | | Only occasional live plants left | Very good to excellent control |
| 100 | Complete effect | Complete crop destruction | Complete weed destruction |

In Tables 3 and 4, no entry means that the compounds were not tested against the particular plant species.

Compounds 25, 120, 121, 202, and 203 were not tested in pre- or postemergence evaluations (Tables 3 and 4) due to insufficient quantities of test compound.

For use in herbicidal applications, the active compounds may be, if desired, formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use, the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1% to 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Other possible wettable powder formulations are:

| Component: | % by Wt. |
|---|---|
| Active ingredient | 40.00 |
| Sodium lignosulfonate | 20.00 |
| Attapulgite clay | 40.00 |
| Total | 100.00 |
| Active ingredient | 90.00 |
| Dioctyl sodium sulfosuccinate | 0.10 |
| Synthetic fine silica | 9.90 |
| Total | 100.00 |
| Active ingredient | 20.00 |
| Sodium alkylnaphthalenesulfonate | 4.00 |
| Sodium lignosulfonate | 4.00 |
| Low viscosity methyl cellulose | 3.00 |
| Attapulgite clay | 69.00 |
| Total | 100.00 |
| Active ingredient | 25.00 |
| Base: | 75.00 |
| 96% hydrated aluminum magnesium silicate | |
| 2% powdered sodium lignosulfonate | |
| 2% powdered anionic sodium alkyl-naphthalenesulfonate | |
| Total | 100.00 |

Frequently, additional wetting agent and/or oil will be added to the tank-mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

The following are examples of emulsifiable contrate formulations which may be used in herbicidal applications:

| Component: | % by Wt. |
|---|---|
| Active ingredient | 53.01 |
| Blend of alkylnaphthalenesulfonate and polyoxyethylene ethers | 6.00 |
| Epoxidized soybean oil | 1.00 |
| Xylene | 39.99 |
| Total | 100.00 |
| Active ingredient | 10.00 |
| Blend of alkylnaphthalenesulfonate and polyoxyethylene ethers | 4.00 |
| Xylene | 86.00 |
| Total | 100.00 |

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are examples of flowable formulations which may be used in herbicidal applications:

| Component: | % by Wt. |
|---|---|
| Active ingredient | 46.00 |
| Colloidal magnesium aluminum silicate | 0.40 |
| Sodium alkylnaphthalenesulfonate | 2.00 |
| Paraformaldehyde | 0.10 |
| Water | 40.70 |
| Propylene glycol | 7.50 |
| Acetylenic alcohols | 2.50 |
| Xanthan gum | 0.80 |
| Total | 100.00 |
| Active ingredient | 45.00 |
| Water | 48.50 |
| Purified smectite clay | 2.00 |
| Xanthan gum | 0.50 |
| Sodium alkylnaphthalenesulfonate | 1.00 |
| Acetylenic alcohols | 3.00 |
| Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively non-volatile solvent such as water, corn oil, kerosene, propylene glycol, or other suitable solvents. The following illustrate specific suspensions which may be useful in herbicidal applications.

| | % by Wt. |
|---|---|
| Oil Suspension: | |
| Active ingredient | 25.00 |
| Polyoxyethylene sorbitol hexaoleate | 5.00 |
| Highly aliphatic hydrocarbon oil | 70.00 |
| Total | 100.00 |

|  | % by Wt. |
| --- | --- |
| Aqueous Suspension: | |
| Active ingredient | 40.00 |
| Polyacrylic acid thickener | 0.30 |
| Dodecylphenol polyethylene glycol ether | 0.50 |
| Disodium phosphate | 1.00 |
| Monosodium phosphate | 0.50 |
| Polyvinyl alcohol | 1.00 |
| Water | 56.70 |
| Total | 100.00 |

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon TM fluorinated hydrocarbons, may also be used. Water-soluble or water dispersible granules are also useful formulations for herbicidal application of the present compounds. Such granular formulations are free-flowing, non-dusty, and readily water-soluble or water-miscible. The soluble or dispersible granular formulations described in U.S. Pat No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

In addition, the active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; the amount may be as low as, e.g., about 1 to about 50 g/ha, preferably about 4 to 30 g/ha. For field use, where there are losses of herbicide, higher application rates (e.g., four times the rates mentioned above) may be employed.

The active herbicidal compounds of this invention may be used in combination with other herbicides, e.g., they may be mixed with, for example, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl-N-(2-methoxy-1-methylethyl)acetamide (metolachlor), and N-chloroacetyl-N-(2,6-diethylphenyl)glycine (diethatyl-ethyl) benzothiadiazinone herbicides such as 3-(1-methylethyl)-(1H)-2,1,3-benzothiadiazin-4-(3H)-one-2,2-dioxide (bentazon); triazine herbicides such as 6-chloro-N-ethyl-N-(1-methylethyl)-1,3,5-triazine-2,4-diamine (atrazine), and 2-[4-chloro-6-(ethylamino)-1,3,5-triazin-2-yl) amino-2-methylpropanenitrile (cyanazine); dinitroaniline herbicides such as 2,6-dinitro-N,N-dipropyl-4-(trifluoromethyl) benzeneamine (trifluralin); aryl urea herbicides such as N'-(3,4-dichlorophenyl)-N,N-dimethylurea (diuron) and N,N-dimethyl-N'-[3-(trifluoromethyl)phenylurea (fluo-meturon); and 2-[(2-chlorophenyl)methyl-4,4-dimethyl-3-isoxazolidinone.

As will be apparent to those skilled in the art, various modifications may be made in the formulations and application of the compounds of this invention without departing from the inventive concepts herein as defined in the claims.

Tables 1 through 4 follow. These Tables set forth representative compounds of the invention and identify various properties thereof, including the herbicidal utility of these compounds.

TABLE 1

NOVEL 4-(SUBSTITUTED ARYL)-4,5-DIHYDRO-1,2,4-TRIAZOL-5(1H)-THIONES

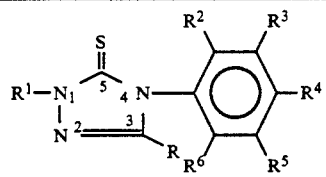

| Cmpd. No. | R | R¹ | R² | R³ | R⁴ | R⁵ | R⁶ |
| --- | --- | --- | --- | --- | --- | --- | --- |
| 1 | H | CH₃ | H | H | Cl | H | H |
| 2 | CH₃ | CH₃ | H | H | Cl | H | H |
| 3 | CH₃ | CH₂C₆H₅ | H | H | Cl | H | H |
| 4 | CCl₃ | CH₃ | H | H | Cl | H | H |
| 5 | CF₃ | CH₃ | H | H | H | H | H |
| 6 | CF₃ | CH₃ | F | H | H | H | H |
| 7 | CF₃ | CH₃ | H | F | H | H | H |
| 8 | CF₃ | CH₃ | H | H | F | H | H |
| 9 | CF₃ | CH₃ | Cl | H | H | H | H |
| 10 | CF₃ | CH₃ | H | Cl | H | H | H |
| 11 | CF₃ | CH₃ | H | H | Cl | H | H |
| 12 | CF₃ | CH₃ | Br | H | H | H | H |
| 13 | CF₃ | CH₃ | H | Br | H | H | H |
| 14 | CF₃ | CH₃ | H | H | Br | H | H |
| 15 | CF₃ | CH₃ | H | I | H | H | H |
| 16 | CF₃ | CH₃ | CH₃ | H | H | H | H |
| 17 | CF₃ | CH₃ | H | CH₃ | H | H | H |
| 18 | CF₃ | CH₃ | H | H | CH₃ | H | H |

TABLE 1-continued

NOVEL 4-(SUBSTITUTED ARYL)-4,5-DIHYDRO-1,2,4-TRIAZOL-5(1H)-THIONES

| # | | | | | | | |
|---|---|---|---|---|---|---|---|
| 19 | CF$_3$ | CH$_3$ | H | H | CH$_2$CH$_3$ | H | H |
| 20 | CF$_3$ | CH$_3$ | H | H | CH(CH$_3$)$_2$ | H | H |
| 21 | CF$_3$ | CH$_3$ | CF$_3$ | H | H | H | H |
| 22 | CF$_3$ | CH$_3$ | H | CF$_3$ | H | H | H |
| 23 | CF$_3$ | CH$_3$ | H | H | CF$_3$ | H | H |
| 24 | CF$_3$ | CH$_3$ | C≡CH | H | H | H | H |
| 25 | CF$_3$ | CH$_3$ | H | C≡CH | H | H | H |
| 26 | CF$_3$ | CH$_3$ | C≡CSi(CH$_3$)$_3$ | H | H | H | H |
| 27 | CF$_3$ | CH$_3$ | H | C(CH$_3$)=CH$_2$ | H | H | H |
| 28 | CF$_3$ | CH$_3$ | H | CN | H | H | H |
| 29 | CF$_3$ | CH$_3$ | H | H | CN | H | H |
| 30 | CF$_3$ | CH$_3$ | NO$_2$ | H | H | H | H |
| 31 | CF$_3$ | CH$_3$ | H | NO$_2$ | H | H | H |
| 32 | CF$_3$ | CH$_3$ | H | H | NO$_2$ | H | H |
| 33 | CF$_3$ | CH$_3$ | NH$_2$ | H | H | H | H |
| 34 | CF$_3$ | CH$_3$ | H | NH$_2$ | H | H | H |
| 35 | CF$_3$ | CH$_3$ | H | H | NH$_2$ | H | H |
| 36 | CF$_3$ | CH$_3$ | H | NH(CH$_3$) | H | H | H |
| 37 | CF$_3$ | CH$_3$ | H | H | NH(CH$_2$CH$_3$) | H | H |
| 38 | CF$_3$ | CH$_3$ | H | H | NH(C$_6$H$_5$) | H | H |
| 39 | CF$_3$ | CH$_3$ | H | H | NH(COCH$_3$) | H | H |
| 40 | CF$_3$ | CH$_3$ | H | N(CH$_3$)$_2$ | H | H | H |
| 41 | CF$_3$ | CH$_3$ | H | H | N(CH$_3$)$_2$ | H | H |
| 42 | CF$_3$ | CH$_3$ | H | H | N(CH$_2$CH$_3$)$_2$ | H | H |
| 43 | CF$_3$ | CH$_3$ | H | H | N(CH$_2$CH$_3$)$_2$·HCl | H | H |
| 44 | CF$_3$ | CH$_3$ | H | H | N(CH$_2$CH$_3$)(CH$_2$CH$_2$F) | H | H |
| 45 | CF$_2$CF$_2$CF$_3$ | CH$_3$ | H | H | N(CH$_2$CH$_3$)$_2$ | H | H |
| 46 | CON(CH$_3$)$_2$ | CH$_3$ | H | H | N(CH$_2$CH$_3$)$_2$ | H | H |
| 47 | CF$_3$ | CH$_3$ | H | H | N(n-C$_3$H$_7$)$_2$ | H | H |
| 48 | CF$_3$ | CH$_3$ | H | H | N(CH$_3$)(n-C$_3$H$_7$) | H | H |
| 49 | CF$_3$ | CH$_3$ | H | H | N(CH$_3$)[CH(CH$_3$)$_2$] | H | H |
| 50 | CF$_3$ | CH$_3$ | H | H | N(CH$_2$CH$_3$)(CH$_2$CF$_3$) | H | H |
| 51 | CF$_3$ | CH$_3$ | H | H | N(CH$_3$)(C$_6$H$_4$,4-F) | H | H |
| 52 | CF$_3$ | CH$_3$ | H | N$^+$(CH$_3$)$_4$I$^-$ | H | H | H |
| 53 | CF$_3$ | CH$_3$ | H | OH | H | H | H |
| 54 | CF$_3$ | CH$_3$ | H | H | OH | H | H |
| 55 | CF$_3$ | CH$_3$ | OCH$_3$ | H | H | H | H |
| 56 | CF$_3$ | CH$_3$ | H | OCH$_3$ | H | H | H |
| 57 | CF$_3$ | CH$_3$ | H | H | OCH$_3$ | H | H |
| 58 | CF$_3$ | CH$_3$ | H | OCH(CH$_3$)$_2$ | H | H | H |
| 59 | CF$_3$ | CH$_3$ | H | H | OCH(CH$_3$)$_2$ | H | H |
| 60 | CF$_3$ | CH$_3$ | H | H | OCH$_2$CH$_3$ | H | H |
| 61 | CF$_3$ | CH$_3$ | H | H | O(CH$_2$)$_2$CH$_3$ | H | H |
| 62 | CF$_3$ | CH$_3$ | H | H | O(CH$_2$)$_3$CH$_3$ | H | H |
| 63 | CF$_3$ | CH$_3$ | H | O(CH$_2$)$_4$CH$_3$ | H | H | H |
| 64 | CF$_3$ | CH$_3$ | H | H | O(CH$_2$)$_4$CH$_3$ | H | H |
| 65 | CF$_3$ | CH$_3$ | H | H | OC$_6$H$_5$ | H | H |
| 66 | CF$_3$ | CH$_3$ | H | H | OC$_6$H$_4$,4-F | H | H |
| 67 | CF$_3$ | CH$_3$ | H | H | OCH$_2$C$_6$H$_5$ | H | H |
| 68 | CF$_3$ | CH$_3$ | H | H | SCH$_3$ | H | H |
| 69 | CF$_3$ | CH$_3$ | H | H | SO$_2$CH$_3$ | H | H |
| 70 | CF$_3$ | CH$_3$ | H | H | CH$_2$C$_6$H$_5$ | H | H |
| 71 | CF$_3$ | CH$_3$ | H | C(O)CH$_3$ | H | H | H |
| 72 | CF$_3$ | CH$_3$ | H | H | C(O)CH$_3$ | H | H |
| 73 | CF$_3$ | CH$_3$ | H | C(O)C$_6$H$_5$ | H | H | H |
| 74 | CF$_3$ | CH$_3$ | H | H | C(O)C$_6$H$_5$ | H | H |
| 75 | CF$_3$ | CH$_3$ | H | H | 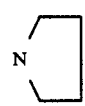 | H | H |
| 76 | CF$_3$ | CH$_3$ | H | H | 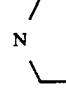 | H | H |
| 77 | CF$_3$ | CH$_3$ | H | H | 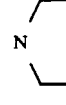 | H | H |

TABLE 1-continued
NOVEL 4-(SUBSTITUTED ARYL)-4,5-DIHYDRO-1,2,4-TRIAZOL-5(1H)-THIONES

| No. | | | | | | | |
|---|---|---|---|---|---|---|---|
| 78 | CF$_3$ | CH$_3$ | [1-methyl-5-(trifluoromethyl)pyrazol-3-yl] | H | H | H | H |
| 79 | CF$_3$ | CH$_3$ | H | H | [1-methyl-5-(trifluoromethyl)pyrazol-3-yl] | H | H |
| 80 | CF$_3$ | CH$_3$ | Cl | Cl | H | H | H |
| 81 | CF$_3$ | CH$_3$ | Cl | H | Cl | H | H |
| 82 | CF$_3$ | CH$_3$ | F | H | Cl | H | H |
| 83 | CF$_3$ | CH$_3$ | F | H | F | H | H |
| 84 | CF$_3$ | CH$_3$ | Cl | H | H | Cl | H |
| 85 | CF$_3$ | CH$_3$ | F | H | H | F | H |
| 86 | CF$_3$ | CH$_3$ | Cl | H | H | H | Cl |
| 87 | CF$_3$ | CH$_3$ | F | H | H | H | F |
| 88 | CF$_3$ | CH$_3$ | H | Cl | Cl | H | H |
| 89 | CF$_3$ | CH$_3$ | H | H | H | Cl | H |
| 90 | CF$_3$ | CH$_3$ | Cl | H | Br | H | H |
| 91 | CF$_3$ | CH$_3$ | Cl | H | I | H | H |
| 92 | CF$_3$ | CH$_3$ | Cl | H | C≡CC$_6$H$_5$ | H | H |
| 93 | CF$_3$ | CH$_3$ | Cl | H | NO$_2$ | H | H |
| 94 | CF$_3$ | CH$_3$ | Cl | H | NH$_2$ | H | H |
| 95 | CF$_3$ | CH$_3$ | Cl | H | NH(CH$_3$) | H | H |
| 96 | CF$_3$ | CH$_3$ | Cl | H | NH(CH$_2$CH$_3$) | H | H |
| 97 | CF$_3$ | CH$_3$ | Cl | H | N(CH$_3$)$_2$ | H | H |
| 98 | CF$_3$ | CH$_3$ | Cl | H | N(CH$_2$CH$_3$)$_2$ | H | H |
| 99 | CF$_3$ | CH$_3$ | H | Cl | CH$_3$ | H | H |
| 100 | CF$_3$ | CH$_3$ | CH$_3$ | Cl | H | H | H |
| 101 | CF$_3$ | CH$_3$ | CH$_3$ | H | Cl | H | H |
| 102 | CF$_3$ | CH$_3$ | CH$_3$ | H | H | Cl | H |
| 103 | CF$_3$ | CH$_3$ | CH$_3$ | H | H | H | Cl |
| 104 | CF$_3$ | CH$_3$ | CH$_3$ | H | F | H | H |
| 105 | CF$_3$ | CH$_3$ | CH$_3$ | H | Br | H | H |
| 106 | CF$_3$ | CH$_3$ | CH$_3$ | H | I | H | H |
| 107 | CF$_3$ | CH$_3$ | CH$_3$ | CH$_3$ | H | H | H |
| 108 | CF$_3$ | CH$_3$ | CH$_3$ | H | CH$_3$ | H | H |
| 109 | CF$_3$ | CH$_3$ | CH$_3$ | H | H | CH$_3$ | H |
| 110 | CF$_3$ | CH$_3$ | CH$_3$ | H | H | H | CH$_3$ |
| 111 | CF$_3$ | CH$_3$ | CH$_3$ | H | C≡CH | H | H |
| 112 | CF$_3$ | CH$_3$ | CH$_3$ | H | C≡CC$_6$H$_5$ | H | H |
| 113 | CF$_3$ | CH$_3$ | CH$_3$ | H | C≡CSi(CH$_3$)$_3$ | H | H |
| 114 | CF$_3$ | CH$_3$ | H | CH$_3$ | CH$_3$ | H | H |
| 115 | CF$_3$ | CH$_3$ | H | CH$_3$ | H | CH$_3$ | H |
| 116 | CF$_3$ | CH$_3$ | CF$_3$ | H | NH[C(O)C$_6$H$_5$] | H | H |
| 117 | CF$_3$ | CH$_3$ | NO$_2$ | H | F | H | H |
| 118 | CF$_3$ | CH$_3$ | NO$_2$ | H | Cl | H | H |
| 119 | CF$_3$ | CH$_3$ | NO$_2$ | H | Br | H | H |
| 120 | CF$_3$ | CH$_3$ | NO$_2$ | H | CF$_3$ | H | H |
| 121 | CF$_3$ | CH$_3$ | NO$_2$ | H | NH[C(O)CH$_3$] | H | H |
| 122 | CF$_3$ | CH$_3$ | NH$_2$ | H | F | H | H |
| 123 | CF$_3$ | CH$_3$ | NH$_2$ | H | Cl | H | H |
| 124 | CF$_3$ | CH$_3$ | NH[C(O)CH$_3$] | H | Cl | H | H |
| 125 | CF$_3$ | CH$_3$ | NH[C(O)C$_6$H$_5$] | H | F | H | H |
| 126 | CF$_3$ | CH$_3$ | OH | H | NO$_2$ | H | H |
| 127 | CF$_3$ | CH$_3$ | OH | H | OH | H | H |
| 128 | CF$_3$ | CH$_3$ | OH | H | OCH$_2$CH$_3$ | H | H |
| 129 | CF$_3$ | CH$_3$ | OCH$_3$ | H | NO$_2$ | H | H |
| 130 | CF$_3$ | CH$_3$ | OC(S)N(CH$_3$)$_2$ | H | NO$_2$ | H | H |
| 131 | CF$_3$ | CH$_3$ | OCH$_3$ | H | OCH$_3$ | H | H |
| 132 | CF$_3$ | CH$_3$ | OCH$_2$CH$_3$ | H | OCH$_2$CH$_3$ | H | H |
| 133 | CF$_3$ | CH$_3$ | SCH$_3$ | H | NO$_2$ | H | H |
| 134 | CF$_3$ | CH$_3$ | SC(O)N(CH$_3$)$_2$ | H | NO$_2$ | H | H |
| 135 | CF$_3$ | CH$_3$ | Cl | Cl | Cl | H | H |
| 136 | CF$_3$ | CH$_3$ | Cl | H | Cl | Cl | H |
| 137 | CF$_3$ | CH$_3$ | F | H | Cl | F | H |
| 138 | CF$_3$ | CH$_3$ | F | H | N(CH$_2$CH$_3$)$_2$ | F | H |
| 139 | CF$_3$ | CH$_3$ | F | H | N(CH$_2$CH$_3$)[C(O)CH$_3$] | F | H |
| 140 | CF$_3$ | CH$_3$ | Cl | H | N(CH$_2$CH$_3$)$_2$ | Cl | H |

TABLE 1-continued
NOVEL 4-(SUBSTITUTED ARYL)-4,5-DIHYDRO-1,2,4-TRIAZOL-5(1H)-THIONES

| 141 | CF$_3$ | CH$_3$ | F | H | OCH$_3$ | Cl | H |
| 142 | CF$_3$ | CH$_3$ | Cl | H | OCH$_3$ | Cl | H |
| 143 | CF$_3$ | CH$_3$ | Cl | H | OCH(CH$_3$)$_2$ | Cl | H |
| 144 | CF$_3$ | CH$_3$ | Cl | H | Cl | H | Cl |
| 145 | CF$_3$ | CH$_3$ | F | H | N(CH$_2$CH$_3$)$_2$ | H | F |
| 146 | CF$_3$ | CH$_3$ | H | Cl | Cl | Cl | H |
| 147 | CF$_3$ | CH$_3$ | H | F | Cl | F | H |
| 148 | CF$_3$ | CH$_3$ | H | Cl | OCH(CH$_3$)$_2$ | Cl | H |
| 149 | CF$_3$ | CH$_3$ | H | Cl | NH[(CH$_2$)$_3$CH$_3$] | Cl | H |
| 150 | CF$_3$ | CH$_3$ | H | Cl | N(CH$_3$)$_2$ | Cl | H |
| 151 | CF$_3$ | CH$_3$ | H | Cl | N(CH$_2$CH$_3$)$_2$ | Cl | H |
| 152 | CF$_3$ | CH$_3$ | H | F | OCH(CH$_3$)$_2$ | F | H |
| 153 | CF$_3$ | CH$_3$ | H | F | N(CH$_3$)(CH$_2$CH$_3$) | F | H |
| 154 | CF$_3$ | CH$_3$ | H | Cl | N(CH$_2$CH$_2$CH$_3$)$_2$ | Cl | H |
| 155 | CF$_3$ | CH$_3$ | CH$_3$ | H | CH$_3$ | CH$_3$ | H |
| 156 | CF$_3$ | CH$_3$ | CH$_3$ | H | CH$_3$ | H | CH$_3$ |
| 157 | CF$_3$ | CH$_3$ | H | CH$_3$ | CH$_3$ | CH$_3$ | H |
| 158 | CF$_3$ | CH$_3$ | H | OCH$_3$ | OCH$_3$ | OCH$_3$ | H |
| 159 | CF$_3$ | CH$_3$ | NO$_2$ | H | F | (CH$_2$)$_3$CH$_3$ | H |
| 160 | CF$_3$ | CH$_3$ | H | —OCH$_2$O— | | H | H |
| 161 | CF$_3$ | CH$_3$ | H | —CH$_2$C(CH$_3$)$_2$O— | | H | H |
| 162 | CF$_3$ | CH$_3$ | H | —OC(CH$_3$)(CH$_2$CH$_3$)O— | | H | H |
| 163 | CF$_3$ | CH$_3$ | H | —N(CH$_2$CH$_3$)CH$_2$CH$_2$N(CH$_2$CH$_3$)— | | H | H |
| 164 | CF$_3$ | CH$_3$ | H | —OCH$_2$CH$_2$N[CH(CH$_3$)$_2$]— | | H | H |
| 165 | CF$_3$ | CH$_3$ | H | —OCH$_2$CH$_2$O— | | H | H |
| 166 | CF$_3$ | CH$_2$CH$_3$ | H | H | N(CH$_2$CH$_3$)$_2$ | H | H |
| 167 | CF$_3$ | CH(CH$_3$)$_2$ | H | H | N(CH$_2$CH$_3$)$_2$ | H | H |
| 168 | CF$_3$ | CH$_2$CH$_2$OH | H | H | H | H | H |
| 169 | CF$_3$ | CH$_2$CH$_2$OH | H | H | Cl | H | H |
| 170 | CF$_3$ | CH$_2$CH$_2$OH | H | H | Br | H | H |
| 171 | CF$_3$ | CH$_2$CH$_2$OH | H | H | N(CH$_2$CH$_3$)$_2$ | H | H |
| 172 | CF$_3$ | CH$_2$CH$_2$CN | H | H | Br | H | H |
| 173 | CF$_3$ | CH$_2$C$_6$H$_5$ | H | H | H | H | H |
| 174 | CF$_3$ | CH$_2$C$_6$H$_5$ | H | H | Cl | H | H |
| 175 | CF$_3$ | CH$_2$C$_6$H$_5$ | H | H | Br | H | H |
| 176 | C$_6$H$_5$ | CH$_3$ | H | H | Cl | H | H |
| 177 | C(O)CH$_2$CH$_3$ | CH$_3$ | H | H | N(CH$_2$CH$_3$)$_2$ | H | H |
| 178 | CO$_2$CH$_3$ | CH$_3$ | H | H | N(CH$_2$CH$_3$)$_2$ | H | H |

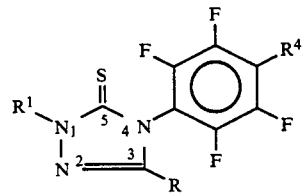

| Cmpd. No. | R | R$^1$ | R$^4$ |
|---|---|---|---|
| 179 | CF$_3$ | CH$_3$ | H |
| 180 | CF$_3$ | CH$_3$ | N(CH$_3$)$_2$ |
| 181 | CF$_3$ | CH$_3$ | N(CH$_2$CH$_3$)$_2$ |

182

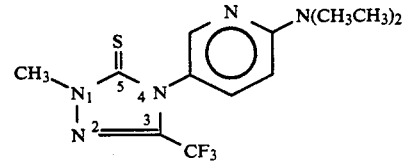

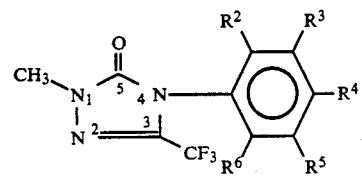

| Cmpd. No. | R$^2$ | R$^3$ | R$^4$ | R$^5$ | R$^6$ |
|---|---|---|---|---|---|
| 183 | H | H | H | H | H |
| 184 | Cl | H | H | H | H |

TABLE 1-continued
NOVEL 4-(SUBSTITUTED ARYL)-4,5-DIHYDRO-1,2,4-TRIAZOL-5(1H)-THIONES

| | | | | | | |
|---|---|---|---|---|---|---|
| 185 | F | H | H | H | H | |
| 186 | $NO_2$ | H | H | H | H | |
| 187 | H | Cl | H | H | H | |
| 188 | H | F | H | H | H | |
| 189 | H | H | Cl | H | H | |
| 190 | H | H | F | H | H | |
| 191 | H | H | $CH(CH_3)_2$ | H | H | |
| 192 | H | H | OH | H | H | |
| 193 | H | H | $OCH_3$ | H | H | |
| 194 | H | H | $OCH(CH_3)_2$ | H | H | |
| 195 | H | H | $O(CH_2)_4CH_3$ | H | H | |
| 196 | H | H | $SO_2CH_3$ | H | H | |
| 197 | $CH_3$ | H | Cl | H | H | |
| 198 | $CH_3$ | H | Br | H | H | |
| 199 | $CF_3$ | H | $NO_2$ | H | H | |
| 200 | $NO_2$ | H | Br | H | H | |
| 201 | $NO_2$ | H | $CF_3$ | H | H | |
| 202 | $NO_2$ | H | $NH[C(O)CH_3]$ | H | H | |
| 203 | H | Cl | $OCH(CH_3)_2$ | Cl | H | |
| 204 | —OC(CH$_2$)$_2$CH$_2$— | | H | H | H | |

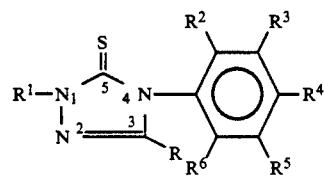

| Cmpd. No. | R | $R^1$ | $R^2$ | $R^3$ | $R^4$ | $R^5$ | $R^6$ |
|---|---|---|---|---|---|---|---|
| 205 | $CF_3$ | $CH_3$ | $OCHF_2$ | H | $OCH(CH_3)_2$ | Cl | H |
| 206 | $CF_3$ | $CH_3$ | Cl | H | $OCH(CH_3)_2$ | $OCH_3$ | H |
| 207 | $CF_3$ | $CH_3$ | Cl | H | $OCH(CH_3)_2$ | $CH_3$ | H |
| 208 | $CF_3$ | $CH_3$ | Cl | H | $OCH(CH_3)_2$ | $OCHF_2$ | H |
| 209 | $CF_2CH_3$ | $CH_3$ | Cl | H | $OCH(CH_3)_2$ | Cl | H |
| 210 | $CF_3$ | $CH_3$ | Cl | H | $OCH_2$-cyclopropyl | Cl | H |
| 211 | $CF_3$ | $CH_3$ | Cl | H | $OCH(CH_3)_2$ | Cl | H |
| 212 | $CF_3$ | $CH_3$ | Cl | H | —OC(CH$_3$)$_2$O— | | H |
| 213 | $CF_3$ | $CH_3$ | Cl | $NO_2$ | $OCH(CH_3)_2$ | Cl | H |
| 214 | $CF_3$ | $CH_3$ | Cl | $NHSO_2CH_3$ | $OCH(CH_3)_2$ | Cl | H |
| 215 | $CF_3$ | $CH_3$ | Cl | H | $N(C_2H_5)(COCH_3)$ | Cl | H |
| 216 | $CF_3$ | $CH_3$ | Cl | $NH_2$ | $OCH(CH_3)_2$ | Cl | H |
| 217 | H | $CH_3$ | Cl | H | $OCH(CH_3)_2$ | Cl | H |
| 218 | $CF_3$ | $CH_3$ | Cl | H | $NH(C_2H_5)$ | Cl | H |
| 219 | $CF_3$ | $CH_3$ | Cl | H | $OCH=CH_2$ | Cl | H |
| 220 | $CF_3$ | $CH_3$ | Cl | —COC(CH$_3$)$_2$O— | | Cl | H |
| 221 | $CF_3$ | $CH_3$ | Cl | H | $O(C_3H_7)$ | Cl | H |
| 222 | Cl | $CH_3$ | Cl | H | $OCH(CH_3)_2$ | Cl | H |
| 223 | $CF_3$ | n-$C_4H_9$ | Cl | H | $OCH(CH_3)_2$ | Cl | H |
| 224 | $CF_3$ | $CH_2$-phenyl | Cl | H | $OCH(CH_3)_2$ | Cl | H |
| 225 | $N(CH_3)_2$ | $CH_3$ | Cl | H | $OCH(CH_3)_2$ | Cl | H |
| 226 | CN | $CH_3$ | Cl | H | $OCH(CH_3)_2$ | Cl | H |
| 227 | $CF_3$ | $CH_3$ | Cl | H | $OCH_2CH=CH_2$ | Cl | H |
| 228 | $CF_3$ | $CH_3$ | Cl | —CH$_2$CH$_2$CH$_2$O— | | Cl | H |
| 229 | $CF_3$ | $CH_3$ | Cl | H | $OC(CH_3)=CH_2$ | Cl | H |
| 230 | $OCH_3$ | $CH_3$ | Cl | H | $OCH(CH_3)_2$ | Cl | H |
| 231 | $CF_3$ | $CH_2CH_2OH$ | H | H | $N(C_2H_5)_2$ | H | H |
| 232 | $CF_3$ | $CH_3$ | F | H | $OCH(CH_3)_2$ | Cl | H |
| 233 | $CF_3$ | $CH_3$ | Cl | H | $NHCOCH_3$ | H | H |
| 234 | $CF_3$ | $CH_3$ | Cl | H | $OCH_2SCH_3$ | H | H |
| 235 | $CF_3$ | $CH_3$ | F | H | $N(C_2H_5)_2$ | Cl | H |
| 236 | $CF_3$ | $CH_3$ | Cl | H | —OCH$_2$O— | | H |
| 237 | $CF_3$ | $CH_3$ | Cl | H | $N(C_2H_5)(COCF_3)$ | H | H |
| 238 | $CF_3$ | $CH_3$ | Cl | H | $CH_3$ | Cl | H |
| 239 | $CF_3$ | $CH_3$ | Cl | H | $OC(CH_3)_3$ | Cl | H |
| 240 | $CF_3$ | $CH_3$ | $CF_3$ | H | $OCH(CH_3)_2$ | H | H |
| 241 | $CF_3$ | $CH_3$ | F | H | $OCH_3$ | Cl | $SCH_3$ |

TABLE 1-continued
NOVEL 4-(SUBSTITUTED ARYL)-4,5-DIHYDRO-1,2,4-TRIAZOL-5(1H)-THIONES

| No. | | | | | | | |
|---|---|---|---|---|---|---|---|
| 242 | $CF_3$ | $CH_3$ | $SCH_3$ | H | $OCH(CH_3)_2$ | Cl | H |
| 243 | $CF_3$ | $CH_3$ | Cl | H | O-cyclopentyl | Cl | H |
| 244 | $CF_3$ | $CH_3$ | Cl | H | O-cyclohexyl | Cl | H |
| 245 | $CF_3$ | $CH_3$ | Cl | H | O-cyclobutyl | Cl | H |
| 246 | $CF_3$ | $CH_3$ | Cl | | $-CH_2C(CH_3)_2O-$ | Cl | H |
| 247 | $CF_2Cl$ | $CH_3$ | Cl | H | $OCH(CH_3)_2$ | Cl | H |
| 248 | $C_2F_5$ | $CH_3$ | Cl | H | $OCH(CH_3)_2$ | Cl | H |
| 249 | $CHF_2$ | $CH_3$ | Cl | H | $OCH(CH_3)_2$ | Cl | H |
| 250 | $CF_3$ | $CH_3$ | Cl | | $-COC(CH_3)_2O-$ | $OCHF_2$ | H |
| 251 | $CF_3$ | $CH_3$ | Cl | H | $-OC(CH_3)(C_2H_5)O-$ | | |
| 252 | $CF_3$ | $CH_3$ | Cl | | $-CH_2C(CH_3)_2O-$ | $OCHF_2$ | H |
| 253 | $CF_3$ | $CH_3$ | $CF_3$ | H | $N(CH_3)_2$ | H | H |
| 254 | $CF_3$ | $CH_3$ | $CF_3$ | H | $OCH(CH_3)_2$ | Cl | H |
| 255 | $n-C_4H_9$ | $CH_3$ | H | H | $OCH_3$ | H | H |
| 256 | $CF_3$ | $CH_3$ | Cl | H | $N(CH_3)_2$ | Cl | H |
| 257 | $CF_3$ | $CH_3$ | Br | H | $OCH(CH_3)_2$ | Br | H |
| 258 | $CF_3$ | $CH_3$ | Br | H | $OCH(CH_3)_2$ | H | H |
| 259 | $CF_3$ | $CH_3$ | Cl | H | $OCH_2CF_3$ | Cl | H |
| 260 | $CF_3$ | $CH_3$ | Cl | H | $OCH=CF_2$ | Cl | H |
| 261 | $CF_3$ | $CH_3$ | Cl | H | $OCH_2CH_2Br$ | Cl | H |

TABLE 2
Identifying Properties

| Cmpd. No. | MP (°C.) | Empirical Formula | | Elemental Analysis C | H | N |
|---|---|---|---|---|---|---|
| 1 | 290–292 | $C_9H_8ClN_3S$ | C | 47.87 | 3.57 | 18.62 |
| | | | F | 47.27 | 3.36 | 18.81 |
| 2 | 137–140 | $C_{10}H_{10}ClN_3S$ | C | 50.10 | 4.20 | 17.53 |
| | | | F | 50.14 | 4.21 | 17.59 |
| 3 | 227–231 | $C_{16}H_{14}ClN_3S$ | C | 60.85 | 4.47 | 13.30 |
| | | | F | 60.62 | 4.48 | 13.41 |
| 4 | 182–183 | $C_{10}H_7Cl_4N_3S$ | C | 35.01 | 2.06 | 12.25 |
| | | | F | 35.16 | 2.09 | 12.31 |
| 5 | oil | $C_{10}H_8F_3N_3S$ | | | | |
| 6 | 59–61 | $C_{10}H_7F_4N_3S$ | | | | |
| 7 | 89–90 | $C_{10}H_7F_4N_3S$ | C | 43.32 | 2.55 | 15.16 |
| | | | F | 42.42 | 2.62 | 14.90 |
| 8 | 94–96 | $C_{10}H_7F_4N_3S$ | | | | |
| 9 | 119–121 | $C_{10}H_7ClF_3N_3S$ | C | 40.90 | 2.40 | 14.31 |
| | | | F | 40.66 | 2.26 | 14.28 |
| 10 | 81–83 | $C_{10}H_7ClF_3N_3S$ | C | 40.90 | 2.40 | 14.31 |
| | | | F | 40.97 | 2.27 | 14.36 |
| 11 | 73–74 | $C_{10}H_7ClF_3N_3S$ | C | 40.90 | 2.40 | 14.31 |
| | | | F | 40.94 | 2.45 | 14.43 |
| 12 | 116–117 | $C_{10}H_7BrF_3N_3S$ | | | | |
| 13 | 108–110 | $C_{10}H_7BrF_3N_3S$ | | | | |
| 14 | 73–75 | $C_{10}H_7F_3IN_3S$ | C | 35.52 | 2.09 | 12.43 |
| | | | F | 35.56 | 2.16 | 12.45 |
| 15 | 140–141 | $C_{10}H_7F_3IN_3S$ | | | | |
| 16 | 89–91 | $C_{11}H_{10}F_3N_3S$ | C | 48.35 | 3.69 | 15.38 |
| | | | F | 48.07 | 3.63 | 15.50 |
| 17 | oil | $C_{11}H_{10}F_3N_3S$ | C | 48.35 | 3.69 | 15.38 |
| | | | F | 48.45 | 3.55 | 15.27 |
| 18 | 102–104 | $C_{11}H_{10}F_3N_3S$ | C | 48.35 | 3.69 | 15.38 |
| | | | F | 48.24 | 3.72 | 15.58 |
| 19 | oil | $C_{12}H_{12}F_3N_3S$ | C | 50.17 | 4.21 | 14.63 |
| | | | F | 48.26 | 4.19 | 13.61 |
| 20 | oil | $C_{13}H_{14}F_3N_3S$ | | | | |
| 21 | 145–147 | $C_{11}H_7F_6N_3S$ | | | | |
| 22 | 56–59 | $C_{11}H_7F_6N_3S$ | | | | |
| 23 | 107–108 | $C_{11}H_7F_6N_3S$ | C | 40.37 | 2.16 | 12.84 |
| 24 | 90–91 | $C_{12}H_8F_3N_3$ | F | 40.13 | 2.15 | 12.87 |
| | | | C | 50.88 | 2.83 | 14.84 |
| | | | F | 51.28 | 2.81 | 14.12 |
| 25 | — | $C_{12}H_8F_3N_3S$ | | | | |
| 26 | 79–81 | $C_{15}H_{16}F_3N_3SSi$ | | | | |
| 27 | 64–66 | $C_{13}H_{12}F_3N_3S$ | C | 52.17 | 4.01 | 14.05 |
| | | | F | 52.03 | 3.88 | 13.92 |
| 28 | 165–166 | $C_{11}H_7F_4N_3S$ | C | 46.48 | 2.48 | 19.71 |
| | | | F | 46.39 | 2.68 | 19.96 |
| 29 | 60–61 | $C_{11}H_7F_4N_3S$ | | | | |
| 30 | 190–193 | $C_{10}H_7F_3N_4O_2S$ | | | | |
| 31 | oil | $C_{10}H_7F_3N_4O_2S$ | | | | |
| 32 | 108–109 | $C_{10}H_7F_3N_4O_2S$ | C | 39.48 | 2.32 | 18.41 |
| | | | F | 40.63 | 2.66 | 17.95 |
| 33 | 173–175 | $C_{10}H_9F_3N_4S$ | | | | |
| 34 | gum | $C_{10}H_9F_3N_4S$ | | | | |
| 35 | 104–107 | $C_{10}H_9F_3N_4S$ | | | | |
| 36 | gum | $C_{11}H_{11}F_3N_4S$ | | | | |
| 37 | 139–142 | $C_{12}H_{13}F_3N_4S$ | C | 47.68 | 4.30 | 18.54 |
| | | | F | 47.76 | 4.43 | 18.42 |
| 38 | 177–179 | $C_{16}H_{13}F_3N_4S$ | | | | |
| 39 | 244–246 | $C_{12}H_{11}F_3N_4OS$ | | | | |
| 40 | oil | $C_{12}H_{13}F_3N_4S$ | | | | |
| 41 | 151–152 | $C_{12}H_{13}F_3N_4S$ | C | 47.68 | 4.30 | 18.54 |
| | | | F | 47.41 | 4.16 | 18.38 |
| 42 | 110–113 | $C_{14}H_{17}F_3N_4S$ | C | 50.91 | 5.15 | 16.97 |
| | | | F | 51.71 | 5.10 | 16.74 |
| 43 | 210–211 | $C_{14}H_{18}ClF_3N_4S$ | | | | |
| 44 | 99–102 | $C_{14}H_{16}F_4N_4S$ | | | | |
| 45 | 109–110 | $C_{16}H_{17}F_7N_4S$ | | | | |
| 46 | 154–157 | $C_{16}H_{23}N_5OS$ | | | | |
| 47 | gum | $C_{16}H_{21}F_3N_4S$ | | | | |
| 48 | 59–60 | $C_{14}H_{17}F_3N_4S$ | | | | |
| 49 | 85–86 | $C_{14}H_{17}F_3N_4S$ | | | | |
| 50 | 110–113 | $C_{14}H_{14}F_6N_4S$ | | | | |
| 51 | 99–102 | $C_{17}H_{14}F_4N_4S$ | | | | |

TABLE 2-continued

| Cmpd. No. | MP (°C.) | Empirical Formula | Elemental Analysis | C | H | N |
|---|---|---|---|---|---|---|
| 52 | >220 | C₁₃H₁₆F₃IN₄S | | | | |
| 53 | 131-134 | C₁₀H₈F₃N₃OS | | | | |
| 54 | 72-75 | C₁₀H₈F₃N₃OS | | | | |
| 55 | 138-140 | C₁₁H₁₀F₃N₄OS | C | 45.67 | 3.46 | 14.53 |
| | | | F | 45.62 | 3.18 | 14.37 |
| 56 | oil | C₁₁H₁₀F₃N₃OS | | | | |
| 57 | oil | C₁₁H₁₀F₃N₃OS | | | | |
| 58 | oil | C₁₃H₁₄F₃N₃OS | C | 49.21 | 4.42 | 13.25 |
| | | | F | 49.50 | 4.71 | 13.09 |
| 59 | 89-91 | C₁₃H₁₄F₃N₃OS | C | 49.21 | 4.42 | 13.25 |
| | | | F | 49.02 | 4.28 | 13.13 |
| 60 | 93-95 | C₁₂H₁₂F₃N₃OS | | | | |
| 61 | 68-70 | C₁₃H₁₄F₃N₃OS | C | 49.21 | 4.42 | 13.25 |
| | | | F | 49.35 | 4.35 | 13.05 |
| 62 | 69-70 | C₁₄H₁₆F₃N₃OS | | | | |
| 63 | oil | C₁₅H₁₈F₃N₃OS | | | | |
| 64 | 52-53 | C₁₅H₁₈F₃N₃OS | | | | |
| 65 | 84-86 | C₁₆H₂₀F₃N₃OS | C | 54.70 | 3.44 | 11.96 |
| | | | F | 54.63 | 3.35 | 12.01 |
| 66 | 116-117 | C₁₆H₁₁F₄N₃OS | | | | |
| 67 | — | C₁₇H₁₄F₃N₃OS | | | | |
| 68 | 71-75 | C₁₁H₁₀F₃N₃S₂ | | | | |
| 69 | 207-209 | C₁₁H₁₀F₃N₃O₂S₂ | | | | |
| 70 | 103-104 | C₁₇H₁₄F₃N₃S | C | 58.45 | 4.01 | 12.03 |
| | | | F | 58.35 | 4.12 | 11.87 |
| 71 | gum | C₁₂H₁₀F₃N₃OS | | | | |
| 72 | 151-153 | C₁₂H₁₀F₃N₃OS | C | 47.84 | 3.32 | 13.95 |
| | | | F | 48.82 | 3.41 | 13.79 |
| 73 | 122-124 | C₁₇H₁₂F₃N₃OS | C | 56.20 | 3.31 | 11.57 |
| | | | F | 55.97 | 3.48 | 11.30 |
| 74 | 141-142 | C₁₇H₁₂F₃N₃OS | C | 56.20 | 3.31 | 11.57 |
| | | | F | 56.32 | 3.30 | 11.29 |
| 75 | 150-153 | C₁₄H₁₅F₃N₄S | | | | |
| 76 | 133-135 | C₁₅H₁₇F₃N₄S | | | | |
| 77 | 65-66 | C₁₄H₁₅F₃N₄OS | | | | |
| 78 | 115-117 | C₁₄H₁OF₆N₆S | | | | |
| 79 | 65-66 | C₁₄H₁₀F₆N₆S | | | | |
| 80 | 118-120 | C₁₀H₆C₁₂F₃N₃S | C | 36.59 | 1.83 | 12.80 |
| | | | F | 36.82 | 2.02 | 12.55 |
| 81 | oil | C₁₀H₆C₁₂F₃N₃S | | | | |
| 82 | 74-75 | C₁₀H₆F₅N₃S | | | | |
| 83 | 80-85 | C₁₀H₆BrF₄N₃S | | | | |
| 84 | 149-151 | C₁₀H₆Cl₂F₃N₃S | C | 36.59 | 1.83 | 12.80 |
| | | | F | 36.51 | 1.95 | 12.59 |
| 85 | 52-55 | C₁₀H₆F₅N₃S | | | | |
| 86 | 117-119 | C₁₀H₆Cl₂F₃N₃S | | | | |
| 87 | 80-83 | C₁₀H₆F₅N₃S | | | | |
| 88 | 96-97 | C₁₀H₆Cl₂F₃N₃S | C | 36.59 | 1.83 | 12.80 |
| | | | F | 36.47 | 1.74 | 12.83 |
| 89 | 130-131 | C₁₀H₆Cl₂F₃N₃S | | | | |
| 90 | 90-93 | C₁₀H₆BrClF₃N₃S | C | 32.22 | 1.61 | 11.28 |
| | | | F | 32.70 | 1.75 | 10.82 |
| 91 | 117-119 | C₁₀H₆ClF₃IN₃S | | | | |
| 92 | 50-53 | C₁₈H₁₁ClF₃N₃S | C | 54.89 | 2.80 | 10.67 |
| | | | F | 54.78 | 2.69 | 10.70 |
| 93 | 152-155 | C₁₀H₆ClF₃N₄O₂S | | | | |
| 94 | 145-147 | C₁₀H₈ClF₃N₄S | | | | |
| 95 | 127-130 | C₁₁H₁₀ClF₃N₄S | | | | |
| 96 | 87-90 | C₁₂H₁₂ClF₃N₄S | | | | |
| 97 | 122-125 | C₁₂H₁₂ClF₃N₄S | C | 42.79 | 3.57 | 16.64 |
| | | | F | 42.83 | 3.42 | 16.70 |
| 98 | 108-110 | C₁₄H₁₆ClF₃N₄S | | | | |
| 99 | oil | C₁₁H₉ClF₃N₃S | | | | |
| 100 | 75-76 | C₁₁H₉ClF₃N₃S | C | 42.94 | 2.95 | 13.65 |
| | | | F | 42.94 | 2.95 | 13.79 |
| 101 | oil | C₁₁H₉ClF₃N₃S | | | | |
| 102 | 104-105 | C₁₁H₉ClF₃N₃S | C | 42.94 | 2.95 | 13.65 |
| | | | F | 42.73 | 2.73 | 12.68 |
| 103 | 99-101 | C₁₁H₉ClF₃N₃S | C | 42.94 | 2.95 | 13.65 |
| | | | F | 42.47 | 3.01 | 13.74 |
| 104 | 75-76 | C₁₁H₉F₄N₃S | | | | |
| 105 | 80-84 | C₁₁H₉BrF₃N₃S | C | 37.52 | 2.58 | 11.93 |
| | | | F | 37.31 | 2.45 | 11.83 |
| 106 | 104-107 | C₁₁H₉F₃IN₃S | C | 33.09 | 2.26 | 10.53 |
| | | | F | 33.17 | 2.27 | 10.33 |
| 107 | 97-99 | C₁₂H₁₂F₃N₃S | | | | |
| 108 | 71-72 | C₁₂H₁₂F₃N₃S | | | | |
| 109 | 100-101 | C₁₂H₁₂F₃N₃S | | | | |
| 110 | 74-76 | C₁₂H₁₂F₃N₃S | C | 50.17 | 4.18 | |
| | | | F | 49.94 | 3.89 | |
| 111 | oil | C₁₃H₁₀F₃N₃S | C | 52.53 | 3.37 | 14.14 |
| | | | F | 52.29 | 3.09 | 13.87 |
| 112 | 111-113 | C₁₉H₁₄F₃N₃S | C | 61.13 | 3.75 | 11.26 |
| | | | F | 60.87 | 3.62 | 11.20 |
| 113 | 90-93 | C₁₆H₁₈F₃N₃SSi | | | | |
| 114 | 84-85 | C₁₂H₁₂F₃N₃S | C | 50.17 | 4.18 | 14.63 |
| | | | F | 49.51 | 14.45 | 14.56 |
| 115 | 84-85 | C₁₂H₁₂F₃N₃S | C | 50.17 | 4.18 | |
| | | | F | 49.98 | 4.06 | |
| 116 | 220-222 | C₁₈H₁₂F₆N₄OS | | | | |
| 117 | 94-96 | C₁₀H₆F₄N₄O₂S | | | | |
| 118 | 131-134 | C₁₀H₆ClF₃N₄O₂S | | | | |
| 119 | 114-116 | C₁₀H₆BrF₃N₄O₂S | | | | |
| 120 | — | C₁₁H₆F₆N₄O₂S | | | | |
| 121 | gum | C₁₂H₁₀F₃N₅O₃S | | | | |
| 122 | 166-168 | C₁₀H₈F₄N₄S | | | | |
| 123 | 144-146 | C₁₀H₈ClF₃N₄S | | | | |
| 124 | 207-210 | C₁₂H₁₀ClF₃N₄OS | C | 41.08 | 2.85 | 15.98 |
| | | | F | 40.81 | 2.62 | 15.76 |
| 125 | 135-137 | C₁₇H₁₂F₄N₄OS | | | | |
| 126 | 193-195 | C₁₀H₇F₃N₄O₃S | | | | |
| 127 | 171-174 | C₁₀H₈F₃N₃O₂S | | | | |
| 128 | oil | C₁₂H₁₂F₃N₃O₂S | | | | |
| 129 | 138-140 | C₁₁H₉F₃N₄O₃S | | | | |
| 130 | 166-169 | C₁₃H₁₂F₃N₅O₃S₂ | | | | |
| 131 | 88-90 | C₁₂H₁₂F₃N₃O₂S | | | | |
| 132 | oil | C₁₄H₁₆F₃N₃O₂S | | | | |
| 133 | 134-137 | C₁₁H₉F₃N₄O₂S | | | | |
| 134 | 217-220 | C₁₃H₁₂F₃N₅O₃S₂ | | | | |
| 135 | 125-127 | C₁₀H₅Cl₃F₃N₃S | | | | |
| 136 | 123-125 | C₁₀H₅Cl₃F₃N₃S | | | | |
| 137 | oil | C₁₀H₅ClF₅N₃S | | | | |
| 138 | 88-89 | C₁₄H₁₅F₅N₄S | | | | |
| 139 | 129-133 | C₁₄H₁₃F₅N₄OS | | | | |
| 140 | oil | C₁₄H₁₅Cl₂F₃N₄S | | | | |
| 141 | 123-124 | C₁₁H₈Cl₂F₃N₃OS | | | | |
| 142 | 141-143 | C₁₁H₈Cl₂F₃N₃OS | | | | |
| 143 | 97-99 | C₁₃H₁₂Cl₂F₃N₃OS | | | | |
| 144 | 80-84 | C₁₀H₅Cl₃F₃N₃S | | | | |
| 145 | 106-108 | C₁₄H₁₅F₅N₄S | | | | |
| 146 | 118-121 | C₁₀H₅Cl₃F₃N₃S | C | 33.10 | 1.38 | 11.59 |
| | | | F | 32.60 | 1.43 | 11.46 |
| 147 | 115-117 | C₁₀H₅ClF₅N₃S | | | | |
| 148 | — | C₁₃H₁₂Cl₂F₃N₃OS | | | | |
| 149 | 73-75 | C₁₄H₁₅Cl₂F₃N₄S | C | 42.11 | 3.76 | 14.04 |
| | | | F | 42.15 | 3.74 | 14.11 |
| 150 | gum | C₁₂H₁₁Cl₂F₃N₄S | C | 38.81 | 2.96 | 15.09 |
| | | | F | 38.55 | 3.14 | 14.84 |
| 151 | 128-130 | C₁₄H₁₅Cl₂F₃N₄S | | | | |
| 152 | 77-78 | C₁₃H₁₂F₅N₃OS | | | | |
| 153 | 83-85 | C₁₃H₁₃F₅N₄S | | | | |
| 154 | 118-121 | C₁₆H₁₉Cl₂F₃N₄S | | | | |
| 155 | 63-66 | C₁₃H₁₄F₃N₃S | | | | |
| 156 | 100-103 | C₁₃H₁₄F₃N₃S | C | 51.83 | 4.65 | |
| | | | F | 51.62 | 4.36 | |
| 157 | 100-102 | C₁₃H₁₄F₃N₃S | | | | |
| 158 | 161-163 | C₁₃H₁₄F₃N₃O₃S | C | 44.70 | 4.01 | 12.03 |
| | | | F | 44.53 | 4.03 | 12.03 |
| 159 | oil | C₁₄H₁₄F₄N₄O₂S | | | | |
| 160 | 148-151 | C₁₁H₈F₃N₃O₂S | C | 43.57 | 2.66 | 13.86 |
| | | | F | 43.21 | 2.53 | 13.51 |
| 161 | 97-99 | C₁₄H₁₄F₃N₃OS | | | | |
| 162 | gum | C₁₄H₁₄F₃N₃O₂S | C | 48.70 | 4.06 | 12.17 |
| | | | F | 49.49 | 4.29 | 16.77 |
| 163 | 104-106 | C₁₆H₂₀F₃N₅S | | | | |
| 164 | oil | C₁₅H₁₇F₃N₄OS | | | | |
| 165 | 154-157 | C₁₂H₁₀F₃N₃O₂S | | | | |
| 166 | 88-90 | C₁₅H₁₉F₃N₄S | | | | |
| 167 | 109-111 | C₁₆H₂₁F₃N₄S | | | | |
| 168 | oil | C₁₁H₁₀F₃N₃OS | | | | |
| 169 | 130-132 | C₁₁H₉ClF₃N₃OS | C | 40.81 | 2.80 | 12.98 |
| | | | F | 40.94 | 2.81 | 13.03 |
| 170 | 137-139 | C₁₁H₉BrF₃N₃OS | C | 35.89 | 2.46 | 11.42 |
| | | | F | 36.02 | 2.50 | 11.36 |
| 171 | oil | C₁₅H₁₉F₃N₄OS | | | | |
| 172 | 136-137 | C₁₂H₈BrF₃N₄S | C | 38.21 | 2.14 | 14.85 |

TABLE 2-continued

| Cmpd. No. | MP (°C.) | Empirical Formula | | Elemental Analysis | | |
|---|---|---|---|---|---|---|
| | | | | C | H | N |
| | | | F | 38.35 | 2.35 | 15.05 |
| 173 | 148–150 | $C_{16}H_{12}F_3N_3S$ | C | 57.31 | 3.61 | 12.53 |
| | | | F | 57.41 | 3.62 | 12.66 |
| 174 | 88–91 | $C_{16}H_{11}ClF_3N_3S$ | C | 51.97 | 3.00 | 11.36 |
| | | | F | 51.98 | 3.14 | 11.33 |
| 175 | oil | $C_{16}H_{11}BrF_3N_3S$ | | | | |
| 176 | 208–210 | $C_{15}H_{12}ClN_3S$ | C | 59.70 | 4.01 | 13.92 |
| | | | F | 59.06 | 3.78 | 14.06 |
| 177 | 148–149 | $C_{16}H_{22}N_4OS$ | | | | |
| 178 | 168–169 | $C_{15}H_{20}N_4O_2S$ | | | | |
| 179 | oil | $C_{10}H_4F_7N_3S$ | | | | |
| 180 | 73–76 | $C_{12}H_9F_7N_4S$ | | | | |
| 181 | 37–40 | $C_{14}H_{13}F_7N_4S$ | | | | |
| 182 | 96–98 | $C_{13}H_{16}F_3N_5S$ | C | 47.13 | 4.83 | 21.15 |
| | | | F | 47.07 | 5.13 | 20.92 |
| 183 | 79–82 | $C_{10}H_8F_3N_3O$ | | | | |
| 184 | 84–87 | $C_{10}H_7ClF_3N_3O$ | | | | |
| 185 | oil | $C_{10}H_7F_4N_3O$ | | | | |
| 186 | oil | $C_{10}H_7F_3N_4O_3$ | | | | |
| 187 | 102–104 | $C_{10}H_7ClF_3N_3O$ | C | 43.24 | 2.52 | 15.14 |
| | | | F | 43.03 | 2.37 | 14.98 |
| 188 | 45–46 | $C_{10}H_7F_4N_3O$ | | | | |
| 189 | oil | $C_{10}H_7ClF_3N_3O$ | C | 43.24 | 2.52 | 15.14 |
| | | | F | 43.28 | 2.46 | 15.03 |
| 190 | 98–100 | $C_{10}H_7F_4N_3O$ | | | | |
| 191 | 56–57 | $C_{13}H_{14}F_3N_3O$ | C | 54.74 | 4.91 | 14.74 |
| | | | F | 55.02 | 5.05 | 14.44 |
| 192 | 205–206 | $C_{10}H_8F_3N_3O_2$ | | | | |
| 193 | 76–78 | $C_{11}H_{10}F_3N_3O_2$ | C | 48.35 | 3.66 | 15.38 |
| | | | F | 48.21 | 3.45 | 15.17 |
| 194 | 83–85 | $C_{13}H_{14}F_3N_3O_2$ | | | | |
| 195 | oil | $C_{15}H_{18}F_3N_3O_2$ | | | | |
| 196 | 147–148 | $C_{11}H_{10}F_3N_3O_3S$ | C | 41.12 | 3.14 | 13.10 |
| | | | F | 42.06 | 3.14 | 12.94 |
| 197 | 65–67 | $C_{11}H_9ClF_3N_3O$ | | | | |
| 198 | 80–83 | $C_{11}H_9BrF_3N_3O$ | C | 39.30 | 2.68 | 12.50 |
| | | | F | 39.26 | 2.40 | 12.34 |
| 199 | 155–156 | $C_{11}H_6F_6N_4O_3$ | | | | |
| 200 | 120–122 | $C_{10}H_6BrF_3N_4O_3$ | | | | |
| 201 | 138–140 | $C_{11}H_6F_6N_4O_3$ | | | | |
| 202 | gum | $C_{12}H_{10}F_3N_5O_4$ | | | | |
| 203 | — | $C_{13}H_{12}Cl_2F_3N_3O_2$ | | | | |
| 204 | 99–101 | $C_{14}H_{14}F_3N_3O_2$ | | | | |
| 205 | 105 | $C_{14}H_{13}ClF_5N_3O_2S$ | | | | |
| 206 | gum | $C_{14}H_{15}ClF_3N_3O_2S$ | | | | |
| 207 | 84 | $C_{14}H_{15}ClF_3N_3OS$ | | | | |
| 208 | oil | $C_{14}H_{13}ClF_5N_3O_2S$ | | | | |
| 209 | 99–102 | $C_{14}H_{15}Cl_2F_2N_3OS$ | | | | |
| 210 | 167–170 | $C_{14}H_{12}Cl_2F_3N_3OS$ | | | | |
| 211 | 118–121 | $C_{12}H_{10}Cl_2F_3N_3OS$ | | | | |
| 212 | 48–51 | $C_{13}H_{11}ClF_3N_3O_2S$ | | | | |
| 213 | 151–153 | $C_{13}H_{11}Cl_2F_3N_4O_3S$ | | | | |
| 214 | 62–66 | $C_{14}H_{15}Cl_2F_3N_4O_3S_2$ | | | | |
| 215 | 58–61 | $C_{14}H_{13}Cl_2F_3N_4OS$ | | | | |
| 216 | 48–50 | $C_{13}H_{13}Cl_2F_3N_4OS$ | | | | |
| 217 | 101–103 | $C_{12}H_{13}Cl_2N_3OS$ | | | | |
| 218 | gum | $C_{12}H_{11}Cl_2F_3N_4S$ | | | | |
| 219 | 111–114 | $C_{12}H_8Cl_2F_3N_3OS$ | | | | |
| 220 | 165–168 | $C_{14}H_{10}Cl_2F_3N_3O_2S$ | | | | |
| 221 | 140–143 | $C_{13}H_{12}Cl_2F_3N_3OS$ | | | | |
| 222 | 69–72 | $C_{12}H_{12}Cl_3N_3OS$ | | | | |
| 223 | liquid | $C_{16}H_{18}Cl_2F_3N_3OS$ | | | | |
| 224 | 111–112 | $C_{19}H_{16}Cl_2F_3N_3OS$ | | | | |
| 225 | 131–134 | $C_{14}H_{18}Cl_2N_4OS$ | | | | |
| 226 | 103–105 | $C_{13}H_{12}Cl_2N_4OS$ | | | | |
| 227 | 125–128 | $C_{13}H_{10}Cl_2F_3N_3OS$ | | | | |
| 228 | 64–67 | $C_{13}H_{10}Cl_2F_3N_3OS$ | | | | |
| 229 | oil | $C_{13}H_{10}Cl_2F_3N_3OS$ | | | | |
| 230 | oil | $C_{13}H_{15}Cl_2N_3O_2S$ | | | | |
| 231 | oil | $C_{15}H_{19}F_3N_4OS$ | | | | |
| 232 | viscous oil | $C_{13}H_{12}ClF_4N_3OS$ | | | | |
| 233 | 211–214 | $C_{12}H_{10}ClF_3N_4OS$ | | | | |
| 234 | 148–151 | $C_{12}H_{10}Cl_2F_3N_3OS$ | | | | |
| 235 | oil | $C_{14}H_{15}ClF_4N_4S$ | | | | |
| 236 | 110–113 | $C_{11}H_7ClF_3N_3O_2S$ | | | | |
| 237 | 109–111 | $C_{14}H_{11}ClF_6N_4OS$ | | | | |
| 238 | 123–126 | $C_{11}H_8Cl_2F_3N_3S$ | | | | |
| 239 | 87–88 | $C_{14}Cl_2F_3N_3OS$ | | | | |
| 240 | 78–80 | $C_{14}H_{13}F_6N_3OS$ | | | | |
| 241 | gum | $C_{12}H_{10}ClF_4N_3OS_2$ | | | | |
| 242 | 120–121 | $C_{14}H_{15}ClF_3N_3OS_2$ | | | | |
| 243 | 133–136 | $C_{15}H_{14}Cl_2F_3N_3OS$ | | | | |
| 244 | 56–60 | $C_{16}H_{16}Cl_2F_3N_3OS$ | | | | |
| 245 | 104–108 | $C_{14}H_{12}Cl_2F_3N_3OS$ | | | | |
| 246 | 56–60 | $C_{14}H_{12}Cl_2F_3N_3OS$ | | | | |
| 247 | liquid | $C_{13}H_{12}Cl_3F_2N_3OS$ | | | | |
| 248 | 87–90 | $C_{14}H_{12}Cl_2F_5N_3OS$ | | | | |
| 249 | 110–113 | $C_{13}H_{13}Cl_2F_2N_3OS$ | | | | |
| 250 | 150–152 | $C_{15}H_{11}ClF_5N_3O_2S$ | | | | |
| 251 | oil | $C_{14}H_{13}ClF_3N_3O_2S$ | | | | |
| 252 | viscous oil | $C_{15}H_{13}ClF_5N_3O_2S$ | | | | |
| 253 | 114–116 | $C_{13}H_{12}F_6N_4S$ | | | | |
| 254 | 70–72 | $C_{14}H_{12}ClF_6N_3OS$ | | | | |
| 255 | oil | $C_{14}H_{19}N_3OS$ | | | | |
| 256 | 106 | $C_{12}H_{11}Cl_2F_3N_4S$ | | | | |
| 257 | 48–52 | $C_{13}H_{12}Br_2F_3N_3OS$ | | | | |
| 258 | gum | $C_{13}H_{13}BrF_3N_3OS$ | | | | |
| 259 | 167–169 | $C_{12}H_7Cl_2F_6N_3OS$ | | | | |
| 260 | 122–126 | $C_{12}H_6Cl_2F_5N_3OS$ | | | | |
| 261 | 140–143 | $C_{12}H_9BrCl_2F_3N_3OS$ | | | | |

TABLE 3

Preemergence Herbicidal Activity (% Control)

| | Compound No. | | | | | | | | | | | | | | | | | | | | | | | |
|---|---|---|---|---|---|---|---|---|---|---|---|---|---|---|---|---|---|---|---|---|---|---|---|---|
| | 1* | 2* | 3* | 4* | 5 | 6 | 7* | 8 | 9* | 10* | 11 | 12 | 13 | 14* | 15 | 16* | 17 | 18 | 19 | 20 | 21 | 22 | 23 | 24 |
| | Rate (kg/ha) | | | | | | | | | | | | | | | | | | | | | | | |
| Species | 8 | 8 | 8 | 8 | 8 | 8 | 8 | 8 | 8 | 8 | 8 | 8 | 8 | 8 | 8 | 8 | 8 | 8 | 8 | 8 | 8 | 8 | 8 | 8 |
| SOYBEAN | | 0 | 0 | | 10 | 30 | 0 | 0 | 0 | 0 | 10 | 0 | 40 | | 5 | 0 | 0 | 5 | 5 | 20 | 10 | 0 | 0 | 10 |
| LIMABEAN | 100 | 0 | 0 | 0 | | | 0 | | 0 | 0 | | | 0 | | | 0 | | | | | | | | |
| CORN | | 0 | 0 | | 0 | 80 | 30 | 0 | 0 | 30 | 95 | 0 | 10 | | 10 | 30 | 30 | 0 | 10 | 90 | 0 | 0 | 0 | |
| WHEAT | | 0 | 0 | | 10 | 0 | 0 | 0 | 0 | 0 | 30 | 0 | 0 | | 0 | 70 | 0 | 5 | 5 | 60 | 0 | 0 | 0 | 0 |
| TOMATO | 60 | 0 | 0 | 0 | | | 0 | | 0 | 0 | | | 0 | | | 50 | | | | | | | | |
| VELVETLF | 0 | 0 | 0 | 0 | 10 | 60 | 0 | 0 | 0 | 0 | 90 | 0 | 20 | 30 | 10 | 0 | 20 | 50 | 30 | 80 | 10 | 0 | 0 | 0 |
| BINDWEED | 0 | 0 | 0 | 0 | | | 0 | | 0 | 0 | 20 | | | 70 | | 0 | | | | | | | | |
| WILDOAT | 80 | 0 | 0 | 0 | | | 60 | | 0 | 0 | | | | 60 | | 90 | | | | | | | | |
| BARNYDGR | 0 | 0 | 0 | 0 | 20 | 60 | 90 | 0 | 50 | 80 | 100 | 50 | 80 | 100 | 80 | 95 | 60 | 95 | 95 | 95 | 80 | 70 | 0 | 0 |
| FOXGREEN | 20 | 20 | 0 | 0 | 0 | 30 | 0 | 0 | 10 | 0 | 80 | 40 | 90 | 70 | 40 | 95 | 90 | 30 | 90 | 100 | 50 | 70 | 0 | 10 |
| GLORYSPP | | | | | 10 | 60 | | 0 | | | 70 | 30 | 60 | 0 | 20 | | 20 | 80 | 70 | 70 | 10 | 0 | 0 | 0 |
| COTTON | | | | | | | | | | | 10 | | | | 5 | | | 0 | 20 | 20 | | | | |
| JOHNGR | | | | | | | | | | | 90 | | | | 80 | | | 95 | 95 | 95 | | | | |
| RICE | | | | | | | | | | | 95 | | | | 10 | | | 50 | 95 | 95 | | | | |
| MUSTWILD | | | | | | | | | | | | | | | 0 | | | 0 | 0 | 20 | | | | |

Compound No.

TABLE 3-continued

Preemergence Herbicidal Activity (% Control)

| | 26 | 27 | 28* | 29 | 30 | 31 | 32* | 33 | 34 | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|---|---|---|---|---|---|---|---|---|
| | | | | | | | | | | | | Rate (kg/ha) | | | | | | | | | | | | |
| Species | 8 | 4 | 8 | 8 | 8 | 8 | 8 | 8 | 8 | 8 | 8 | 8 | 8 | 8 | 8 | 8 | 8 | 2 | 2 | 8 | 8 | 8 | 8 | 8 |
| SOYBEAN | 0 | 10 | 0 | 0 | 0 | 30 | 0 | 0 | 0 | 0 | 0 | 40 | 0 | 20 | 0 | 50 | 5 | 20 | 0 | 0 | 10 | 0 | 70 | |
| LIMABEAN | | | 0 | | | | 0 | | | | | | | | | | | | | | | | | |
| CORN | 0 | 5 | 0 | 0 | 0 | 10 | 0 | 0 | 0 | 0 | 50 | 50 | 0 | 0 | 40 | 20 | 60 | 5 | 5 | 0 | 0 | 40 | 10 | 70 |
| WHEAT | 0 | 0 | 0 | 0 | 0 | 10 | 0 | 0 | 0 | 0 | 0 | 10 | 0 | 20 | 30 | 0 | 30 | 0 | 10 | 0 | 0 | 60 | 0 | 30 |
| TOMATO | | | | | | | 0 | | | | | | | | | | | | | | | | | |
| VELVETLF | 0 | 20 | 90 | 10 | 0 | 50 | 0 | 0 | 0 | 0 | 70 | 100 | 0 | 0 | 100 | 50 | 70 | 30 | 30 | 0 | 0 | 80 | 80 | 95 |
| BINDWEED | | | 0 | | | | 0 | | | | | | | | | 60 | | | | | | | | |
| WILDOAT | | | | | | | 0 | | | | | | | | | | | | | | | | | |
| BARNYDGR | 0 | 90 | 40 | 90 | 0 | 70 | 0 | 0 | 0 | 0 | 70 | 90 | 0 | 20 | 100 | 95 | 95 | 80 | 95 | 0 | 0 | 90 | 95 | 95 |
| FOXGREEN | 0 | 30 | 80 | 90 | 0 | 95 | 0 | 0 | 0 | 0 | 80 | 95 | 0 | 0 | 95 | 90 | 95 | 95 | 90 | 0 | 0 | 95 | 95 | 100 |
| GLORYSPP | 0 | 20 | 0 | 10 | 0 | 40 | | 10 | 0 | 10 | 50 | 70 | 0 | 70 | 70 | 70 | 70 | 10 | 80 | 0 | 0 | 70 | 80 | 70 |
| COTTON | | 0 | | | | | | | | | | 10 | | | 0 | 0 | 0 | 10 | 0 | | | | 0 | 50 |
| JOHNGR | | 20 | 70 | | | | | | | | | 95 | | | 50 | 70 | 80 | 95 | 95 | | | | 95 | 100 |
| RICE | | 80 | | | | | | | | | | 50 | | | 70 | 95 | 20 | 0 | 10 | | | | 10 | 90 |
| MUSTWILD | | 0 | | | | | | | | | | 40 | | | 60 | | 0 | 5 | 0 | | | | 70 | 70 |

| | Compound No. | | | | | | | | | | | | | | | | | | | | | | |
|---|---|---|---|---|---|---|---|---|---|---|---|---|---|---|---|---|---|---|---|---|---|---|---|
| | 50 | 51 | 52 | 53 | 54 | 55 | 56 | 57 | 58 | 59 | 60 | 61 | 62 | 63 | 64 | 65* | 66 | 67* | 68 | 69 | 70 | 71 | 72 |
| | | | | | | | | | | | Rate (kg/ha) | | | | | | | | | | | | |
| Species | 8 | 2 | 8 | 8 | 8 | 8 | 8 | 8 | 8 | 8 | 8 | 8 | 8 | 4 | 8 | 8 | 8 | 8 | 8 | 8 | 2 | 8 | 8 |
| SOYBEAN | 90 | 0 | 0 | 10 | 50 | 0 | 0 | 5 | 0 | 60 | 80 | 20 | 5 | 0 | 0 | 0 | 10 | 0 | 30 | 0 | 0 | 10 | 0 |
| LIMABEAN | | | | | | | | | | | | | | | | 0 | | 0 | | | | | |
| CORN | 60 | 5 | 0 | 0 | 90 | 0 | 10 | 50 | 70 | 30 | 95 | 95 | 5 | 20 | 0 | 0 | 0 | 0 | 60 | 0 | 5 | 10 | 0 |
| WHEAT | 60 | 0 | 0 | 0 | 0 | 0 | 40 | 10 | 5 | 50 | 50 | 70 | 5 | 10 | 10 | 0 | 0 | 0 | 50 | 0 | 0 | 30 | 0 |
| TOMATO | | | | | | | | | | | | | | | | 0 | | 0 | | | | | |
| VELVETLF | 90 | 5 | 0 | 10 | 50 | 0 | 30 | | 40 | 90 | 95 | 80 | 20 | 0 | 0 | 0 | 0 | 0 | 40 | 0 | 50 | 60 | 0 |
| BINDWEED | | | | | | | | | | | | | | | | 0 | | 0 | | | | | |
| WILDOAT | | | | | | | | | | | | | | | | 0 | | 0 | | | | | |
| BARNYDGR | 100 | 80 | 0 | 80 | 90 | 0 | 95 | 95 | 100 | 95 | 95 | 100 | 95 | 10 | 70 | 0 | 0 | 0 | 30 | 0 | 80 | 50 | 0 |
| FOXGREEN | 100 | 90 | 0 | 30 | 90 | 90 | 90 | 95 | 95 | 100 | 100 | 100 | 95 | 0 | 90 | 90 | 0 | 0 | 80 | 50 | 95 | 90 | 0 |
| GLORYSPP | 80 | 10 | 0 | 70 | 70 | 0 | 90 | 95 | 80 | 90 | 95 | 80 | 10 | 5 | 10 | | 0 | | 80 | 0 | 10 | 50 | 0 |
| COTTON | | 0 | | | | | | 0 | 0 | 20 | 30 | 10 | 0 | 0 | | | | | | | 0 | | |
| JOHNGR | | 50 | | | | | | 95 | 95 | 95 | 95 | 95 | 70 | 0 | | | | | 60 | | | | |
| RICE | | 5 | | | | | | 50 | 90 | 90 | 100 | 95 | 0 | 5 | | | | | 5 | | | | |
| MUSTWILD | | 0 | | | | | | 0 | 0 | 50 | 0 | 95 | 5 | 0 | | | | | 10 | | | | |

| | Compound No. | | | | | | | | | | | | | | | | | |
|---|---|---|---|---|---|---|---|---|---|---|---|---|---|---|---|---|---|---|
| | 73 | 74 | 75 | 76 | 77 | 78 | 79 | 80 | 81* | 82 | 83 | 84 | 85 | 86 | 87 | 88* | 89 | 90 |
| | | | | | | | | | Rate (kg/ha) | | | | | | | | | |
| Species | 8 | 8 | 8 | 8 | 8 | 8 | 4 | 8 | 8 | 8 | 8 | 8 | 8 | 8 | 8 | 8 | 8 | 8 |
| SOYBEAN | 0 | 0 | 30 | 0 | 0 | 0 | 5 | 20 | 0 | 0 | 0 | 0 | 0 | 0 | 0 | 0 | 5 | 30 |
| LIMABEAN | | | | | | | | | 0 | | | | | | | 0 | | |
| CORN | 0 | 0 | 30 | 0 | 0 | 0 | 20 | 20 | 0 | 0 | 0 | 10 | 20 | 0 | 0 | 0 | 5 | 90 |
| WHEAT | 0 | 0 | 30 | 0 | 95 | 0 | 5 | 0 | 0 | 0 | 0 | 10 | 20 | 0 | 0 | 0 | 5 | 60 |
| TOMATO | | | | | | | | | 0 | | | | | | | 0 | | |
| VELVETLF | 0 | 0 | 50 | 0 | 20 | 0 | 40 | 10 | 0 | 0 | 0 | 20 | 0 | 0 | | 20 | 10 | 80 |
| BINDWEED | | | | | | | | | 70 | | | | | | | 90 | | |
| WILDOAT | | | | | | | | | 20 | | | | | | | 0 | | |
| BARNYDGR | 80 | 0 | 80 | 0 | 80 | 0 | 40 | 70 | 95 | 0 | 70 | 90 | 80 | 70 | 40 | 90 | 90 | 90 |
| FOXGREEN | 90 | 0 | 90 | 0 | 0 | 0 | 30 | 90 | 100 | 0 | 70 | 90 | 60 | 90 | 50 | 90 | 50 | 95 |
| GLORYSPP | 10 | 0 | 30 | 0 | 30 | 0 | 0 | 60 | | 0 | | 20 | 20 | 30 | 0 | 30 | 40 | 80 |
| COTTON | | | | | | | 0 | | | | | | | | | 0 | | |
| JOHNGR | | | | | | | | | | | | | | | | 70 | | |
| RICE | | | | | | | 20 | | | | | | | | | 40 | | |
| MUSTWILD | | | | | | | 0 | | | | | | | | | 0 | | |

| | Compound No. | | | | | | | | | | | | | | | | | | |
|---|---|---|---|---|---|---|---|---|---|---|---|---|---|---|---|---|---|---|---|
| | 91 | 92 | 93 | 94 | 95 | 96 | 97 | 98 | 99* | 100* | 101* | 102* | 103* | 104 | 105 | 106 | 107 | 108 | 109 |
| | | | | | | | | | | Rate (kg/ha) | | | | | | | | | |
| Species | 8 | 8 | 8 | 8 | 8 | 8 | 8 | 4 | 8 | 8 | 8 | 8 | 8 | 8 | 4 | 8 | 8 | 8 | 8 |
| SOYBEAN | 20 | 0 | 0 | 0 | 40 | 30 | 70 | 0 | 0 | 0 | 0 | 0 | 0 | 0 | 80 | 10 | 0 | 5 | 0 |
| LIMABEAN | | | | | | | | | 0 | 0 | 0 | 0 | | | | | | | |
| CORN | 60 | 0 | 0 | 0 | 50 | 20 | 90 | 20 | 30 | 0 | 0 | 0 | 0 | 20 | 90 | 95 | 100 | 100 | 100 |
| WHEAT | 40 | 0 | 0 | 0 | 30 | 50 | 50 | 5 | 40 | 100 | 60 | 50 | 20 | | 20 | 10 | 90 | 80 | 95 |
| TOMATO | | | | | | | | | 50 | 80 | 50 | 0 | 100 | | | | | | |
| VELVETLF | 80 | 0 | 0 | 0 | 90 | 90 | 100 | 60 | 0 | 40 | 0 | 0 | 20 | 0 | 90 | 80 | 90 | 80 | 90 |
| BINDWEED | | | | | | | | | 60 | 40 | 0 | 0 | 0 | | 80 | | | | |
| WILDOAT | | | | | | | | | 30 | 80 | 0 | 90 | 0 | | | | | | |
| BARNYDGR | 95 | 0 | 0 | 90 | 90 | 100 | 95 | 95 | 90 | 100 | 80 | 90 | 0 | 90 | 100 | 100 | 100 | 100 | 100 |
| FOXGREEN | 100 | 0 | 0 | 0 | 95 | 95 | 100 | 100 | 100 | 100 | 100 | 100 | 100 | 30 | 100 | 100 | 95 | 100 | 100 |
| GLORYSPP | 95 | 0 | 0 | 0 | 95 | 95 | 95 | 70 | | | | | | 60 | 90 | 90 | 80 | 70 | 80 |
| COTTON | | | | | | 50 | 0 | 0 | | | | | | | 70 | 0 | 0 | 20 | 40 |
| JOHNGR | | | | | | 95 | 90 | 100 | | | | | | | 100 | 100 | 100 | 100 | 100 |
| RICE | | | | | | 70 | 30 | 0 | | | | | | | 50 | 100 | 100 | 100 | 100 |
| MUSTWILD | | | | | | 80 | 100 | 50 | | | | | | | 60 | 0 | 70 | 30 | |

TABLE 3-continued

Preemergence Herbicidal Activity (% Control)

| | \multicolumn{18}{c|}{Compound No.} |
|---|---|---|---|---|---|---|---|---|---|---|---|---|---|---|---|---|---|---|
| | 110 | 111 | 112 | 113 | 114* | 115 | 116 | 117 | 118 | 119 | 122 | 123 | 124 | 125 | 126 | 127 | 128 | 129 |
| Species | \multicolumn{18}{c|}{Rate (kg/ha)} |
| | 8 | 8 | 8 | 8 | 8 | 8 | 8 | 8 | 8 | 8 | 8 | 8 | 8 | 8 | 8 | 8 | 8 | 8 |
| SOYBEAN | 0 | 70 | 20 | 30 | 0 | 0 | 0 | 0 | 0 | 10 | 10 | 0 | 10 | 10 | 0 | 0 | 0 | 0 |
| LIMABEAN | | | | | 0 | | | | | | | | | | | | | |
| CORN | 20 | 95 | 0 | 0 | 60 | 90 | 0 | 40 | 0 | 90 | 10 | 0 | 5 | 10 | 0 | 0 | 10 | 0 |
| WHEAT | 30 | 40 | 0 | 0 | 100 | 70 | 100 | 40 | 0 | 50 | 10 | 30 | 50 | 30 | 0 | 0 | 0 | 0 |
| TOMATO | | | | | 40 | | | | | | | | | | | | | |
| VELVETLF | 0 | 80 | 0 | 0 | 90 | 80 | 0 | 40 | 90 | 60 | 0 | 80 | 50 | 0 | 0 | 0 | 30 | 0 |
| BINDWEED | | | | | 80 | | | | | | | | | | | | | |
| WILDOAT | | | | | 95 | | | | | | | | | | | | | |
| BARNYDGR | 50 | 100 | 40 | 70 | 100 | 100 | 0 | 90 | 70 | 95 | 10 | 60 | 10 | 0 | 30 | 0 | 90 | 40 |
| FOXGREEN | 70 | 100 | 20 | 50 | 100 | 90 | 50 | 95 | 95 | 90 | 10 | 90 | 10 | 10 | 60 | 0 | 80 | 0 |
| GLORYSPP | 0 | 80 | 40 | 0 | | 70 | 0 | 40 | 30 | 70 | 10 | 60 | 50 | 10 | 0 | 0 | 60 | 0 |
| COTTON | | 10 | | | | 0 | | | | | | | 40 | | | | | |
| JOHNGR | | 95 | | | | 100 | | | | | | | 10 | | | | | |
| RICE | | 95 | | | | 95 | | | | | | | 20 | | | | | |
| MUSTWILD | | 20 | | | | 0 | | | | | | | 80 | | | | | |

| | \multicolumn{18}{c|}{Compound No.} |
|---|---|---|---|---|---|---|---|---|---|---|---|---|---|---|---|---|---|---|
| | 130 | 131 | 132 | 133 | 134 | 135 | 136 | 137 | 138 | 139 | 140 | 141 | 142 | 143 | 144 | 145 | 146 | 147 |
| Species | \multicolumn{18}{c|}{Rate (kg/ha)} |
| | 8 | 8 | 8 | 8 | 8 | 4 | 8 | 2 | 2 | 8 | 2 | 8 | 8 | 8 | 8 | 8 | 8 | 8 |
| SOYBEAN | 0 | 0 | 30 | 0 | 0 | 10 | 0 | 0 | 80 | 40 | 60 | 80 | 50 | 80 | 30 | 0 | 40 | 0 |
| LIMABEAN | | | | | | | | | | | | | | | | | | |
| CORN | 0 | 20 | 50 | 0 | 20 | 10 | 10 | 5 | 80 | 0 | 50 | 90 | 0 | 70 | 70 | 20 | 60 | 10 |
| WHEAT | 0 | 20 | 40 | 0 | 0 | 5 | 0 | 0 | 40 | 0 | 50 | 80 | 50 | 70 | 30 | 20 | 70 | 10 |
| TOMATO | | | | | | | | | | | | | | | | | | |
| VELVETLF | 0 | 60 | 80 | 0 | 0 | 60 | 10 | 10 | 70 | 10 | 80 | 80 | 60 | 60 | 60 | 70 | 60 | 0 |
| BINDWEED | | | | | | | | | | | | | | | | | | |
| WILDOAT | | | | | | | | | | | | | | | | | | |
| BARNYDGR | 0 | 50 | 90 | 0 | 0 | 95 | 95 | 90 | 100 | 80 | 95 | 100 | 95 | 100 | 90 | 100 | 90 | 80 |
| FOXGREEN | 0 | 90 | 90 | 0 | 10 | 100 | 90 | 70 | 100 | 90 | 95 | 100 | 100 | 100 | 90 | 95 | 100 | 100 |
| GLORYSPP | 0 | 10 | 90 | 0 | 0 | 80 | 60 | 10 | 70 | 40 | 85 | 80 | 90 | 60 | 50 | 70 | 80 | 10 |
| COTTON | | | | | | 30 | 0 | 5 | 20 | | 50 | | | | | | | 0 |
| JOHNGR | | | | | | 100 | 60 | 90 | 100 | | 100 | | | | | | | 50 |
| RICE | | | | | | 60 | 20 | 20 | 70 | | 40 | | | | | | | 5 |
| MUSTWILD | | | | | | 0 | 10 | 10 | 80 | | 70 | | | | | | | 0 |

| | \multicolumn{18}{c|}{Compound No.} |
|---|---|---|---|---|---|---|---|---|---|---|---|---|---|---|---|---|---|---|
| | 148 | 149 | 150 | 151 | 152 | 153 | 154 | 155 | 156 | 157 | 158 | 159 | 160* | 161 | 162 | 163 | 164 | 165 |
| Species | \multicolumn{18}{c|}{Rate (kg/ha)} |
| | 2 | 8 | 4 | 8 | 2 | 4 | 8 | 8 | 8 | 8 | 4 | 8 | 8 | 4 | 4 | 8 | 2 | 2 |
| SOYBEAN | 10 | 10 | 80 | 0 | 10 | 70 | 20 | 40 | 40 | 40 | 5 | 0 | 0 | 5 | 5 | 0 | 20 | 5 |
| LIMABEAN | | | | | | | | | | | | | 0 | | | | | |
| CORN | 50 | 50 | 90 | 20 | 80 | 90 | 0 | 90 | 90 | 60 | 90 | 0 | 30 | 70 | 30 | 0 | 5 | 10 |
| WHEAT | 30 | 0 | 60 | 10 | 30 | 20 | 10 | 80 | 90 | 10 | 50 | 90 | 90 | 10 | 10 | 0 | 5 | 5 |
| TOMATO | | | | | | | | | | | | | 0 | | | | | |
| VELVETLF | 70 | 40 | 90 | 60 | 70 | 90 | 20 | 90 | 90 | 70 | 70 | 0 | 0 | 40 | 5 | 0 | 70 | 20 |
| BINDWEED | | | | | | | | | | | | | 0 | | | | | |
| WILDOAT | | | | | | | | | | | | | 40 | | | | | |
| BARNYDGR | 95 | 100 | 95 | 100 | 95 | 100 | 90 | 100 | 100 | 90 | 95 | 50 | 100 | 95 | 95 | 0 | 95 | 80 |
| FOXGREEN | 95 | 95 | 100 | 100 | 100 | 100 | 95 | 100 | 100 | 0 | 95 | 90 | 100 | 95 | 95 | 0 | 100 | 85 |
| GLORYSPP | 80 | 80 | 90 | 30 | 70 | 95 | 50 | 95 | 90 | 40 | 90 | 0 | | 95 | 60 | 0 | 70 | 80 |
| COTTON | 5 | 10 | 70 | 0 | 5 | 0 | | 20 | 20 | 0 | 20 | | | 5 | 5 | | 5 | 10 |
| JOHNGR | 100 | 95 | 100 | 95 | 90 | 95 | | 100 | 100 | 40 | 95 | | | 80 | 95 | | 70 | 30 |
| RICE | 70 | 20 | 70 | 20 | 95 | 95 | | 100 | 100 | 80 | 95 | | | 70 | 30 | | 20 | 50 |
| MUSTWILD | 70 | 60 | 80 | 50 | 5 | 10 | | 0 | 50 | 60 | 20 | | | 5 | 0 | | 15 | 20 |

| | \multicolumn{17}{c|}{Compound No.} |
|---|---|---|---|---|---|---|---|---|---|---|---|---|---|---|---|---|---|
| | 166 | 167 | 168* | 169* | 170* | 172* | 173* | 174* | 175* | 176* | 177 | 178 | 179 | 180 | 181 | 182 | 183 | 184 |
| Species | \multicolumn{17}{c|}{Rate (kg/ha)} |
| | 2 | 8 | 8 | 8 | 8 | 8 | 8 | 8 | 8 | 8 | 8 | 8 | 8 | 2 | 8 | 8 | 8 | 8 |
| SOYBEAN | 5 | 0 | | | | 0 | | | | | 0 | 0 | 0 | 70 | 90 | 95 | 0 | 0 |
| LIMABEAN | | | 0 | 0 | 0 | | 0 | 0 | 0 | 0 | | | | | | | | |
| CORN | 5 | 0 | | | | 0 | | | | | 0 | 0 | 50 | 50 | 60 | 95 | 0 | 10 |
| WHEAT | 0 | 30 | | | | 0 | | | | | 0 | 0 | 30 | 5 | 50 | 90 | 0 | 20 |
| TOMATO | | | 0 | 0 | 0 | | 0 | 0 | 0 | 0 | | | | | | | | |
| VELVETLF | 30 | 20 | 0 | 0 | 0 | 0 | 0 | 0 | 0 | 0 | 0 | 0 | 30 | 60 | 90 | 100 | 0 | 0 |
| BINDWEED | | | 0 | 0 | 0 | | 0 | 0 | 0 | 0 | | | | | | | | |
| WILDOAT | | | 0 | 0 | 0 | | 0 | 0 | 0 | 40 | | | | | | | | |
| BARNYDGR | 60 | 10 | 0 | 0 | 0 | 0 | 0 | 0 | 0 | 0 | 0 | 0 | 80 | 100 | 100 | 100 | 0 | 10 |
| FOXGREEN | 90 | 10 | 0 | 0 | 0 | 0 | 0 | 0 | 0 | 0 | 0 | 0 | 60 | 100 | 100 | 100 | 0 | 10 |
| GLORYSPP | 5 | 90 | | | | | | | | | 0 | 0 | 60 | 95 | 90 | 100 | 0 | 0 |
| COTTON | 0 | | | | | | | | | | | | | 0 | | 80 | | |
| JOHNGR | 50 | | | | | | | | | | | | | 100 | | 100 | | |
| RICE | 5 | | | | | | | | | | | | | 95 | | 80 | | |

TABLE 3-continued

| Preemergence Herbicidal Activity (% Control) | | |
|---|---|---|
| MUSTWILD | 0 | 10 |

| | Compound No. | | | | | | | | | | | | | | | | | |
|---|---|---|---|---|---|---|---|---|---|---|---|---|---|---|---|---|---|---|
| | 185 | 186 | 187 | 188 | 189 | 190 | 191 | 192 | 193 | 194 | 195 | 196 | 197 | 198 | 199 | 200 | 201 | 204 |
| | Rate (kg/ha) | | | | | | | | | | | | | | | | | |
| Species | 8 | 8 | 8 | 8 | 8 | 8 | 8 | 8 | 8 | 8 | 8 | 8 | 8 | 8 | 8 | 8 | 8 | 8 |
| SOYBEAN | 0 | 10 | 0 | 0 | 0 | 0 | 0 | 0 | 20 | 10 | 0 | 0 | 0 | 10 | 0 | 0 | 0 | 20 |
| LIMABEAN | | | | | | | | | | | | | | | | | | |
| CORN | 0 | 70 | 10 | 0 | 10 | 0 | 20 | 0 | 30 | 40 | 10 | 0 | 10 | 40 | 0 | 0 | 0 | 20 |
| WHEAT | 0 | 10 | 30 | 0 | 20 | 0 | 0 | 20 | 40 | 10 | 10 | 0 | 0 | 40 | 0 | 0 | 20 | 20 |
| TOMATO | | | | | | | | | | | | | | | | | | |
| VELVETLF | 0 | 60 | 0 | 0 | 50 | 0 | 10 | 0 | 10 | 40 | 10 | 0 | 70 | 90 | 0 | 0 | 0 | 10 |
| BINDWEED | | | | | | | | | | | | | | | | | | |
| WILDOAT | | | | | | | | | | | | | | | | | | |
| BARNYDGR | 0 | 80 | 10 | 0 | 0 | 0 | 70 | 10 | 20 | 90 | 10 | 0 | 95 | 95 | 0 | 30 | 0 | 30 |
| FOXGREEN | 0 | 100 | 50 | 20 | 0 | 0 | 60 | 10 | 20 | 100 | 10 | 0 | 95 | 100 | 0 | 0 | 0 | 10 |
| GLORYSPP | 0 | 40 | 0 | 0 | 0 | 0 | 30 | 0 | 20 | 80 | 10 | 0 | 80 | 95 | 0 | 0 | 0 | 10 |
| COTTON | | | | | | | 0 | | | | | | | 30 | | | | |
| JOHNGR | | | | | | | 30 | | | | | | | 80 | | | | |
| RICE | | | | | | | 40 | | | | | | | 95 | | | | |
| MUSTWILD | | | | | | | 0 | | | | | | | 0 | | | | |

| | Compound No. | | | | | | | | | | | | | | | | | |
|---|---|---|---|---|---|---|---|---|---|---|---|---|---|---|---|---|---|---|
| | 205 | 206 | 207 | 208 | 209 | 210 | 211 | 212 | 213 | 214 | 215 | 216 | 217 | 219 | 220 | 221 | 222 | 223 |
| | Rate (kg/ha) | | | | | | | | | | | | | | | | | |
| Species | 1 | 1 | 1 | 0.5 | 2 | 8 | 1 | 8 | 1 | 1 | 8 | 1 | 8 | 2 | 0.5 | 1 | 8 | 8 |
| SOYBEAN | 5 | 10 | 5 | 10 | 0 | 0 | 40 | 0 | 0 | 10 | 60 | 15 | 30 | 5 | 5 | 0 | 0 | 10 |
| LIMABEAN | | | | | | | | | | | | | | | | | | |
| CORN | 5 | 10 | 5 | 50 | 0 | 0 | 90 | 0 | 5 | 20 | 60 | 5 | 30 | 70 | 70 | 5 | 0 | 0 |
| WHEAT | 10 | 10 | 0 | 40 | 0 | 0 | 15 | 20 | 0 | 10 | 40 | 0 | 0 | 0 | 40 | 0 | 0 | 20 |
| TOMATO | | | | | | | | | | | | | | | | | | |
| VELVETLF | 70 | 5 | 70 | 70 | 0 | 0 | 80 | 90 | 40 | 10 | 90 | 70 | 0 | 85 | 70 | 20 | 40 | 30 |
| BINDWEED | | | | | | | | | | | | | | | | | | |
| WILDOAT | | | | | | | | | | | | | | | | | | |
| BARNYDGR | 100 | 100 | 95 | 100 | 50 | 20 | 100 | 90 | 90 | 40 | 95 | 95 | 70 | 100 | 90 | 95 | 0 | 50 |
| FOXGREEN | 100 | 100 | 100 | 100 | 90 | 90 | 100 | 100 | 95 | 60 | 95 | 100 | 95 | 95 | 100 | 90 | 0 | 90 |
| GLORYSPP | 15 | 50 | 20 | 70 | 0 | 0 | 85 | 90 | 15 | 20 | 90 | 5 | 20 | 80 | 90 | 30 | 0 | 30 |
| COTTON | 0 | 10 | 0 | 5 | | | 5 | | 0 | 5 | | 0 | | 0 | 60 | 0 | | |
| JOHNGR | 90 | 95 | 95 | 100 | | | 100 | | 70 | 30 | | 95 | | 95 | 95 | 95 | | |
| RICE | 5 | 90 | 5 | 15 | | | 90 | | 10 | 10 | | 40 | | 90 | 80 | 20 | | |
| MUSTWILD | 30 | 0 | 10 | 60 | | | 40 | | 15 | 10 | | 60 | | 0 | 20 | 0 | | |

| | Compound No. | | | | | | | | | | | | | | | | | |
|---|---|---|---|---|---|---|---|---|---|---|---|---|---|---|---|---|---|---|
| | 224 | 225 | 226 | 227 | 228 | 229 | 230 | 232 | 234 | 235 | 236 | 237 | 238 | 239 | 240 | 241 | 242 | 243 |
| | Rate (kg/ha) | | | | | | | | | | | | | | | | | |
| Species | 8 | 8 | 8 | 1 | 1 | 2 | 8 | 2 | 1 | 1 | 2 | 8 | 2 | 1 | 1 | 1 | 1 | 8 |
| SOYBEAN | 0 | 0 | 90 | 10 | 10 | 0 | 0 | 20 | 0 | 0 | 0 | 30 | 0 | 10 | 0 | 10 | 0 | 0 |
| LIMABEAN | | | | | | | | | | | | | | | | | | |
| CORN | 0 | 0 | 0 | 5 | 5 | 15 | 0 | 95 | 10 | 50 | 5 | 30 | 0 | 60 | 5 | 5 | 10 | 0 |
| WHEAT | 0 | 0 | 0 | 15 | 5 | 0 | 0 | 90 | 0 | 20 | 5 | 10 | 0 | 10 | 5 | 5 | 10 | 10 |
| TOMATO | | | | | | | | | | | | | | | | | | |
| VELVETLF | 0 | 0 | 0 | 40 | 70 | 90 | 0 | 80 | 20 | 100 | 5 | 90 | 5 | 40 | 5 | 0 | 0 | 0 |
| BINDWEED | | | | | | | | | | | | | | | | | | |
| WILDOAT | | | | | | | | | | | | | | | | | | |
| BARNYDGR | 0 | 0 | 0 | 90 | 90 | 100 | 0 | 100 | 100 | 95 | 90 | 100 | 100 | 95 | 90 | 30 | 40 | 70 |
| FOXGREEN | 0 | 0 | 95 | 100 | 100 | 100 | 0 | 100 | 95 | 100 | 95 | 95 | 100 | 100 | 95 | 80 | 95 | 80 |
| GLORYSPP | 0 | 0 | 0 | 50 | 20 | 90 | 0 | 70 | 70 | 70 | 60 | 95 | 0 | 50 | 0 | 0 | 15 | 30 |
| COTTON | | | | 0 | 5 | 10 | | 10 | 0 | 0 | 0 | | 0 | 0 | 0 | 0 | 0 | |
| JOHNGR | | | | 85 | 95 | 95 | | 95 | 90 | 80 | 95 | | 95 | 85 | 50 | 40 | 5 | |
| RICE | | | | 70 | 70 | 70 | | 90 | 5 | 60 | 15 | | 70 | 40 | 5 | 0 | 0 | |
| MUSTWILD | | | | 60 | 30 | 80 | | 70 | 80 | 30 | 15 | | 0 | 0 | 5 | 0 | 0 | |

| | | Compound No. | | | | | | | | | | | | |
|---|---|---|---|---|---|---|---|---|---|---|---|---|---|---|
| | | 244 | 245 | 246 | 247 | 248 | 249 | 250 | 251 | 252 | 254 | 259 | 260 | 261 |
| | | Rate (kg/ha) | | | | | | | | | | | | |
| | Species | 8 | 2 | 1 | 2 | 1 | 1 | 1 | 8 | 1 | 1 | 2 | 1 | |
| | SOYBEAN | 20 | 15 | 10 | 10 | 0 | 0 | 30 | 0 | 90 | 5 | 10 | 5 | 5 |
| | LIMABEAN | | | | | | | | | | | | | |
| | CORN | 0 | 20 | 30 | 70 | 0 | 10 | 50 | 20 | 90 | 10 | 50 | 50 | 5 |
| | WHEAT | 20 | 40 | 70 | 10 | 0 | 5 | 30 | 20 | 70 | 5 | 15 | 0 | 0 |
| | TOMATO | | | | | | | | | | | | | |
| | VELVETLF | 80 | 90 | 95 | 50 | 15 | 70 | 70 | 0 | 90 | 70 | 85 | 90 | 30 |
| | BINDWEED | | | | | | | | | | | | | |
| | WILDOAT | | | | | | | | | | | | | |
| | BARNYDGR | 20 | 100 | 100 | 95 | 90 | 95 | 100 | 50 | 100 | 90 | 95 | 100 | 80 |
| | FOXGREEN | 95 | 100 | 100 | 100 | 95 | 95 | 100 | 95 | 100 | 100 | 100 | 100 | 95 |
| | GLORYSPP | 70 | 90 | 95 | 70 | 15 | 40 | 70 | 20 | 90 | 80 | 90 | 95 | 10 |
| | COTTON | | 50 | 0 | 5 | 5 | 5 | 10 | | 50 | 5 | 0 | 0 | 0 |
| | JOHNGR | | 95 | 95 | 95 | 90 | 95 | 100 | | 95 | 95 | 95 | 100 | 60 |

TABLE 3-continued

| Preemergence Herbicidal Activity (% Control) | | | | | | | | | | | |
|---|---|---|---|---|---|---|---|---|---|---|---|
| RICE | 30 | 70 | 5 | 30 | 60 | 50 | | 85 | 5 | 50 | 5 | 15 |
| MUSTWILD | 95 | 90 | 95 | 40 | 40 | 5 | | 90 | 5 | 85 | 0 | 20 |

*Data represents % Kill (% K) rather than % Control (% C)

TABLE 4

Postemergence Herbicidal Activity (% Control)

| | Compound No. | | | | | | | | | | | | | | | | | | | | | | | |
|---|---|---|---|---|---|---|---|---|---|---|---|---|---|---|---|---|---|---|---|---|---|---|---|---|
| | 1* | 2* | 3* | 4* | 5 | 6 | 7* | 8 | 9* | 10* | 11 | 12 | 13 | 14* | 15 | 16 | 17 | 18* | 19* | 20 | 21 | 22 | 23 | 24 | 26 |
| | | | | | | | | | | | Rate (kg/ha) | | | | | | | | | | | | | | |
| Species | 8 | 8 | 8 | 8 | 8 | 8 | 8 | 8 | 8 | 8 | 8 | 8 | 8 | 8 | 8 | 8 | 8 | 8 | 8 | 8 | 8 | 8 | 8 | 8 | 8 |
| SOYBEAN | | 0 | 0 | | 30 | 10 | 0 | 10 | 0 | 0 | 60 | 20 | 30 | | 50 | 0 | 50 | | 0 | 60 | 10 | 20 | 10 | 30 | 20 |
| LIMABEAN | 0 | 0 | 0 | 0 | | | 0 | | 0 | 0 | | | | 0 | | 0 | | 0 | 0 | | | | | | |
| CORN | | 0 | 0 | | 20 | 10 | 0 | 10 | 0 | 0 | 50 | 0 | 10 | | 20 | 0 | 20 | | 0 | 60 | 10 | 20 | 40 | 30 | 40 |
| WHEAT | | 0 | 0 | | 20 | 0 | 0 | 0 | 0 | 0 | 20 | 0 | 10 | | 10 | 0 | 0 | | 0 | 40 | 5 | 10 | 30 | 10 | 10 |
| TOMATO | 0 | 0 | 0 | 0 | | | 0 | | 0 | 0 | | | | 0 | | 0 | | 0 | 0 | | | | | | |
| VELVETLF | 0 | 0 | 0 | 0 | 0 | 0 | 0 | 10 | 0 | 0 | 60 | 0 | 30 | 0 | 30 | 0 | 0 | 0 | 0 | 40 | 0 | 10 | 20 | 10 | 10 |
| BINDWEED | 0 | 0 | 0 | 0 | | | 0 | | 0 | 0 | | | | 0 | | 0 | | 0 | 0 | | | | | | |
| WILDOAT | 0 | 0 | 0 | 0 | | | 0 | | 0 | 0 | | | | 0 | | 0 | | 0 | 0 | | | | | | |
| BARNYDGR | 0 | 0 | 0 | 0 | 30 | 20 | 0 | 10 | 0 | 0 | 20 | 10 | 10 | 0 | 40 | 0 | 40 | 0 | 0 | 40 | 20 | 40 | 30 | 30 | 20 |
| FOXGREEN | 0 | 0 | 0 | 0 | 10 | 0 | 0 | 20 | 0 | 0 | 20 | 0 | 20 | 0 | 30 | 0 | 20 | 0 | 0 | 30 | 10 | 30 | 40 | 10 | 10 |
| GLORYSPP | | | | | 20 | 0 | | 10 | | | 50 | 20 | 40 | | 40 | | 10 | | | 40 | 0 | 30 | 30 | 10 | 10 |
| COTTON | | | | | | | | | | | | | | | | | | | | | | | | | |
| JOHNGR | | | | | | | | | | | | | | | | | | | | | | | | | |
| RICE | | | | | | | | | | | | | | | | | | | | | | | | | |
| MUSTWILD | | | | | | | | | | | | | | | | | | | | | | | | | |

| | Compound No. | | | | | | | | | | | | | | | | | | | | | | | |
|---|---|---|---|---|---|---|---|---|---|---|---|---|---|---|---|---|---|---|---|---|---|---|---|---|
| | 27 | 28* | 29 | 30 | 31 | 32* | 33 | 34 | 35 | 36 | 37 | 38 | 39 | 40 | 41 | 42 | 43 | 44 | 45 | 46 | 47 | 48 | 49 | 50 | 51 | 52 |
| | | | | | | | | | | | | Rate (kg/ha) | | | | | | | | | | | | | |
| Species | 8 | 8 | 8 | 8 | 8 | 8 | 8 | 8 | 8 | 8 | 8 | 8 | 8 | 8 | 8 | 8 | 8 | 2 | 8 | 8 | 8 | 8 | 8 | 8 | 8 | 8 |
| SOYBEAN | 40 | 0 | 30 | 10 | 50 | 0 | 10 | 40 | 30 | 20 | 50 | 10 | 0 | 50 | 40 | 40 | 50 | 50 | 10 | 0 | 40 | 50 | 40 | 50 | 50 | 30 |
| LIMABEAN | | 0 | | | | 0 | | | | | | | | | | | | | | | | | | | | |
| CORN | 20 | 0 | 30 | 10 | 50 | 0 | 10 | 20 | 30 | 0 | 70 | 10 | 0 | 70 | 50 | 60 | 70 | 30 | 0 | 10 | 40 | 50 | 70 | 50 | 50 | 0 |
| WHEAT | 20 | 0 | 10 | 10 | 30 | 0 | 10 | 50 | 10 | 0 | 30 | 0 | 0 | 10 | 20 | 50 | 50 | 10 | 0 | 20 | 10 | 30 | 40 | 20 | 0 | 10 |
| TOMATO | | | | | | 0 | | | | | | | | | | | | | | | | | | | | |
| VELVETLF | 50 | 0 | 40 | 0 | 50 | 0 | 10 | 60 | 10 | 0 | 60 | 10 | 0 | 20 | 20 | 70 | 60 | 20 | 0 | 0 | 60 | 60 | 60 | 50 | 60 | 20 |
| BINDWEED | | 0 | | | | 0 | | | | | | | | | | | | | | | | | | | | |
| WILDOAT | | | | | | 0 | | | | | | | | | | | | | | | | | | | | |
| BARNYDGR | 50 | 0 | 40 | 20 | 60 | 0 | 20 | 30 | 30 | 0 | 70 | 10 | 0 | 30 | 40 | 70 | 70 | 15 | 10 | 20 | 70 | 70 | 80 | 60 | 70 | 10 |
| FOXGREEN | 50 | 40 | 70 | 10 | 70 | 0 | 60 | 50 | 10 | 10 | 70 | 20 | 0 | 20 | 30 | 70 | 60 | 10 | 60 | 10 | 30 | 70 | 70 | 80 | 50 | 50 |
| GLORYSPP | 50 | 0 | 40 | 0 | 40 | | 10 | 10 | 10 | 20 | 40 | 10 | 0 | 40 | 40 | 60 | 60 | 10 | 0 | 0 | 30 | 50 | 90 | 40 | 60 | 20 |
| COTTON | | | 5 | | | | | | | | | | | | | | | | | | | | | | | |
| JOHNGR | | 0 | | | | | | | | | | | | | | | | | | | | | | | | |
| RICE | | | | | | | | | | | | | | | | | | 10 | | | | | | | | |
| MUSTWILD | | | | | | | | | | | | | | | | | | 10 | | | | | | | | |

| | Compound No. | | | | | | | | | | | | | | | | | | | | | | | |
|---|---|---|---|---|---|---|---|---|---|---|---|---|---|---|---|---|---|---|---|---|---|---|---|---|
| | 53 | 54 | 55 | 56 | 57* | 58 | 59 | 60 | 61 | 62 | 63 | 64 | 65* | 66 | 67* | 68 | 69 | 70 | 71 | 72 | 73 | 74 | 75 | 76 | 77 |
| | | | | | | | | | | | | Rate (kg/ha) | | | | | | | | | | | | | |
| Species | 8 | 8 | 8 | 8 | 8 | 8 | 8 | 8 | 8 | 8 | 8 | 8 | 8 | 8 | 8 | 8 | 8 | 8 | 8 | 8 | 8 | 8 | 8 | 8 | 8 |
| SOYBEAN | 40 | 30 | 10 | 60 | | 50 | 50 | 40 | 50 | 60 | 40 | 20 | 0 | 10 | 0 | 50 | 40 | 30 | 30 | 0 | 20 | 20 | 40 | 10 | 30 |
| LIMABEAN | | | | | 0 | | | | | | | | 0 | | 0 | | | | | | | | | | |
| CORN | 20 | 40 | 10 | 60 | | 60 | 80 | 60 | 60 | 20 | 30 | 0 | 0 | 10 | 0 | 70 | 20 | 70 | 20 | 0 | 0 | 0 | 30 | 0 | 60 |
| WHEAT | 20 | 20 | 20 | 40 | | 5 | 30 | 30 | 40 | 20 | 20 | 0 | 0 | 0 | 0 | 50 | 20 | 15 | 20 | 0 | 0 | 0 | 50 | 0 | 20 |
| TOMATO | | | | | 0 | | | | | | | | 0 | | 0 | | | | | | | | | | |
| VELVETLF | 0 | 40 | 0 | 50 | 0 | 50 | 70 | 80 | 50 | 50 | 30 | 50 | 0 | 0 | 0 | 50 | 10 | 60 | 30 | 0 | 0 | 0 | 60 | 20 | 30 |
| BINDWEED | | | | | 0 | | | | | | | | 0 | | 0 | | | | | | | | | | |
| WILDOAT | | | | | 0 | | | | 0 | | 0 | | | | | | | | | | | | | | |
| BARNYDGR | 20 | 40 | 10 | 60 | | 40 | 80 | 50 | 70 | 60 | 50 | 10 | 0 | 0 | 0 | 70 | 20 | 90 | 30 | 0 | 0 | 0 | 60 | 30 | 80 |
| FOXGREEN | 20 | 50 | 10 | 50 | 0 | 20 | 80 | 70 | 70 | 60 | 20 | 50 | 0 | 0 | 0 | 60 | 40 | 10 | 10 | 0 | 50 | 0 | 80 | 0 | 40 |
| GLORYSPP | 20 | 40 | 10 | 60 | | 50 | 60 | 60 | 70 | 50 | 70 | 50 | | 10 | | 50 | 10 | 70 | 20 | 0 | 0 | 0 | 50 | 20 | 30 |
| COTTON | | | | | | | | | | | | | | | | | | 80 | | | | | | | |
| JOHNGR | | | | | | | | | | | | | | | | | | 10 | | | | | | | |
| RICE | | | | | | | | | | | | | | | | | | 30 | | | | | | | |
| MUSTWILD | | | | | | | | | | | | | | | | | | 40 | | | | | | | |

| | Compound No. | | | | | | | | | | | | | | | | | | | | | | | |
|---|---|---|---|---|---|---|---|---|---|---|---|---|---|---|---|---|---|---|---|---|---|---|---|---|
| | 78 | 79 | 80 | 81* | 82 | 83 | 84 | 85 | 86 | 87 | 88* | 89 | 90 | 91 | 92 | 93 | 94 | 95 | 96 | 97 | 98 | 99* | 100* | 101* |
| | | | | | | | | | | | Rate (kg/ha) | | | | | | | | | | | | | |
| Species | 8 | 8 | 8 | 8 | 8 | 8 | 8 | 8 | 8 | 8 | 8 | 8 | 8 | 8 | 8 | 8 | 8 | 8 | 8 | 8 | 8 | 8 | 8 | 8 |
| SOYBEAN | 10 | 30 | 20 | 0 | 0 | 10 | 30 | 0 | 50 | 10 | 0 | 50 | 60 | 50 | 10 | 20 | 30 | 50 | 50 | 50 | 50 | 0 | 0 | 0 |
| LIMABEAN | | | | 0 | | | | | | | 0 | | | | | | | | | | | 0 | 0 | 0 |
| CORN | 20 | 40 | 0 | 0 | 10 | 20 | 20 | 60 | 20 | 40 | 0 | 30 | 70 | 50 | 10 | 10 | 10 | 60 | 70 | 70 | 80 | 0 | 0 | 0 |
| WHEAT | 20 | 40 | 0 | 0 | 10 | 10 | 20 | 10 | 40 | 0 | 0 | 30 | 20 | 40 | 10 | 10 | 20 | 50 | 50 | 50 | 40 | 0 | 0 | 0 |
| TOMATO | | | | 0 | | | | | | | 20 | | | | | | | | | | | 0 | 0 | 0 |
| VELVETLF | 10 | 60 | 0 | 0 | 10 | 20 | 40 | 30 | 30 | 70 | 0 | 40 | 30 | 80 | 0 | 30 | 30 | 60 | 80 | 70 | 60 | 0 | 0 | 0 |

TABLE 4-continued

Postemergence Herbicidal Activity (% Control)

| | | | | 0 | | | | | | 0 | | | | | | | | | | | 0 | 0 | 0 |
|---|---|---|---|---|---|---|---|---|---|---|---|---|---|---|---|---|---|---|---|---|---|---|---|
| BINDWEED | | | | 0 | | | | | | 0 | | | | | | | | | | | 0 | 0 | 0 |
| WILDOAT | | | | 0 | | | | | | 0 | | | | | | | | | | | 0 | 0 | 0 |
| BARNYDGR | 10 | 60 | 0 | 0 | 20 | 20 | 30 | 70 | 50 | 30 | 0 | 40 | 70 | 60 | 10 | 90 | 20 | 70 | 90 | 70 | 70 | 0 | 0 | 0 |
| FOXGREEN | 10 | 40 | 10 | 0 | 30 | 50 | 80 | 50 | 40 | 40 | 0 | 50 | 20 | 60 | 20 | 70 | 20 | 50 | 60 | 70 | 50 | 0 | 0 | 0 |
| GLORYSPP | 10 | 30 | 30 | | 10 | 10 | 50 | 10 | 20 | 80 | | 30 | 60 | 50 | 0 | 10 | 10 | 50 | 60 | 50 | 40 | | | |
| COTTON | | | | | | | | | | | | | | | | | | | | | | | | |
| JOHNGR | | | | | | | | | | | | | | | | | | | | | | | | |
| RICE | | | | | | | | | | | | | | | | | | | | | | | | |
| MUSTWILD | | | | | | | | | | | | | | | | | | | | | | | | |

| | Compound No. | | | | | | | | | | | | | | | | | |
|---|---|---|---|---|---|---|---|---|---|---|---|---|---|---|---|---|---|---|
| | 102* | 103* | 104 | 105 | 106 | 107 | 108 | 109 | 110 | 111 | 112 | 113 | 114* | 115 | 116 | 117 | 118 | 119 |
| | | | | | | | | | Rate (kg/ha) | | | | | | | | | |
| Species | 8 | 8 | 8 | 8 | 8 | 8 | 8 | 8 | 8 | 8 | 8 | 8 | 8 | 8 | 8 | 8 | 8 | 8 |
| SOYBEAN | 0 | 0 | 30 | 60 | 40 | 40 | 50 | 40 | 30 | 60 | 30 | 20 | 0 | 50 | 0 | 40 | 30 | 10 |
| LIMABEAN | 0 | 0 | | | | | | | | | | | 0 | | | | | |
| CORN | 0 | 0 | 40 | 70 | 60 | 70 | 70 | 70 | 20 | 80 | 20 | 10 | 0 | 50 | 0 | 60 | 30 | 80 |
| WHEAT | 0 | 0 | 20 | 10 | 0 | 40 | 50 | 50 | 0 | 60 | 0 | 0 | 0 | 20 | 0 | 20 | 10 | 20 |
| TOMATO | 0 | 0 | | | | | | | | | | | 0 | | | | | |
| VELVETLF | 0 | 0 | 30 | 50 | 40 | 20 | 50 | 20 | 20 | 80 | 20 | 10 | 0 | 30 | 0 | 80 | 30 | 20 |
| BINDWEED | 0 | 0 | | 30 | | | | | | | | | 0 | | | | | |
| WILDOAT | 0 | 0 | | | | | | | | | | | 0 | | | | | |
| BARNYDGR | 0 | 0 | 40 | 60 | 60 | 70 | 80 | 70 | 30 | 90 | 0 | 20 | 0 | 50 | 0 | 90 | 60 | 95 |
| FOXGREEN | 0 | 0 | 90 | 100 | 40 | 40 | 70 | 20 | 30 | 60 | 20 | 10 | 0 | 60 | 0 | 60 | 70 | 20 |
| GLORYSPP | | | 30 | 60 | 60 | 50 | 50 | 50 | 20 | 70 | 10 | 10 | | 40 | 0 | 60 | 50 | 10 |
| COTTON | | | | 50 | | | | | | | | | | | | | | |
| JOHNGR | | | | 100 | | | | | | | | | | | | | | |
| RICE | | | | | | | | | | | | | | | | | | |
| MUSTWILD | | | | | | | | | | | | | | | | | | |

| | Compound No. | | | | | | | | | | | | | | | | | |
|---|---|---|---|---|---|---|---|---|---|---|---|---|---|---|---|---|---|---|
| | 122 | 123 | 124 | 125 | 126 | 127 | 128 | 129 | 130 | 131 | 132 | 133 | 134 | 135 | 136 | 137 | 138 | 139 |
| | | | | | | | | | Rate (kg/ha) | | | | | | | | | |
| Species | 8 | 8 | 8 | 8 | 8 | 8 | 8 | 8 | 8 | 8 | 8 | 8 | 8 | 8 | 4 | 8 | 8 | 8 |
| SOYBEAN | 5 | 40 | 30 | 10 | 60 | 0 | 50 | 10 | 0 | 40 | 40 | 10 | 0 | 30 | 20 | 60 | 80 | 30 |
| LIMABEAN | | | | | | | | | | | | | | | | | | |
| CORN | 20 | 50 | 20 | 10 | 50 | 10 | 40 | 10 | 0 | 30 | 50 | 0 | 0 | 20 | 20 | 70 | 70 | 0 |
| WHEAT | 30 | 40 | 30 | 10 | 20 | 0 | 0 | 0 | 0 | 10 | 40 | 0 | 0 | 10 | 10 | 50 | 20 | 0 |
| TOMATO | | | | | | | | | | | | | | | | | | |
| VELVETLF | 0 | 30 | 30 | 10 | 20 | 0 | 30 | 10 | 0 | 40 | 20 | 0 | 0 | 20 | 30 | 60 | 50 | 60 |
| BINDWEED | | | | | | | | | | | | | | | | | | |
| WILDOAT | | | | | | | | | | | | | | | | | | |
| BARNYDGR | 10 | 70 | 30 | 10 | 50 | 10 | 40 | 40 | 0 | 60 | 70 | 0 | 0 | 50 | 30 | 50 | 80 | 20 |
| FOXGREEN | 10 | 70 | 30 | 10 | 20 | 10 | 60 | 10 | 0 | 40 | 30 | 0 | 0 | 50 | 20 | 60 | 70 | 50 |
| GLORYSPP | 0 | 60 | 30 | 10 | 60 | 0 | 30 | 10 | 0 | 60 | 30 | 0 | 0 | 10 | 40 | 60 | 60 | 60 |
| COTTON | | | | | | | | | | | | | | | 10 | | | |
| JOHNGR | | | | | | | | | | | | | | | 30 | | | |
| RICE | | | | | | | | | | | | | | | 20 | | | |
| MUSTWILD | | | | | | | | | | | | | | | 30 | | | |

| | Compound No. | | | | | | | | | | | | | | | | | |
|---|---|---|---|---|---|---|---|---|---|---|---|---|---|---|---|---|---|---|
| | 140 | 141 | 142 | 143 | 144 | 146 | 147 | 148 | 149 | 150 | 151 | 152 | 153 | 154 | 155 | 156 | 157 | 158 |
| | | | | | | | | | Rate (kg/ha) | | | | | | | | | |
| Species | 8 | 8 | 8 | 8 | 8 | 8 | 2 | 8 | 8 | 8 | 8 | 8 | 8 | 8 | 8 | 8 | 8 | 8 |
| SOYBEAN | 50 | 60 | 50 | 50 | 50 | 50 | 10 | 40 | 30 | 40 | 60 | 60 | 50 | 20 | 70 | 40 | 30 | 40 |
| LIMABEAN | | | | | | | | | | | | | | | | | | |
| CORN | 50 | 60 | 70 | 80 | 30 | 40 | 100 | 70 | 40 | 60 | 40 | 70 | 80 | 40 | 70 | 60 | 70 | 70 |
| WHEAT | 40 | 40 | 50 | 20 | 10 | 10 | 20 | 10 | 10 | 40 | 40 | 60 | 60 | 10 | 30 | 20 | 40 | 20 |
| TOMATO | | | | | | | | | | | | | | | | | | |
| VELVETLF | 70 | 30 | 20 | 40 | 70 | 50 | 90 | 30 | 70 | 60 | 80 | 50 | 80 | 30 | 40 | 60 | 80 | 50 |
| BINDWEED | | | | | | | | | | | | | | | | | | |
| WILDOAT | | | | | | | | | | | | | | | | | | |
| BARNYDGR | 70 | 80 | 60 | 50 | 70 | 50 | 20 | 60 | 80 | 70 | 80 | 80 | 80 | 20 | 70 | 70 | 70 | 60 |
| FOXGREEN | 70 | 10 | 0 | 10 | 70 | 40 | 70 | 30 | 60 | 40 | 60 | 90 | 90 | 0 | 40 | 30 | 70 | 90 |
| GLORYSPP | 60 | 20 | 30 | 40 | 60 | 50 | 40 | 30 | 60 | 60 | 70 | 50 | 80 | 10 | 70 | 70 | 60 | 30 |
| COTTON | | | | | | | 60 | | 20 | | | | | | 50 | | | |
| JOHNGR | | | | | | | 30 | | 80 | | | | | | 90 | | | |
| RICE | | | | | | | 20 | | 10 | | | | | | 50 | | | |
| MUSTWILD | | | | | | | 20 | | 80 | | | | | | 30 | | | |

| | Compound No. | | | | | | | | | | | | | | | | | |
|---|---|---|---|---|---|---|---|---|---|---|---|---|---|---|---|---|---|---|
| | 159 | 160* | 161 | 162 | 163 | 164 | 165 | 166 | 167 | 168* | 169* | 170* | 172* | 173* | 174* | 175* | 176* | 177 |
| | | | | | | | | | Rate (kg/ha) | | | | | | | | | |
| Species | 8 | 8 | 8 | 8 | 8 | 8 | 8 | 8 | 8 | 8 | 8 | 8 | 8 | 8 | 8 | 8 | 8 | 8 |
| SOYBEAN | 5 | 0 | 20 | 40 | 10 | 60 | 30 | 50 | 20 | | | 0 | | | | | | 10 |
| LIMABEAN | | 0 | | | | | | | | 0 | 0 | 0 | 0 | 0 | 0 | 0 | 0 | |
| CORN | 10 | 0 | 50 | 40 | 20 | 70 | 50 | 60 | 10 | | | 0 | | | | | | 10 |
| WHEAT | 10 | 0 | 40 | 10 | 20 | 50 | 30 | 40 | 10 | | | 0 | | | | | | 0 |
| TOMATO | | 0 | | | | | | | | 0 | 0 | 0 | 0 | 0 | 0 | 0 | 0 | |

TABLE 4-continued

Postemergence Herbicidal Activity (% Control)

| Species | | | | | | | | | | | | | | | | | | |
|---|---|---|---|---|---|---|---|---|---|---|---|---|---|---|---|---|---|---|
| VELVETLF | 20 | 0 | 80 | 40 | 0 | 50 | 40 | 60 | 0 | 0 | 0 | 0 | 0 | 0 | 0 | 0 | 0 | 0 |
| BINDWEED | | 0 | | | | | | | | 0 | 0 | 0 | 0 | 0 | 0 | 0 | 0 | |
| WILDOAT | | 0 | | | | | | | | 0 | 0 | 0 | 0 | 0 | 0 | 0 | 0 | |
| BARNYDGR | 20 | | 90 | 60 | 0 | 70 | 40 | 80 | 10 | 0 | 0 | 0 | 0 | 0 | 0 | 0 | 0 | 0 |
| FOXGREEN | 10 | 0 | 80 | 60 | 0 | 80 | 50 | 90 | 10 | 0 | 0 | 0 | 0 | 0 | 0 | 0 | 0 | 0 |
| GLORYSPP | 20 | | 80 | 30 | 20 | 50 | 40 | 60 | 20 | | | | | | | | | 0 |
| COTTON | | | | | | | | | | | | | | | | | | |
| JOHNGR | | | | | | | | | | | | | | | | | | |
| RICE | | | | | | | | | | | | | | | | | | |
| MUSTWILD | | | | | | | | | | | | | | | | | | |

| | Compound No. | | | | | | | | | | | | | | | | | |
|---|---|---|---|---|---|---|---|---|---|---|---|---|---|---|---|---|---|---|
| | 178 | 179 | 180 | 181 | 182 | 183 | 184 | 185 | 186 | 187 | 188 | 189 | 190 | 191 | 192 | 193 | 194 | 195 |
| | Rate (kg/ha) | | | | | | | | | | | | | | | | | |
| Species | 8 | 8 | 8 | 8 | 8 | 8 | 8 | 8 | 8 | 8 | 8 | 8 | 8 | 8 | 8 | 8 | 8 | 8 |
| SOYBEAN | 0 | 0 | 50 | 50 | 30 | 50 | 40 | 40 | 60 | 40 | 20 | 40 | 20 | 60 | 10 | 50 | 40 | 30 |
| LIMABEAN | | | | | | | | | | | | | | | | | | |
| CORN | 0 | 0 | 70 | 70 | 30 | 20 | 20 | 20 | 30 | 20 | 10 | 30 | 10 | 30 | 10 | 20 | 50 | 30 |
| WHEAT | 0 | 0 | 10 | 20 | 20 | 20 | 20 | 10 | 40 | 20 | 0 | 10 | 10 | 30 | 10 | 30 | 20 | 30 |
| TOMATO | | | | | | | | | | | | | | | | | | |
| VELVETLF | 0 | 0 | 60 | 50 | 30 | 10 | 10 | 0 | 70 | 0 | 10 | 30 | 10 | 70 | 0 | 20 | 40 | 30 |
| BINDWEED | | | | | | | | | | | | | | | | | | |
| WILDOAT | | | | | | | | | | | | | | | | | | |
| BARNYDGR | 0 | 0 | 80 | 50 | 90 | 30 | 10 | 20 | 90 | 40 | 10 | 20 | 30 | 50 | 10 | 30 | 50 | 60 |
| FOXGREEN | 0 | 60 | 60 | 50 | 20 | 60 | 10 | 50 | 100 | 30 | 20 | 30 | 10 | 50 | 10 | 40 | 70 | 80 |
| GLORYSPP | 0 | 0 | 50 | 40 | 20 | 10 | 10 | 0 | 80 | 0 | 10 | 20 | 10 | 70 | 0 | 60 | 70 | 30 |
| COTTON | | | | | | | | | | | | | | | | | | |
| JOHNGR | | | | | | | | | | | | | | | | | | |
| RICE | | | | | | | | | | | | | | | | | | |
| MUSTWILD | | | | | | | | | | | | | | | | | | |

| | Compound No. | | | | | | | | | | | | | | | | | |
|---|---|---|---|---|---|---|---|---|---|---|---|---|---|---|---|---|---|---|
| | 196 | 197 | 198 | 199 | 200 | 201 | 204 | 205 | 206 | 208 | 209 | 210 | 211 | 212 | 213 | 215 | 216 | 220 |
| | Rate (kg/ha) | | | | | | | | | | | | | | | | | |
| Species | 8 | 8 | 8 | 8 | 8 | 8 | 8 | 1 | 8 | 0.5 | 8 | 8 | 8 | 8 | 8 | 8 | 8 | 0.5 |
| SOYBEAN | 0 | 50 | 50 | 10 | 20 | 10 | 20 | 50 | 60 | 60 | 50 | 0 | 60 | 40 | 40 | 70 | 60 | 70 |
| LIMABEAN | | | | | | | | | | | | | | | | | | |
| CORN | 0 | 40 | 50 | 0 | 0 | 0 | 10 | 80 | 70 | 20 | 0 | 0 | 60 | 40 | 20 | 0 | 80 | 60 |
| WHEAT | 0 | 30 | 20 | 0 | 0 | 0 | 10 | 10 | 70 | 5 | 30 | 0 | 60 | 20 | 20 | 30 | 20 | 10 |
| TOMATO | | | | | | | | | | | | | | | | | | |
| VELVETLF | 0 | 30 | 50 | 0 | 20 | 0 | 20 | 40 | 80 | 85 | 60 | 50 | 95 | 70 | 70 | 50 | 60 | 80 |
| BINDWEED | | | | | | | | | | | | | | | | | | |
| WILDOAT | | | | | | | | | | | | | | | | | | |
| BARNYDGR | 0 | 60 | 40 | 0 | 30 | 0 | 10 | 15 | 70 | 70 | 50 | 0 | 50 | 50 | 40 | 50 | 70 | 70 |
| FOXGREEN | 0 | 20 | 50 | 0 | 0 | 0 | 20 | 70 | 80 | 95 | 90 | 0 | 50 | 90 | 80 | 40 | 80 | 85 |
| GLORYSPP | 0 | 60 | 60 | 0 | 20 | 0 | 20 | 40 | 70 | 70 | 50 | 40 | 50 | 70 | 50 | 70 | 40 | 70 |
| COTTON | | | | | | | | 20 | | 30 | | | | | | | | 30 |
| JOHNGR | | | | | | | | 10 | | 80 | | | | | | | | 90 |
| RICE | | | | | | | | 10 | | 5 | | | | | | | | 5 |
| MUSTWILD | | | | | | | | 50 | | 70 | | | | | | | | 15 |

| | Compound No. | | | | | | | | | | | | | | | | | |
|---|---|---|---|---|---|---|---|---|---|---|---|---|---|---|---|---|---|---|
| | 221 | 223 | 224 | 225 | 232 | 234 | 235 | 236 | 237 | 238 | 239 | 240 | 241 | 242 | 243 | 244 | 245 | 246 |
| | Rate (kg/ha) | | | | | | | | | | | | | | | | | |
| Species | 8 | 8 | 8 | 8 | 8 | 8 | 1 | 2 | 8 | 8 | 1 | 8 | 8 | 8 | 8 | 8 | 8 | 8 |
| SOYBEAN | 30 | 50 | 10 | 10 | 60 | 40 | 35 | 30 | 50 | 50 | 30 | 40 | 50 | 40 | 20 | 40 | 50 | 50 |
| LIMABEAN | | | | | | | | | | | | | | | | | | |
| CORN | 0 | 50 | 50 | 0 | 70 | 10 | 60 | 30 | 70 | 60 | 20 | 70 | 70 | 20 | 10 | 40 | 60 | 80 |
| WHEAT | 10 | 10 | 10 | 0 | 50 | 20 | 40 | 15 | 50 | 30 | 10 | 30 | 60 | 20 | 0 | 20 | 40 | 60 |
| TOMATO | | | | | | | | | | | | | | | | | | |
| VELVETLF | 60 | 30 | 20 | 0 | 20 | 0 | 80 | 50 | 50 | 60 | 50 | 50 | 60 | 40 | 40 | 20 | 50 | 30 |
| BINDWEED | | | | | | | | | | | | | | | | | | |
| WILDOAT | | | | | | | | | | | | | | | | | | |
| BARNYDGR | 40 | 40 | 30 | 0 | 70 | 40 | 60 | 20 | 70 | 80 | 40 | 90 | 80 | 30 | 0 | 10 | 50 | 40 |
| FOXGREEN | 60 | 20 | 20 | 0 | 10 | 10 | 70 | 20 | 70 | 70 | 50 | 50 | 90 | 30 | 0 | 30 | 80 | 80 |
| GLORYSPP | 60 | 40 | 20 | 0 | 20 | 30 | 60 | 70 | 60 | 60 | 50 | 60 | 50 | 40 | 30 | 20 | 50 | 30 |
| COTTON | | | | | | | 30 | 30 | | | 5 | | | | | | | |
| JOHNGR | | | | | | | 60 | 15 | | | 40 | | | | | | | |
| RICE | | | | | | | 50 | 15 | | | 10 | | | | | | | |
| MUSTWILD | | | | | | | 95 | 10 | | | 40 | | | | | | | |

| | Compound No. | | | | | | |
|---|---|---|---|---|---|---|---|
| | 247 | 248 | 249 | 250 | 251 | 252 | 261 |
| | Rate (kg/ha) | | | | | | |
| Species | 8 | 8 | 8 | 1 | 8 | 1 | 8 |
| SOYBEAN | 50 | 40 | 60 | 60 | 50 | 70 | 60 |
| LIMABEAN | | | | | | | |
| CORN | 60 | 20 | 80 | 70 | 30 | 90 | 30 |
| WHEAT | 30 | 0 | 60 | 10 | 30 | 30 | 20 |

TABLE 4-continued

| | Postemergence Herbicidal Activity (% Control) | | | | | | |
|---|---|---|---|---|---|---|---|
| TOMATO | | | | | | | |
| VELVETLF | 30 | 40 | 70 | 60 | 60 | 70 | 60 |
| BINDWEED | | | | | | | |
| WILDOAT | | | | | | | |
| BARNYDGR | 40 | 40 | 60 | 70 | 20 | 70 | 20 |
| FOXGREEN | 30 | 70 | 70 | 90 | 70 | 70 | 70 |
| GLORYSPP | 20 | 40 | 50 | 60 | 60 | 50 | 20 |
| COTTON | | | | 30 | | 40 | |
| JOHNGR | | | | 80 | | 70 | |
| RICE | | | | 50 | | 40 | |
| MUSTWILD | | | | 60 | | 80 | |

*Data represents % Kill (% K) rather than % Control (% C)

We claim:
1. A compound of formula

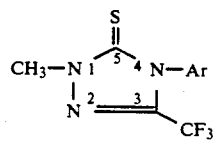

wherein:
Ar is

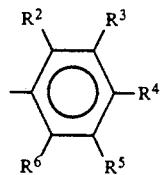

$R^2$ is hydrogen, halogen, alkyl, haloalkoxy, haloalkyl, or alkoxy, and;

$R^3$ is hydrogen, halogen, alkyl, alkoxy, amino, or mono- or disubstituted amino;

$R^4$ is hydrogen, halogen, alkyl, alkenyl, alkynyl, amino, haloalkyl, mono- or disubstituted amino, alkoxy, alkylthio, alkylthioalkoxy, vinyloxy, alkylvinyloxy, halovinyloxy, allyloxy, cycloalkoxy, or haloalkoxy;

$R^5$ is hydrogen, halogen, alkyl, alkoxy, haloalkoxy, or haloalkyl; and $R^6$ is hydrogen, halogen, alkyl, or alkylthio; provided that each alkyl group and alkyl portion of any group contain 1-6 carbon atoms, that each alkenyl and alkynyl group and each alkenyl and alkynyl portion of any group contain 3-6 carbon atoms, and that each amino substituent of $R^3$ and $R^4$ is selected from alkyl or fluoroalkyl of 1 to 4 carbon atoms.

2. A compound of claim 1 in which
$R^2$ is hydrogen, halogen, alkyl, haloalkyl, or haloalkoxy;
$R^4$ is halogen, alkyl, alkoxy, vinyloxy, cycloalkoxy, haloalkyl, haloalkoxy, or mono- or disubstituted amino;
$R^5$ is hydrogen, halogen, alkyl, or haloalkoxy; and
$R^6$ is hydrogen or halogen, provided that each amino substituent of $R^3$ and $R^4$ contains 1 or 2 carbon atoms.

3. A compound of claim 2 in which
$R^2$ is hydrogen, methyl, chlorine, fluorine, bromine, trifluoromethyl, or difluoromethoxy;
$R^3$ is hydrogen, methyl, chlorine, fluorine, methoxy, isopropoxy, amino, or dimethylamino;

$R^4$ is bromine, chlorine, fluorine, iodine, alkyl, alkoxy, cycloalkoxy, haloalkyl, haloalkoxy, vinyloxy, or mono- or disubstituted amino;

$R^5$ is hydrogen, bromine, chlorine, fluorine, methyl, methoxy, or difluoromethoxy; and $R^6$ is hydrogen, chlorine, or fluorine.

4. A compound of claim 3 in which
$R^2$ is hydrogen, methyl, chlorine, fluorine, or difluoromethoxy;
$R^3$ is hydrogen or fluorine;
$R^4$ is bromine, chlorine, cyclobutoxy, isopropoxy, propoxy, vinyloxy, or diethylamino;
$R^5$ is hydrogen, chlorine, fluorine, or difluoromethoxy; and
$R^6$ is hydrogen.

5. A compound of claim 4 in which
$R^2$ and $R^5$ are independently selected from chlorine and difluoromethoxy;
$R^3$ is hydrogen; and
$R^4$ is isopropoxy.

6. A compound of claim 4 in which
$R^2$, $R^3$, and $R^5$ are hydrogen; and
$R^4$ is bromine.

7. The compound of claim 4 in which
$R^2$ is hydrogen;
$R^3$ and $R^5$ are fluorine; and
$R^4$ is chlorine.

8. The compound of claim 4 in which
$R^2$ is fluorine;
$R^3$ is hydrogen;
$R^4$ is diethylamino; and
$R^5$ is chlorine.

9. The compound of claim 4 in which $R^2$ and $R^3$ are chlorine, $R^3$ and $R^6$ are hydrogen, and $R^4$ is

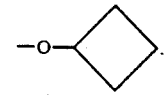

10. The compound of claim 4 in which $R^2$ is fluorine, $R^3$ and $R^6$ are hydrogen, $R^4$ is $OCH(CH_3)_2$, and $R^5$ is chlorine.

11. The compound of claim 4 in which $R^2$ and $R^5$ are chlorine, $R^3$ and $R^6$ are hydrogen, and $R^4$ is $OCH=CH_2$.

12. The compound of claim 4 in which $R^3$ and $R^6$ are hydrogen, $R^2$ and $R^5$ are chlorine, and $R^4$ is $OCH_2CH_2CH_3$.

13. The compound of claim 4 in which $R^3$ and $R^6$ are hydrogen, $R^2$ and $R^5$ are chlorine, and $R^4$ is $OCH(CH_3)_2$.

14. A herbicidal composition comprising a herbicidally effective amount of the compound of claim 1 in admixture with a suitable carrier.

15. A method for controlling undesired plant growth which comprises applying to the locus where control is desired a herbicidally effective composition of claim 4.

* * * * *